(12) United States Patent
Langlois et al.

(10) Patent No.: US 9,044,346 B2
(45) Date of Patent: Jun. 2, 2015

(54) POWERED PROSTHETIC HIP JOINT

(71) Applicant: Össur hf, Reykjavik (IS)

(72) Inventors: David Langlois, Saint-Jacques-de-Leeds (CA); Arinbjörn Viggo Clausen, Reykjavik (IS); Árni Einarsson, Reykjavik (IS)

(73) Assignee: Össur hf, Reykjavik (IS)

( * ) Notice: Subject to any disclaimer, the term of this patent is extended or adjusted under 35 U.S.C. 154(b) by 0 days.

(21) Appl. No.: 13/837,124

(22) Filed: Mar. 15, 2013

(65) Prior Publication Data

US 2013/0261766 A1 Oct. 3, 2013

Related U.S. Application Data

(60) Provisional application No. 61/617,540, filed on Mar. 29, 2012.

(51) Int. Cl.
| | | |
|---|---|---|
| *A61F 2/48* | (2006.01) | |
| *A61F 2/74* | (2006.01) | |
| *A61F 2/60* | (2006.01) | |
| *A61F 2/68* | (2006.01) | |
| *A61F 2/64* | (2006.01) | |

(Continued)

(52) U.S. Cl.
CPC . *A61F 2/60* (2013.01); *A61F 2/605* (2013.01); *A61F 2/64* (2013.01); *A61F 2/66* (2013.01); *A61F 2/68* (2013.01); *A61F 2002/6836* (2013.01); *A61F 2002/701* (2013.01); *A61F 2002/705* (2013.01); *A61F 2002/7625* (2013.01); *A61F 2002/7635* (2013.01); *A61F 2002/7645* (2013.01)

(58) Field of Classification Search
CPC ........................................................ A61F 2/605
USPC ........................................................... 623/24
See application file for complete search history.

(56) References Cited

U.S. PATENT DOCUMENTS

| 909,859 | A | 1/1909 | Apgar |
|---|---|---|---|
| 4,030,141 | A | 6/1977 | Graupe |

(Continued)

FOREIGN PATENT DOCUMENTS

| CA | 2546858 | 6/2005 |
|---|---|---|
| CN | 1074109 | 7/1993 |

(Continued)

OTHER PUBLICATIONS

Akio Nakagawa, Intelligent Knee Mechanism and the Possibility to Apply the Principle to the Other Joints, Engineering in Medicine and Biology Society, Proceedings of the 20th Annual International Conference of the IEEE vol. 20, No. 5, Dec. 1998, at 2282 ("Nakagawa").

(Continued)

*Primary Examiner* — Jacqueline Woznicki
(74) *Attorney, Agent, or Firm* — Knobbe Martens Olson & Bear LLP

(57) ABSTRACT

A powered prosthetic thigh can have a proximal portion configured to couple to a prosthetic hip socket and can have a distal portion attached to the proximal portion. The distal portion can have a distal connector configured to couple to a prosthetic knee. The powered prosthetic thigh can also have a computer controlled actuator configured to rotate the prosthetic thigh relative to the prosthetic hip socket.

15 Claims, 29 Drawing Sheets

(51) Int. Cl.
*A61F 2/66* (2006.01)
*A61F 2/70* (2006.01)
*A61F 2/76* (2006.01)

(56) References Cited

U.S. PATENT DOCUMENTS

| | | | |
|---|---|---|---|
| 4,398,109 | A | 8/1983 | Kuwako et al. |
| 4,579,558 | A * | 4/1986 | Ramer ........................ 403/24 |
| 5,200,679 | A | 4/1993 | Graham |
| 5,252,102 | A | 10/1993 | Singer et al. |
| 5,253,656 | A | 10/1993 | Rincoe et al. |
| 5,406,845 | A | 4/1995 | Berger et al. |
| 5,443,528 | A | 8/1995 | Allen |
| 5,486,209 | A | 1/1996 | Phillips |
| 5,571,213 | A | 11/1996 | Allen |
| 5,725,598 | A | 3/1998 | Phillips |
| 5,984,972 | A | 11/1999 | Huston et al. |
| 6,122,960 | A | 9/2000 | Hutchings et al. |
| 6,322,594 | B1 | 11/2001 | Boiten et al. |
| 6,379,393 | B1 | 4/2002 | Mavroidis et al. |
| 6,443,993 | B1 | 9/2002 | Koniuk |
| 6,517,503 | B1 | 2/2003 | Naft et al. |
| 6,610,101 | B2 | 8/2003 | Herr et al. |
| 6,679,920 | B2 | 1/2004 | Biedermann et al. |
| 6,704,024 | B2 | 3/2004 | Robotham et al. |
| 6,704,582 | B2 | 3/2004 | Le-Faucheur et al. |
| 6,755,870 | B1 | 6/2004 | Biedermann et al. |
| 6,764,520 | B2 | 7/2004 | Deffenbaugh et al. |
| 6,770,045 | B2 | 8/2004 | Naft et al. |
| 6,875,241 | B2 | 4/2005 | Christensen |
| 6,918,308 | B2 | 7/2005 | Biedermann |
| 6,966,882 | B2 | 11/2005 | Horst |
| 7,029,500 | B2 | 4/2006 | Martin |
| 7,066,964 | B2 | 6/2006 | Wild |
| 7,147,667 | B2 | 12/2006 | Bédard |
| 7,198,071 | B2 | 4/2007 | Bisbee et al. |
| 7,279,009 | B2 | 10/2007 | Herr |
| 7,313,463 | B2 | 12/2007 | Herr et al. |
| 7,455,696 | B2 | 11/2008 | Bisbee, III et al. |
| 7,475,606 | B2 | 1/2009 | Selig et al. |
| 7,485,152 | B2 | 2/2009 | Haynes et al. |
| 7,500,407 | B2 | 3/2009 | Boiten |
| 7,531,006 | B2 | 5/2009 | Clausen et al. |
| 7,552,664 | B2 | 6/2009 | Bulatowicz |
| 7,578,799 | B2 | 8/2009 | Thorsteinsson et al. |
| 7,597,017 | B2 | 10/2009 | Bédard et al. |
| 7,602,301 | B1 | 10/2009 | Stirling et al. |
| 7,611,543 | B2 | 11/2009 | Townsend et al. |
| 7,637,959 | B2 | 12/2009 | Clausen et al. |
| 7,691,154 | B2 | 4/2010 | Asgeirsson et al. |
| 7,736,394 | B2 | 6/2010 | Bédard et al. |
| 7,794,505 | B2 | 9/2010 | Clausen et al. |
| 7,799,091 | B2 | 9/2010 | Herr et al. |
| 7,811,333 | B2 | 10/2010 | Jónsson et al. |
| 7,862,620 | B2 | 1/2011 | Clausen et al. |
| 7,867,285 | B2 | 1/2011 | Clausen et al. |
| 7,896,927 | B2 | 3/2011 | Clausen et al. |
| 7,953,549 | B2 | 5/2011 | Graham et al. |
| 7,963,998 | B2 | 6/2011 | Boiten |
| RE42,903 | E | 11/2011 | Deffenbaugh et al. |
| 8,048,172 | B2 | 11/2011 | Jonsson et al. |
| 8,122,772 | B2 | 2/2012 | Clausen et al. |
| 8,142,370 | B2 | 3/2012 | Weinberg et al. |
| 8,435,309 | B2 | 5/2013 | Gilbert et al. |
| 8,555,715 | B2 | 10/2013 | Langlois et al. |
| 8,617,254 | B2 | 12/2013 | Bisbee, III et al. |
| 8,709,097 | B2 | 4/2014 | Jonsson et al. |
| 2001/0020143 | A1 | 9/2001 | Stark et al. |
| 2001/0029400 | A1 | 10/2001 | Deffenbaugh et al. |
| 2002/0094919 | A1 | 7/2002 | Rennex et al. |
| 2004/0073149 | A1* | 4/2004 | Okediji ........................ 602/23 |
| 2004/0086240 | A1 | 5/2004 | Togami et al. |
| 2004/0153484 | A1 | 8/2004 | Unno |
| 2005/0049719 | A1 | 3/2005 | Wilson |
| 2005/0107889 | A1 | 5/2005 | Bédard et al. |
| 2005/0283257 | A1 | 12/2005 | Bisbee et al. |
| 2006/0069336 | A1 | 3/2006 | Krebs et al. |
| 2006/0136072 | A1 | 6/2006 | Bisbee et al. |
| 2006/0249315 | A1 | 11/2006 | Herr et al. |
| 2006/0259153 | A1 | 11/2006 | Harn et al. |
| 2007/0032748 | A1 | 2/2007 | McNeil et al. |
| 2007/0123997 | A1* | 5/2007 | Herr et al. ........................ 623/27 |
| 2008/0133171 | A1 | 6/2008 | Feichtinger et al. |
| 2009/0054996 | A1 | 2/2009 | Sykes |
| 2009/0056445 | A1 | 3/2009 | Veltink |
| 2009/0171469 | A1 | 7/2009 | Thorsteinsson et al. |
| 2009/0265018 | A1 | 10/2009 | Goldfarb et al. |
| 2009/0299480 | A1 | 12/2009 | Gilbert et al. |
| 2009/0312844 | A1 | 12/2009 | Ikeuchi et al. |
| 2010/0023133 | A1 | 1/2010 | Fairbanks et al. |
| 2010/0042256 | A1 | 2/2010 | Takenaka et al. |
| 2010/0113980 | A1 | 5/2010 | Herr et al. |
| 2010/0114329 | A1 | 5/2010 | Casler et al. |
| 2010/0286796 | A1 | 11/2010 | Clausen |
| 2010/0324698 | A1 | 12/2010 | Sverrisson et al. |
| 2010/0324699 | A1 | 12/2010 | Herr et al. |
| 2011/0125290 | A1 | 5/2011 | Langlois |
| 2011/0264230 | A1 | 10/2011 | Herr et al. |
| 2012/0010729 | A1 | 1/2012 | Langlois et al. |
| 2012/0083901 | A1 | 4/2012 | Langlois et al. |
| 2012/0283844 | A1 | 11/2012 | Langlois |
| 2013/0095861 | A1 | 4/2013 | Li et al. |
| 2013/0268093 | A1 | 10/2013 | Gilbert et al. |
| 2013/0311133 | A1 | 11/2013 | Kordari et al. |
| 2013/0311134 | A1 | 11/2013 | Kordari et al. |
| 2014/0156025 | A1 | 6/2014 | Bisbee, III et al. |
| 2014/0200680 | A1 | 7/2014 | Holgate et al. |

FOREIGN PATENT DOCUMENTS

| | | |
|---|---|---|
| CN | 1376856 | 10/2002 |
| EP | 0 380 060 | 8/1990 |
| EP | 1792597 A1 | 6/2007 |
| GB | 2 367 753 | 4/2002 |
| JP | 2009/153660 A | 7/2009 |
| WO | WO 93/24080 | 12/1993 |
| WO | WO 94/09727 | 5/1994 |
| WO | WO 00/30572 | 6/2000 |
| WO | WO 00/38599 | 7/2000 |
| WO | WO 01/54630 | 8/2001 |
| WO | WO 2004/017873 | 3/2004 |
| WO | WO 2005/087144 | 9/2005 |
| WO | WO 2005/110293 | 11/2005 |
| WO | WO 2006/083913 | 8/2006 |
| WO | WO 2007/025116 | 3/2007 |
| WO | WO 2007/027668 | 3/2007 |
| WO | WO 2010/027968 | 3/2010 |
| WO | WO 2010/129716 | 11/2010 |
| WO | WO 2010/148134 | 12/2010 |
| WO | WO 2012/006462 | 1/2012 |
| WO | WO 2012/047721 | 4/2012 |
| WO | WO 2012/150500 | 11/2012 |

OTHER PUBLICATIONS

Dejan Popovic et al., Control Aspects of Active Above-Knee Prosthesis, International Journal of Man-Machine Studies, vol. 35, Issue 6, Dec. 1991, at 751 ("Popovic").

James Jay Martin, Electronically Controlled Magnetorheological Fluid Prosthetic Foot, U.S. Appl. No. 60/371,974, filed Apr. 12, 2002.

Joaquin A. Blaya, Force-Controllable Ankle Foot Orthosis (AFO) to Assist Drop Foot Gait, Thesis—Massachusetts Institute of Technology, Dept. of Mechanical Engineering (Jul. 8, 2003) ("Blaya") and corresponding Declaration of Diane Geraci.

Kamiar Aminian et al., Estimation of Speed and Incline of Waling Using Neural Network, IEEE Transactions on Instrumentation and Measurement, vol. 44, No. 3, Jun. 1995, at 743 ("Aminian").

Peter H. Veltink et al., The Feasibility of Posture and Movement Detection by Accelerometry, in 15th Annual International Conference of the IEEE Engineering in Medicine and Biology Society, Oct. 28-31, 1993, San Diego, CA, at 1230-1231 ("Veltink").

Herr, H., A Hybrid Actuator Comprising Motor, Spring, and Variable-Damper Elements, U.S. Appl. No. 60/666,876, filed Mar. 31, 2005.

(56) References Cited

OTHER PUBLICATIONS

Herr, H., An Artificial Ankle-Foot System with Spring, Variable-Damping, and Series-Elastic Actuator Components, U.S. Appl. No. 60/704,517, filed Aug. 1, 2005.
Powered Prosthetic Thigh and Leg, Diginfonews, Nov. 7, 2008, <URL:http://www.youtube.com/watch?v=lqjtTzNEd54&feature=youtu.be>.
International Search Report dated Jun. 7, 2013, issued in connection with International Application No. PCT/US2013/033937.
Dietl et al., "Der Einsatz von Elektronik bei Prothesen zur Versorgung der unteren Extremität," Med. Orth. Tech., vol. 117, 1997, pp. 31-35.
Office Action in Canadian Patent Application No. 2,762,265 dated Nov. 14, 2013.
Office Action in Canadian Patent Application No. 2559890, dated Aug. 25, 2011.
Office Action in Canadian Patent Application No. 2559890, dated Jun. 11, 2012.
Office Action in Chinese Patent Application No. 200580014676.5, dated Nov. 6, 2009.
Office Action in European Patent Application No. 05725431, dated Sep. 23, 2010 in 5 pages.
Invitation to Pay Fees and Partial International Search Report in International Application No. PCT/US2005/008243, dated Jul. 22, 2005.
International Search Report in International Application No. PCT/US2005/008243, dated Oct. 10, 2005 in 5 pages.
International Preliminary Report on Patentability and Written Opinion in International Application No. PCT/US2005/008243, dated Sep. 21, 2006 in 10 pages.
Official Communication in Canadian Application No. 2595895, dated Aug. 22, 2013.
Official Communication in Canadian Application No. 2595895, dated Apr. 24, 2014.
Official Communication in European Application No. 06748179.6, dated Apr. 4, 2013.
Notice of Allowance in Chinese Application No. 200680039509, dated Dec. 28, 2012.
Official Communication in European Application No. 06802543.6, dated Sep. 24, 2013.
Official Communication in European Application No. 06802543.6, dated Jun. 2, 2014.
International Search Report and Written Opinion in PCT Application No. PCT/US2006/0033658, mailed May 11, 2007.
International Search Report and Written Opinion in PCT Application No. PCT/US2011/054043, dated Jan. 26, 2012.
International Preliminary Report on Patentability and Written Opinion in PCT Application No. PCT/US2011/054043, dated Apr. 2, 2013.
International Search Report and Written Opinion in PCT Application No. PCT/US2011/043246, dated Nov. 21, 2011.
International Preliminary Report on Patentability and Written Opinion in PCT Application No. PCT/US2011/043246, dated Jan. 8, 2013.
Official Communication in Canadian Application No. 2,673,399, dated Apr. 14, 2014.
Official Communication in European Application No. 08706257.6, dated Nov. 5, 2013.
International Search Report and Written Opinion in Application No. PCT/IB2012/000998, dated Sep. 11, 2012.
International Preliminary Report on Patentability in Application No. PCT/IB2012/000998, dated Nov. 14, 2013.

\* cited by examiner

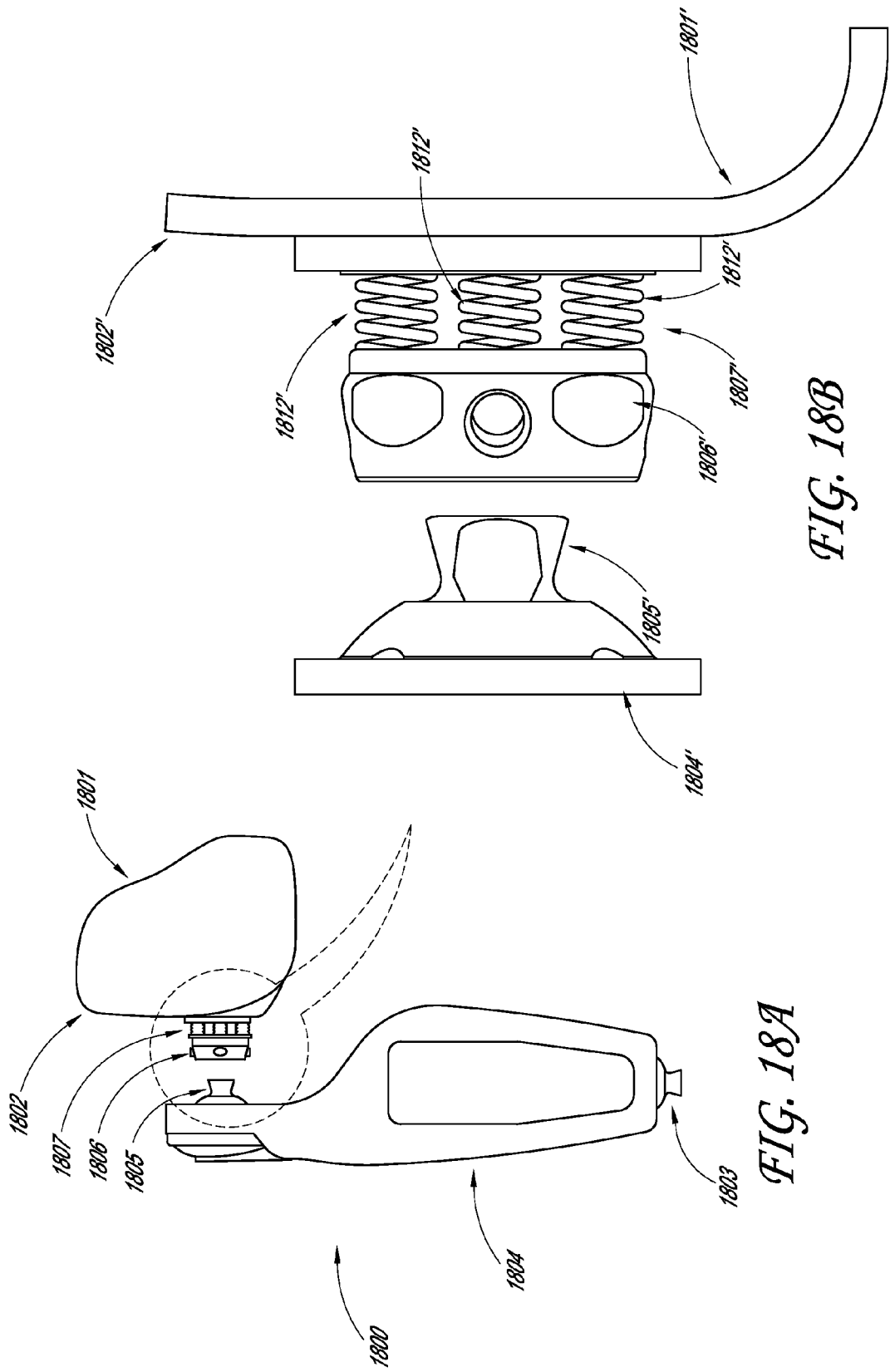

POWERED PROSTHETIC HIP JOINT

CROSS-REFERENCE TO RELATED APPLICATION

This application claims the benefit of U.S. Provisional Patent Application No. 61/617,540, entitled POWERED PROSTHETIC HIP JOINT, and filed Mar. 29, 2012, the entire contents of which are incorporated herein by reference.

BACKGROUND

1. Field

Certain embodiments of the present invention are directed to a prosthetic hip joint, and more particularly to a microprocessor controlled prosthetic hip joint.

2. Description of the Related Art

The occurrence of hip-disarticulation amputations is increasing due to, among other reasons, various armed conflicts. A very limited number of products are available to address this type of amputation by providing some basic function allowing the amputee to stand and walk. Of the products that are currently available, they mainly consist of two types: passive mechanical linkages and hydraulic augmented mechanical linkages.

Passive mechanical linkage hip joints are designed to provide basic support in stance phase, without allowing much swing phase hip motion to occur. However, lack of swing phase motion has been observed to greatly affect the mobility of the user. In most cases, this type of joint allows the user to sit through the use of a spring or elastic member in order for the prosthetic component to clear the socket's distal area that is used while seated.

The hydraulic augmented mechanical linkage type of hip joint provides additional features related to stance and swing motion control. In stance phase, the knee can dampen the motion created by the interaction of the prosthetic foot with the ground (i.e., hip extension) such that gradual rollover is obtained. In turn, during swing phase, the hydraulics can be used in combination with a spring or elastic to control the hip flexion velocity and terminal swing hip flexion angle. However, the stance control employed by hydraulic augmented mechanical hip joints does not allow for stable hip positioning while standing. This results in the user standing in the maximally extended hip position, which has been observed to affect the user's postural stability and cause significant gait deviation when transitioning from static standing to an ambulatory task (e.g., walking). Furthermore, though the combination of the hydraulic damper with the spring or elastic in swing phase allows the user to generate some hip-flexion dynamics, significant effort is required from the user, in the form of pelvic rotation, in order to generate sufficient swing dynamics to place the hip joint in the correct position for the following foot strike.

Accordingly, there is a need for an improved prosthetic hip joint that solves some of the problems noted above and allows for proper stance phase control (in standing and walking) and provides a more natural hip joint movement.

SUMMARY

In accordance with one embodiment, a powered prosthetic hip joint is provided. The powered prosthetic hip joint can comprise a proximal portion removably coupleable to a prosthetic socket attached to a portion of an amputee's body, such as a hip, a residual limb, a trunk, and/or a pelvic area. The prosthetic hip joint also can comprise a distal portion attached to the proximal portion and defining a prosthetic thigh portion, the distal portion having a distal connector configured to removably couple to a prosthetic knee. Most of the embodiments described herein can be configured for use with a prosthetic socket attached to a portion of an amputee's body, such as a hip, a residual limb, a trunk, and/or a pelvic area, although some of the embodiments do not include a prosthetic socket. Some embodiments are described in the context of a hip socket, although the embodiments can be used with other types of sockets.

Several embodiments include a computer controlled actuator. The computer that controls the actuator can be located remotely from the prosthetic hip, near the prosthetic hip, coupled to the prosthetic hip, and/or in a portion of the prosthetic hip. In some embodiments, the computer that controls the actuator is located in another prosthetic member such as a prosthetic knee assembly, a prosthetic foot assembly, a prosthetic ankle assembly and/or a prosthetic lower leg portion between a knee and an ankle.

In some embodiments, a computer controlled actuator is disposed in the prosthetic thigh portion, and the actuator is configured to rotate the distal portion along a sagittal plane between an extension angle of about $-20°$ relative to a vertical axis and a flexion angle of about $120°$ relative to the vertical axis during one or more activities such as ambulation and/or sitting. In one embodiment, the actuator rotates the distal portion relative to the proximal portion. In another embodiment, the actuator rotates the distal portion relative to the socket.

In several embodiments, a computer controlled actuator is disposed in the hip area, a socket area, and/or in the hip joint. The actuator can be a linear actuator and/or a rotary actuator. Several embodiments include a computer controlled actuator disposed in a pelvis segment and the actuator is configured to rotate the distal portion along a sagittal plane between an extension angle of about $-20°$ relative to a vertical axis and a flexion angle of about $120°$ relative to the vertical axis to accommodate user activities, such as ambulation and sitting. The user might not use this full range of motion during all activities, as many activities do not require this full range of motion.

Some embodiments include a linear actuator and a rotary actuator, which are used to rotate a prosthetic hip joint. In several embodiments, a rotary actuator is primarily used to rotate a hip joint while a linear actuator is used to change the rotational plane of the rotary actuator. This configuration helps simulate the degrees of freedom provided by a natural hip due to the head of a natural femur and the socket of a natural hip.

In accordance with another embodiment, a powered prosthetic hip joint is provided allowing for a flexible connection of the upper thigh segment to the socket, such that frontal plane rotation is achieved for improved user comfort and fulfillment of the natural abduction-adduction motion of the non-pathological hip joint. Relative rotation of the hip prosthetic proximal end with respect to the socket system in the frontal plane is achieved using a compliant mechanical structure, which deflects when load is transferred to the ground from the socket, such as observed during stance phase of walking or when shifting weight from one lower-limb to the other while standing. The compliant mechanical structure can be a compliant component, compliant linkage, and/or a compliant connector.

In accordance with another embodiment, a dual joint prosthetic device is provided allowing the device to replace lost function at the hip and knee levels. This embodiment allows synchronized operation of both joints through the use of a two-degree of freedom central controller and can improve the device's capacity to restore natural gait for locomotion activities most often encountered in daily living. Several embodiments of dual joint prosthetic devices use a powered proximal joint (i.e., hip joint), coupled with either a second powered joint on the distal end (i.e., knee joint) or a passive stance controllable device.

Some embodiments also include a prosthetic ankle joint. Several embodiments include a control system that enables synchronized and/or coordinated control of a hip joint, a knee joint, and an ankle joint. Some of the joints may be powered while others may be passive. In some embodiments, the prosthetic leg includes a powered hip joint, a powered knee joint, and a powered ankle joint, wherein the movement of all three joints can be coordinated.

In accordance with another embodiment, a method of operating a powered prosthetic hip joint is provided. The method can comprise sensing if the prosthetic foot is in contact with a ground surface or not in contact with the ground surface. The method can also comprise operating an actuator of the powered prosthetic hip joint to provide resistance to movement between the components of the hip joint, thereby increasing a stiffness of the hip joint if the prosthetic foot is in contact with the ground surface. The method can also comprise operating the actuator of the powered prosthetic hip joint to decrease a stiffness of the hip joint if the prosthetic foot is not in contact with the ground surface.

In accordance with another embodiment, a method of operating a powered prosthetic hip joint is provided. The method can comprise sensing if the prosthetic foot is in contact with a ground surface or not in contact with the ground surface. The method can also comprise operating an actuator of the powered prosthetic hip joint to provide resistance to movement between the components of the hip joint, thereby increasing an apparent and/or effective stiffness of the hip joint if the prosthetic foot is in contact with the ground surface. The method can also comprise operating the actuator of the powered prosthetic hip joint to decrease an apparent and/or effective stiffness of the hip joint if the prosthetic foot is not in contact with the ground surface. In this application, apparent stiffness is the rotational stiffness perceived by a typical, average user of the prosthetic hip. For example, a prosthetic hip with a higher apparent stiffness will typically feel less prone to hip rotation than a hip with lower apparent stiffness. In this application, effective stiffness includes all factors that influence the force required to rotate a joint. For example, damping characteristics and inertia influence effective stiffness.

In accordance with another embodiment, a method of operating a powered prosthetic hip joint is provided. The method can comprise sensing if the prosthetic foot is in contact with a ground surface or not in contact with the ground surface. The method can also comprise operating an actuator of the powered prosthetic hip joint to provide resistance to movement of the hip joint if the prosthetic foot is in contact with the ground surface. The method can also comprise operating the actuator of the powered prosthetic hip joint to decrease resistance to movement of the hip joint if the prosthetic foot is not in contact with the ground surface.

In accordance with another embodiment, a method of operating a powered prosthetic hip joint is provided. The method can comprise sensing if the prosthetic foot is in contact with a ground surface or not in contact with the ground surface. The method can also comprise operating an actuator of the powered prosthetic hip joint to a higher resistance to movement of the hip joint if the prosthetic foot is in contact with the ground surface than if the prosthetic foot is not in contact with the ground surface.

In accordance with another embodiment, a method of operating a powered prosthetic hip assembly is provided. The method can comprise sensing if the prosthetic foot is in contact with a ground surface or not in contact with the ground surface. The prosthetic hip assembly can be configured to provide a high resistance mode and a low resistance mode, wherein the high resistance mode provides higher resistance to movement of a prosthetic hip joint than the low resistance mode provides. In some embodiments, the low resistance mode provides no resistance and/or minimal resistance to movement of the prosthetic hip joint. The method can also comprise operating an actuator of the powered hip assembly such that the prosthetic hip assembly provides the high resistance mode during at least a portion of a stance phase. The method can also comprise operating an actuator of the powered hip assembly such that the prosthetic hip assembly provides the low resistance mode during at least a portion of a swing phase.

In some method embodiments with a high resistance mode and a low resistance mode, the method can comprise operating an actuator of the powered prosthetic hip joint to provide the high resistance mode during at least a portion of the time the prosthetic foot is in contact with the ground surface. The method can also comprise operating an actuator of the powered prosthetic hip joint to provide the low resistance mode during at least a portion of the time the prosthetic foot is not in contact with the ground surface.

In several method embodiments, the actuator can be configured to rotate the prosthetic hip joint along a sagittal plane between an extension angle of about −20° relative to a vertical axis and a flexion angle of about 120° relative to the vertical axis during several types of ambulation. Some activities require less hip extension and/or flexion. In some embodiments, the actuator is configured to rotate the prosthetic hip joint to provide about 40 degrees of flexion, about 50 degrees of flexion, and/or about 60 degrees of flexion during walking. Some embodiments are configured to provide a flexion angle up to about 120° relative to the vertical axis to enable sitting.

In some embodiments, a powered prosthetic thigh comprises a proximal portion configured to couple to a prosthetic socket attached to an amputee's hip and a distal portion attached to the proximal portion. The distal portion can comprise a distal connector configured to couple to a prosthetic knee. The powered prosthetic thigh can comprise a computer controlled actuator. The actuator can be configured to rotate the prosthetic thigh along a sagittal plane and in other directions relative to the prosthetic socket attached to the amputee's hip. The powered prosthetic thigh can also comprise a proximal connector coupled to the proximal portion, wherein the proximal connector is configured to couple the proximal portion to the prosthetic socket, and the actuator is configured to rotate the proximal connector relative to the proximal portion.

In some embodiments, the actuator comprises a motor and a transmission. The motor can be located distally from the proximal connector. The motor can be operatively coupled to the proximal connector by one or more gears, belts, and/or chains. The transmission can be mounted collinearly and/or coaxially with the proximal connector. The motor can be mounted collinearly and/or coaxially with the proximal connector. The motor can be mounted collinearly and/or coaxially with the transmission. The actuator can comprise a hydraulic pump, and the transmission can comprise a hydraulic transmission system.

In several embodiments, a powered prosthetic thigh comprises a proximal portion configured to couple to a prosthetic socket attached to an amputee's hip and a proximal connector coupled to the proximal portion. The proximal connector can be configured to couple the proximal portion to the prosthetic socket. The powered prosthetic thigh can also comprise a first actuator configured to rotate the proximal connector relative to the proximal portion, wherein the first actuator is configured to provide a torque that moves the proximal portion relative to the prosthetic socket. The powered prosthetic thigh can also comprise a distal portion coupled to the proximal portion, a distal connector coupled to the distal portion, and a second actuator configured to influence the rotation of the distal connector relative to the distal portion. In some embodiments, the second actuator can influence the rotation by resisting the rotation of the distal connector relative to the distal portion. In some embodiments, the second actuator can influence the rotation by causing the rotation of the distal connector relative to the distal portion by providing a torque that causes the rotation.

In several embodiments, a powered prosthetic thigh comprises a motor, wherein the motor is configured to drive the first actuator and the second actuator. Is some embodiments, the second actuator is a passive actuator. The second actuator can comprise a magnetorheological actuator. The second actuator can comprise a hydraulic actuator.

In several embodiments, the second actuator can be configured to rotate the distal connector relative to the distal portion. The second actuator can be configured to power movement of the distal connector relative to the distal portion.

The powered prosthetic thigh can comprise a computer controller and at least one sensor. The computer controller can be configured to use signals from the sensor to synchronize and/or coordinate operation of the first actuator and the second actuator.

The powered prosthetic thigh can comprise a compliant transmission, wherein the compliant transmission couples the distal connector and the distal portion. The compliant transmission can be configured such that relative rotation between the distal connector and the distal portion stores or releases mechanical energy and/or potential energy. The compliant transmission can comprise at least one spring and/or a rubber material.

In some embodiments, a powered prosthetic thigh comprises a distance between the proximal connector and the distal connector. A variable length thigh segment can be coupled between the proximal connector and the distal connector, wherein the variable length thigh segment is configured to adjust the distance between the proximal connector and the distal connector. The variable length thigh segment can comprise a pylon.

In some embodiments, a prosthetic hip comprises a prosthetic socket configured to be attached to an amputee, a powered prosthetic thigh, and a connector pivotably coupling the prosthetic socket and the powered prosthetic thigh. Items can be pivotably coupled via a ball joint and/or another joint that allows movement in one or more planes. The powered prosthetic thigh can comprise a proximal portion; a distal portion attached to the proximal portion, wherein the distal portion comprises a distal connector configured to couple to a prosthetic knee; and a computer controlled actuator, wherein the actuator is configured to rotate the powered prosthetic thigh along a sagittal plane relative to the prosthetic socket.

In some embodiments, the connector comprises a compliant member configured to deform, wherein deformation of the compliant member allows relative motion between the prosthetic socket and the powered prosthetic thigh. The compliant member can comprise at least one spring located between a portion of the prosthetic socket and a portion of the powered prosthetic thigh.

The connector can comprise an attachment arm that pivotably couples the prosthetic socket and the powered prosthetic thigh, wherein the prosthetic socket comprises a front wall, and the attachment arm is pivotably coupled to the front wall. The prosthetic socket can comprise a front wall and the connector can comprise an attachment arm with a first portion and a second portion, wherein the first portion is coupled to the powered prosthetic thigh and the second portion is pivotably coupled to the front wall. The prosthetic hip can be configured to allow the powered prosthetic thigh to move from underneath the prosthetic socket to enable a sitting mode. The prosthetic hip can comprise a lock configurable to prevent the attachment arm from pivoting relative to the prosthetic socket.

In several embodiments, a method for operating a powered prosthetic hip joint operatively coupled to a prosthetic foot comprises determining if the prosthetic foot is in contact with a ground surface and operating an actuator of the powered prosthetic hip joint to increase a stiffness of the hip joint if the prosthetic foot is in contact with the ground surface. The method can also comprise operating the actuator of the powered prosthetic hip joint to decrease the stiffness of the hip joint if the prosthetic foot is not in contact with the ground surface.

The method can also comprise an actuator that is configured to rotate the prosthetic hip joint along a sagittal plane during ambulation. The actuator can be configured to rotate the prosthetic hip joint along the sagittal plane between an extension angle of about −20° relative to a vertical axis and a flexion angle of about 120° relative to the vertical axis. The actuator can comprise a motorized hip joint actuator configured to power flexion motion. The method can further comprise rotating the prosthetic hip joint with the actuator along the sagittal plane between an extension angle of about −20° relative to a vertical axis and a flexion angle of about 120° relative to the vertical axis. Determining if the prosthetic foot is in contact with the ground surface can comprise detecting a load on a ground contact sensor disposed on the prosthetic hip joint. The method can comprise operating the actuator when the prosthetic foot is in contact with the ground surface and in a standing phase of gait so that the prosthetic hip joint is positioned in a neutral position generally aligned with a vertical axis.

BRIEF DESCRIPTION OF THE DRAWINGS

FIGS. 18*a* and 18*b* are schematic front views of prosthetic hip joint embodiments attached to a side of a socket through the use of compliant component embodiments.

DETAILED DESCRIPTION

Figure 1A:
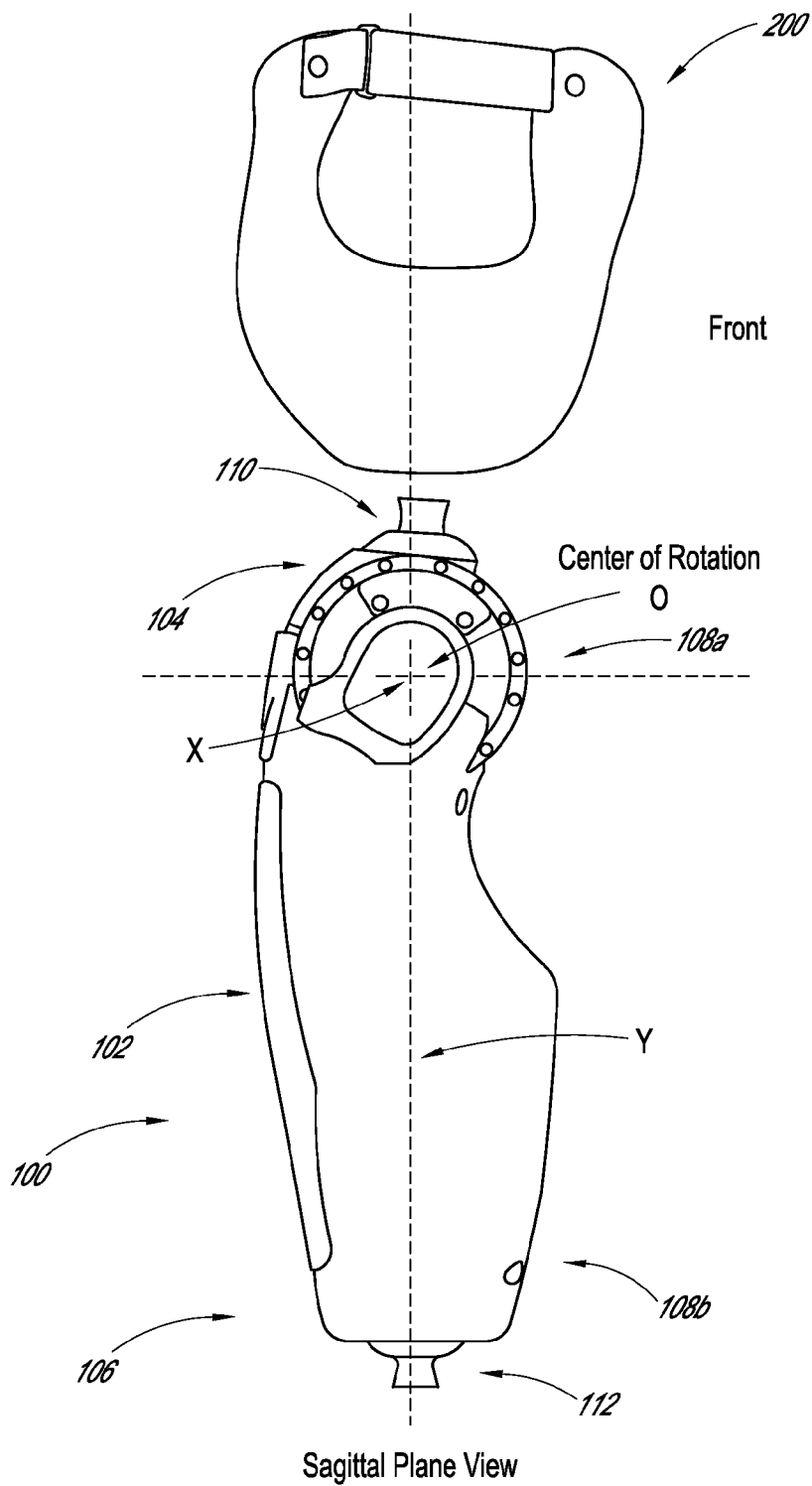
FIG. 1a is a schematic side view of one embodiment of a prosthetic hip joint and a sagittal view of a prosthetic hip joint socket.
Figure 1B:
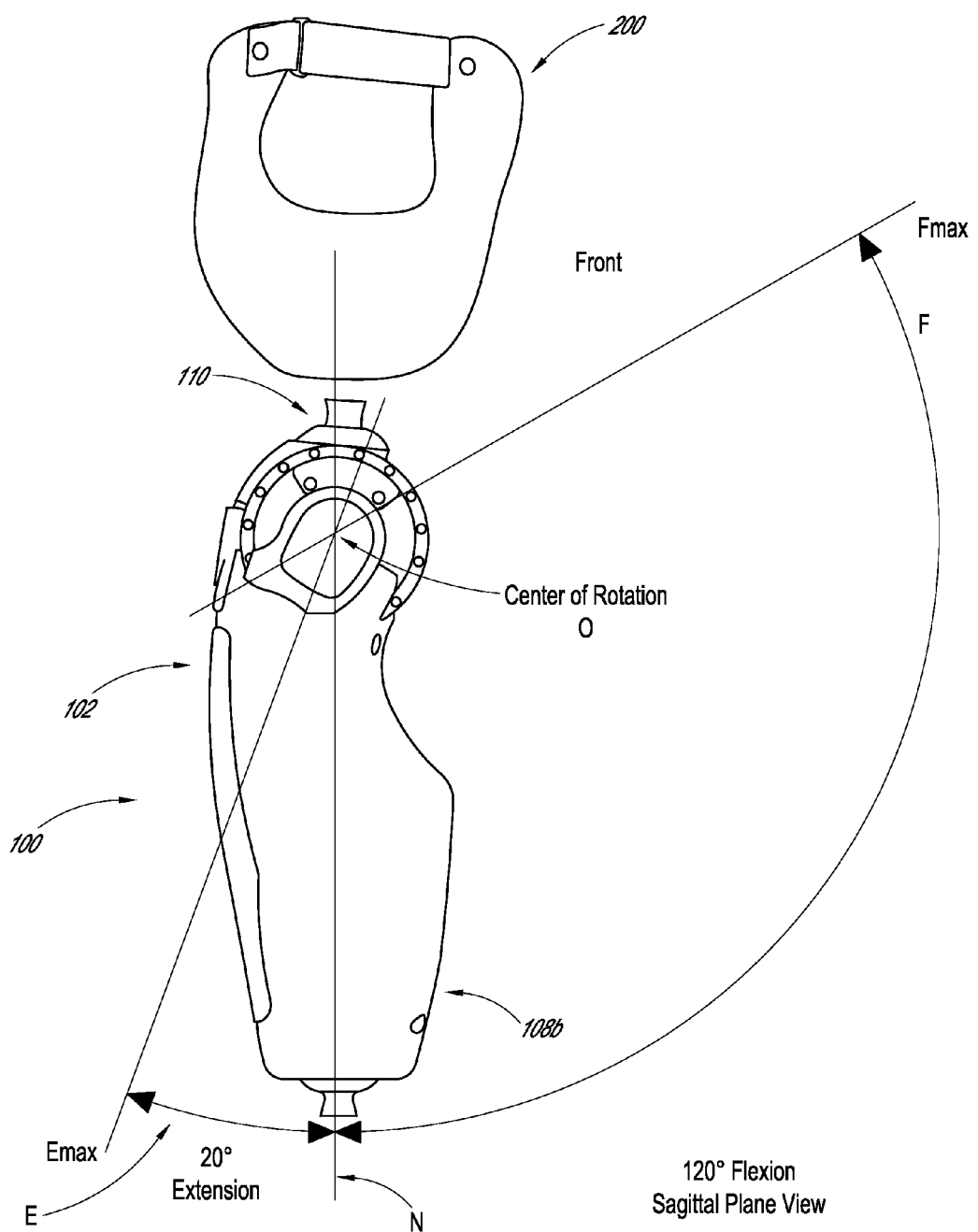
FIG. 1b is a schematic side view of the prosthetic hip joint of FIG. 1a showing an embodiment of the range of motion of the joint.

FIGS. 1*a* and 1*b* show one embodiment of a powered hip joint 100 of a prosthetic hip joint system. The powered hip joint 100 can have an elongated body 102 that extends between a proximal end 104 and a distal end 106, and can have a first connector 110 at the proximal end 104 and a second connector 112 at the distal end 106. In the illustrated embodiment, the first connector 110 can be a male pyramid connector and connect to a corresponding connector in distal end of a prosthetic component, such as a distal end of a prosthetic socket 200.

In some embodiments, the socket 200 is an envelope type socket that fits over a portion of an amputee's body, such as a pelvic area. Several embodiments include a socket that fits over a short stump, including a stump in the hip area. The socket 200 can have a connector to couple the socket 200 to the powered hip joint 100.

Several embodiments do not require a connector between the socket 200 and the powered hip joint 100. The socket 200 may be permanently coupled to the powered hip joint 100. The socket 200 may be coupled to the powered hip joint 100 by a connector type connection and/or by a direct interface, which can be supported by the integration of a lamination adapter that predefines the shape of the socket required for a permanent prosthetic device to socket connection (e.g., bolted joint). The lamination adapter can be an L-shaped plate when viewed in the frontal plane where the lateral section includes a feature to be directly connected to the hip joint.

The powered hip joint can be attached to the skeletal structure of the user via suitable coupling devices. In some embodiments, the socket is similar to an acetabular cup that replaces a natural hip socket.

In another embodiment, the first connector 110 can be a female connector. Similarly, the second connector 112 can be a male pyramid connector that can removably couple to another prosthetic component, such as a prosthetic knee. In another embodiment, the second connector 112 can be a female connector. In some embodiments (not shown), the prosthetic hip joint 100 moves relative to the socket 200 when the amputee sits down such that the amputee does not sit on the hip joint 100.

With reference to FIG. 1*a*, the powered hip joint 100 can have a proximal portion 108*a*, or actuator, that is pivotally coupled to a distal portion 108*b*, or thigh portion, of the elongated body 102 about an axis X, where the axis extends into the page in FIG. 1*a*. In several embodiments, the longitudinal axis X defines a center of rotation O that is disposed along a longitudinal axis Y of the powered hip joint 100. The elongated body 102 can house the actuator (e.g., an electric motor) and electronics, including a computer processor that controls the actuation of the motor. In some embodiments, the actuator is disposed, located, and/or housed in other parts of the prosthetic device. For example, the actuator can be disposed in the proximal portion 108*a*. In several embodiments, the actuator is a rotary actuator disposed in a hip joint assembly.

The motor is operated to vary the angle between an axis Z (e.g., central axis or axis of symmetry) defined by the proximal connector 110 and the longitudinal axis Y of the body 102 to change the orientation of the powered hip joint 100. In some embodiments, the axis Z of the first connector 110 and the longitudinal axis Y of the body 102 are generally co-linear when the hip joint 100 is in a neutral position N (e.g., when the user is standing or in a stance position). In several embodiments, the motor is operated to rotate the hip joint in a manner that simulates the natural hip motion of a healthy hip joint.

As shown in FIG. 1b, the powered hip joint 100 can move toward extension E or flexion F along the sagittal plane from the neutral position N. In some embodiments, the powered hip joint 100 can move to a maximum extension angle $E_{max}$ of about 20° relative to the neutral position N. However, in other embodiments, the maximum extension angle $E_{max}$ can be less than or greater than 20°. In several embodiments, the powered hip joint 100 can move to a maximum flexion angle $F_{max}$ of about 120° relative to the neutral position N. However, in other embodiments, the maximum flexion $F_{max}$ angle can be less than or greater than 120°.

Several embodiments include motion in planes and directions other than the sagittal plane. Movement can include outward movement, medial-lateral movement, and ball-joint movement. For example, some embodiments enable the prosthetic hip joint to move such that the distal portion 108b moves in a circular path rather than only moving in an arc. This movement capability allows users to step sideways and to move their prosthetic knee away from their natural knee.

Figure 2:
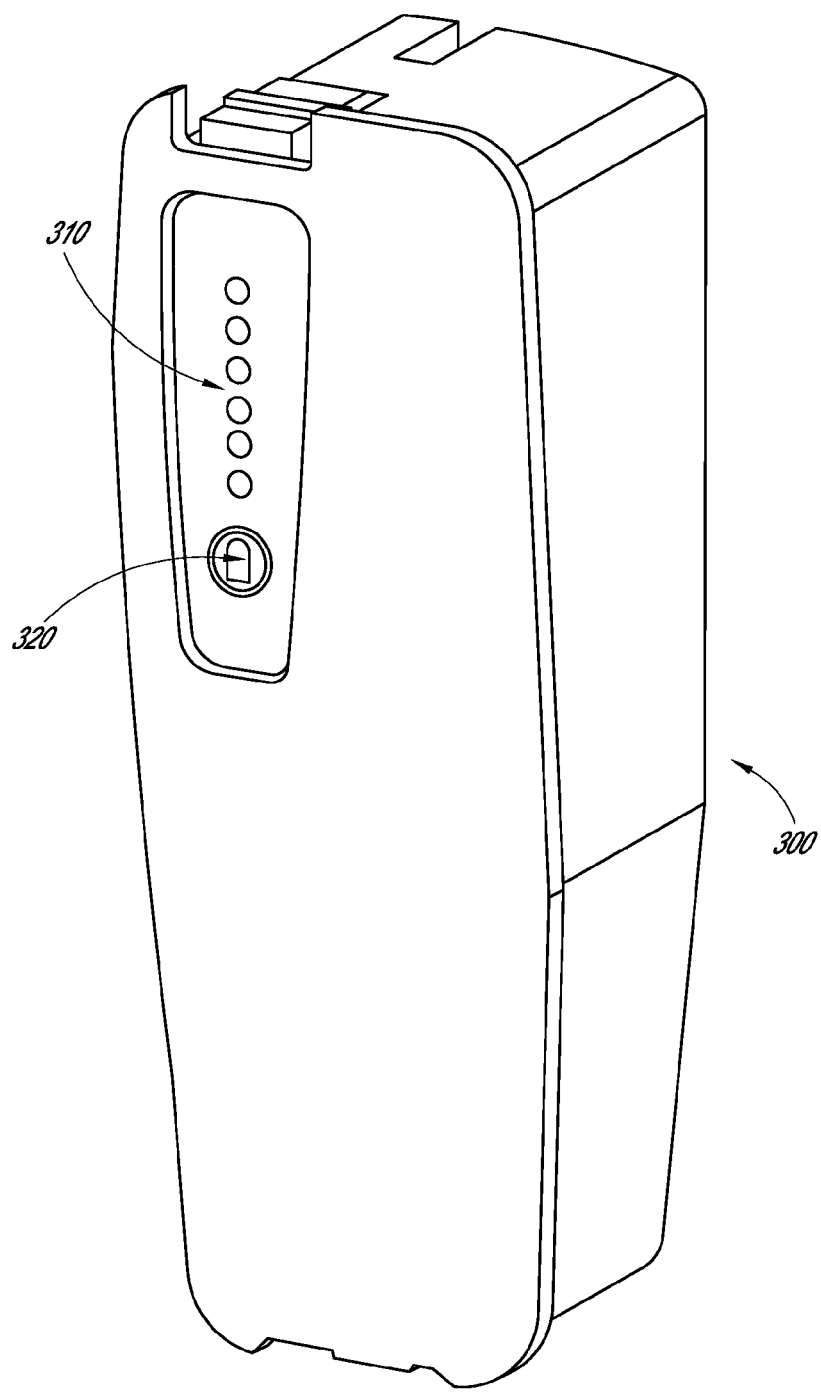
FIG. 2 is a schematic perspective view of one embodiment of a battery pack for a prosthetic hip joint.
Figure 3:
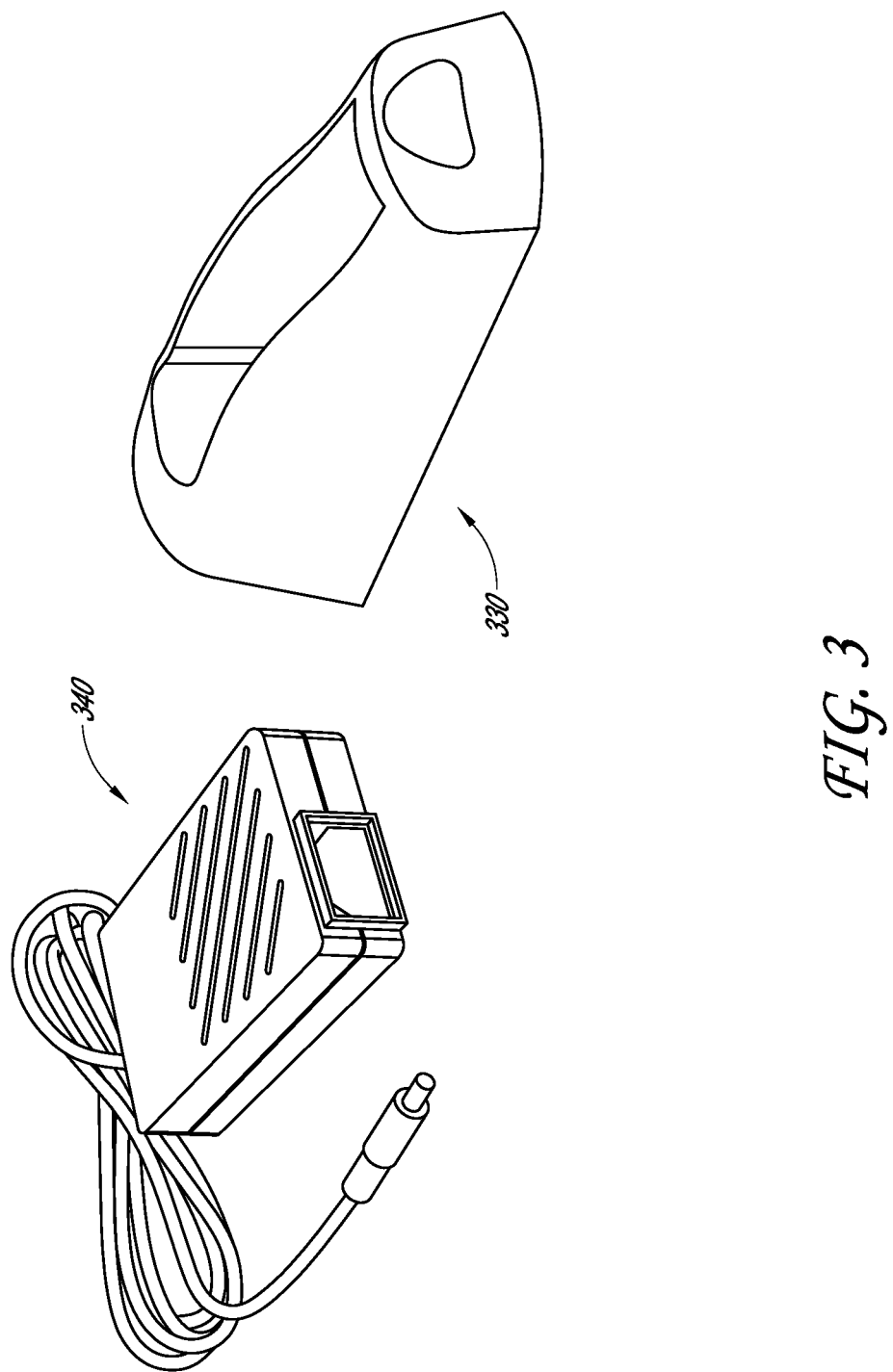
FIG. 3 is a schematic perspective view of one embodiment of a battery charger and its power supply that can be used with the battery pack of FIG. 2.

Referring now to FIGS. 1b and 2, the prosthetic hip joint system can also include a battery pack 300 that provides power to the powered hip joint 100. The battery pack 300 can have battery status LEDs 310 and a battery status button 320. In some embodiments, the battery pack 300 is removable and configured to fit within a recess (not shown) in the body 102 of the powered hip joint 100. As shown in FIG. 3, the prosthetic hip system can also include a dock-in charger 330 that removably receives the battery pack 300 therein and a power supply 340 that attaches to the charger 330 to provide power to the charger 330 (e.g., from a wall outlet) to charge the battery pack 300. In some embodiments, the prosthetic hip system can also include a lamination adapter (not shown) for the socket 200 in order to reinforce the construction of the socket 200 and ensure the connector of the socket 200 is configured properly and provides the needed strength to receive the prosthetic hip joint 100. In several embodiments, the lamination adapter can be made of aluminum. However, in other embodiments, the lamination adapter can be made of other suitable materials.

In some embodiments, the powered hip joint 100 can have a similar structure as the joint mechanism 10 described in US Patent Application Publication No. 2009/0299480, though the implementation of the powered hip joint 100 differs from the knee joint 10 in U.S. Patent Application Publication No. 2009/0299480. For example, while the knee joint 10 is configured to allow for flexion motion only and is mechanically limited to a maximum extension angle of 0° (i.e., fully extended knee), the powered hip joint 100 allows for a maximum extension of approximately −20° (i.e., 20° extended relative to the neutral position N), as discussed above. U.S. Patent Application Publication No. 2009/0299480 is incorporated herein by reference and should be considered a part of this specification.

With reference to FIGS. 1a and 1b, the powered hip joint 100 can have an actuator that includes an electric motor (not shown), such as a brushless DC motor (available, for example, from Allied Motion Emoteq) axially mounted to a gear mechanism, such as a harmonic drive (available, for example, from Harmonic Drives Inc). In some embodiments, the stator of the brushless motor can be operationally fixed to the amputee's socket, which in turn is operationally coupled to the amputee and surrounding tissues. The rotor of the brushless motor can be coupled to a harmonic drive wave generator (not shown), which turns under motor power with respect to a harmonic drive circular spline, operatively connected to the stator of the motor. Relative motion of the harmonic drive wave generator with respect to the circular spline can generate rotational motion of a harmonic drive flexible spline, hence causing rotation of the actuator output, herein referred to as the output lever. The output lever is coupled to a compliant element, which in turn is coupled to the elongated body 102, which herein plays the role of the human thigh bone. Such a harmonic transmission assembly is similar to the harmonic transmission assembly 56 illustrated in FIG. 3 of US Patent Application Publication No. 2009/0299480 and described in that application.

The net torque between the actuator output and the distal portion 108b, including contributions arising from the interaction of the prosthetic foot, shank, and prosthetic knee components with the environment in which the user is ambulating, can be measured through the deflection of a serial compliant element. In some embodiments, the prosthetic hip assembly senses and/or approximates the net torque via a deflection measurement of a portion of the prosthetic device, the serial compliant element, and/or of a compliant connector. The prosthetic hip assembly's control system can use the deflection measurement to determine appropriate actuator behavior. Additionally, the presence of a spring element in series with the actuator output also allows for generation of a passive compliance in the hip joint, which advantageously reduces shocks and smooths out an acceleration pattern arising from application of external loads.

With continued reference to FIGS. 1a and 1b, the powered hip joint 100 can have a ground contact sensor disposed in the distal end 106 of the distal portion 108b, which allows for static measurement of the interaction between the prosthetic lower-limb and the ground. In some embodiments, the specific sensor design allows for selective compliance, which allows for measuring axial loads affecting the hip joint 100 without being affected by inertial loads or torque loads experienced through the interaction between components or swing phase acceleration patterns. Further details on such ground contact sensors are provided in U.S. Patent Application Publication No. 2012/0010729, which is incorporated herein by reference and should be considered a part of this specification.

Figure 4A:
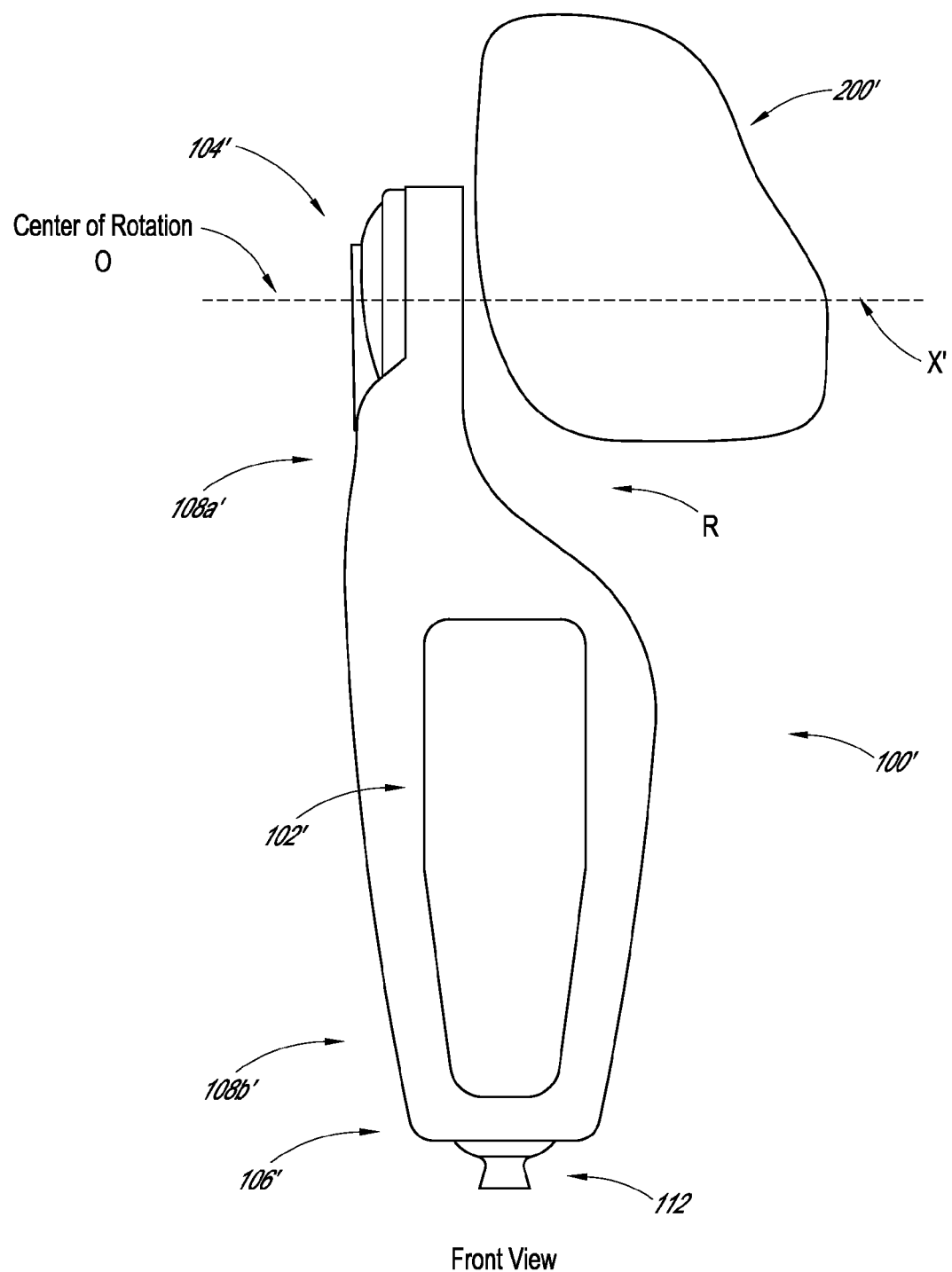
FIG. 4a is a schematic front view of another embodiment of a prosthetic hip joint attached to a side of one embodiment of a socket.

FIG. 4a shows another embodiment of a powered hip joint 100'. The powered hip joint 100' is similar to the powered hip joint 100 described previously, except as noted below. Thus, the reference numerals used to designate the various components of the powered hip joint 100' are identical to those used for identifying the corresponding components of the powered hip joint 100 in FIGS. 1a and 1b, except that a "'" has been added to several reference numerals.

In the illustrated embodiment, the powered hip joint 100' is laterally coupled to a side of the socket 200', where the proximal portion 108a' of the body 102' defines a recess R' into which at least a portion of the socket 200' extends. The hip joint 100' can include a proximal end 104', a distal portion 108b', a distal end 106', a second connector 112', and a longitudinal axis X'.

In some embodiments, the powered hip joint 100' is coupled to the lateral side of the socket 200' so that the hip joint 100' rotates out of the way when the user sits down such that the user sits on the socket 200' but not the joint 100'. In several embodiments, the powered hip joint 100, 100' has one or more sensors that sense when a user is moving toward a sitting position, and the computer controller operates the actuator to rotate out of the way. The hip joint 100' can be coupled to the socket 200' via a connector that extends from a side of the proximal portion 108a' of the body 102'. In some embodiments, the powered hip joint 100' can increase the range of locomotion activities accessible to the amputee.

Several embodiments include a sitting mode. In some sitting mode embodiments, the hip joint 100' rotates out of the way when the user sits down such that the user sits on the socket 200' but not on the joint 100'. When the hip assembly, controller, and/or the prosthetic assembly detects a transition to sitting down, the hip assembly provides dissipative support to the user. For example, the hip assembly can provide dissipative support and/or a controlled descent as the user transitions from standing to sitting and/or from walking to sitting. This configuration and/or process helps the user to enter a seated position. Sensors can be used to detect the transition from a standing and/or upright position to a seated position before the user actually sits down. The sensors can include accelerometers, joint rotation sensors, proximity sensors, and contact sensors.

In some embodiments, once a prosthetic device detects that a user is attempting to sit down, wants to sit down, and/or is in the process of sitting down, the prosthetic device provides a powered rotation of the hip to facilitate sitting. This powered rotation of the hip can include the hip joint 100' rotating out of the way when the user sits down such that the user sits on the socket 200' but not on the joint 100'. In some embodiments, a powered rotation is replaced with a damping adjustment and/or rotational stiffness reduction that facilitates the user entering a seated position.

Figure 4B:
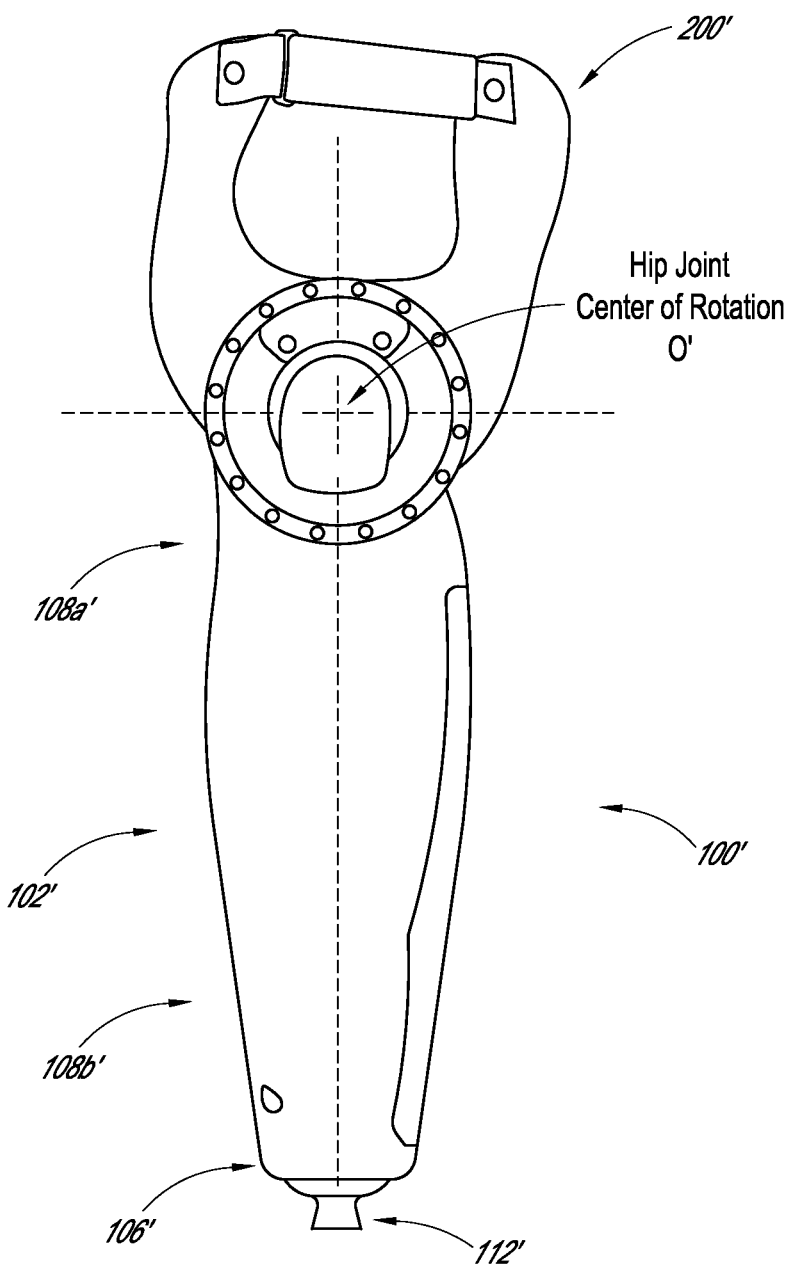
FIG. 4b is a schematic side view of the prosthetic hip joint embodiment of FIG. 4a attached to a side of one embodiment of a socket.

FIG. 4b shows a side view of the same mechanical embodiment of the hip prosthesis shown in FIG. 4a. As can be observed, use of the lateral socket connection can allow for locating the hip prosthesis center of rotation O' in a location corresponding to the generally recognized normal hip center of rotation (i.e., greater trochanter anatomical area). This feature of the lateral socket connection hip prosthesis can allow the prosthetic system to reproduce normal human gait more closely than is possible in some other embodiments, while also allowing the use of the powered hip prosthesis to actively support sitting-down and standing-up activities. Several other embodiments described herein also enable reproducing normal human gait.

Figure 5:
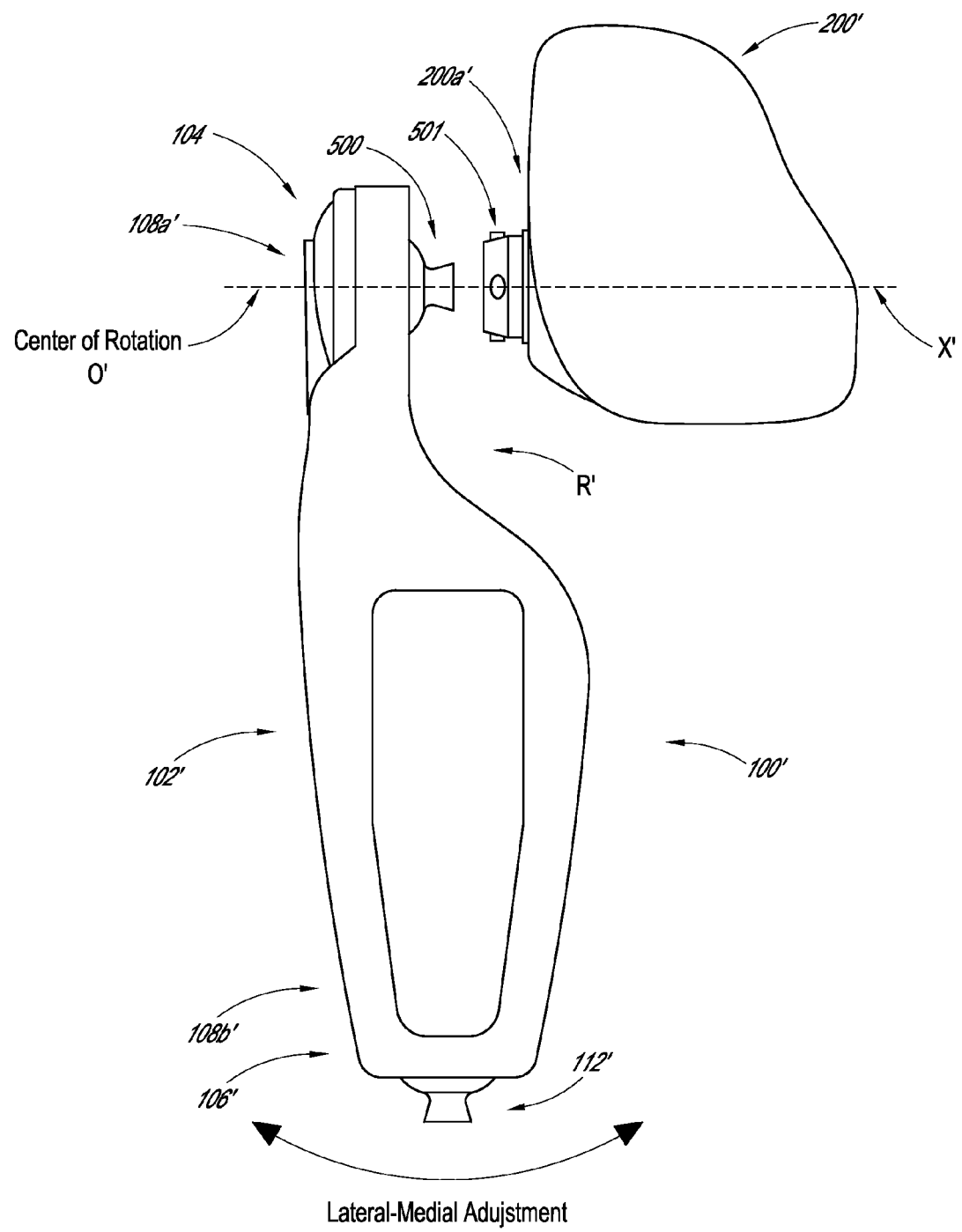
FIG. 5 is a schematic front view of a prosthetic hip joint embodiment coupleable to a side of one embodiment of a socket.

FIG. 5 presents a mechanical embodiment similar to the embodiment previously described in FIGS. 4a and 4b, but where a standard prosthetic pyramidal connector 500 is used to connect the hip prosthesis proximal portion 108a' to the lateral wall 200a' of the socket 200', which is equipped with a mating connector 501. Use of the alignment capacities offered by the standard pyramidal connector allows for alignment of the hip joint and/or thigh segment in the frontal plane. Such frontal alignment can be performed both to accommodate misalignment of the mating connector 501 mounted on the socket lateral wall 200a', or the socket wall alignment itself, as well as to perform dynamic alignment of the thigh segment during swing or stance phase of the gait cycle. In swing phase, the pyramidal connector 500 can be used in order to correct medial-lateral tilt and ensure that the prosthetic lower-limb remains in the sagittal plane for most of the swing phase hip flexion motion. In stance phase, the pyramidal connector can be used in order to correct for frontal plane weight line position and alignment such that the user does not get pushed medially or fall laterally. Other embodiments include other types of connectors that provide suitable support and motion capabilities.

Similarly, the pyramidal connector 500 illustrated in FIG. 5 can allow for coronal plane alignment of the hip prosthesis such that the device does not show significant internal-external rotation, which could in turn result in lower-limb swing phase motion outside of the sagittal plane. Again, use of a pyramidal connector at the hip prosthesis proximal interface can also reduce requirements for achieving perfect alignment of the connector mounted on the lateral socket wall, or the socket lateral wall itself, with the sagittal plane.

Of note, use of a standard pyramidal connector and/or another type of connector at the proximal interface of the hip prosthesis does not limit embodiments to connectors allowing only for alignment in the medial-lateral and internal-external rotation directions. Offset connectors can be used to correct for the prosthetic hip joint's center of rotation position. Connectors allowing rotational positioning can be used in order to adjust the sagittal plane neutral hip position such that the resulting weight line enables the user to stand securely and comfortably. Furthermore, height shims can be used with the various connectors and/or adapters mentioned above in order to achieve proper positioning of the weight line in the frontal plane.

Figure 6:
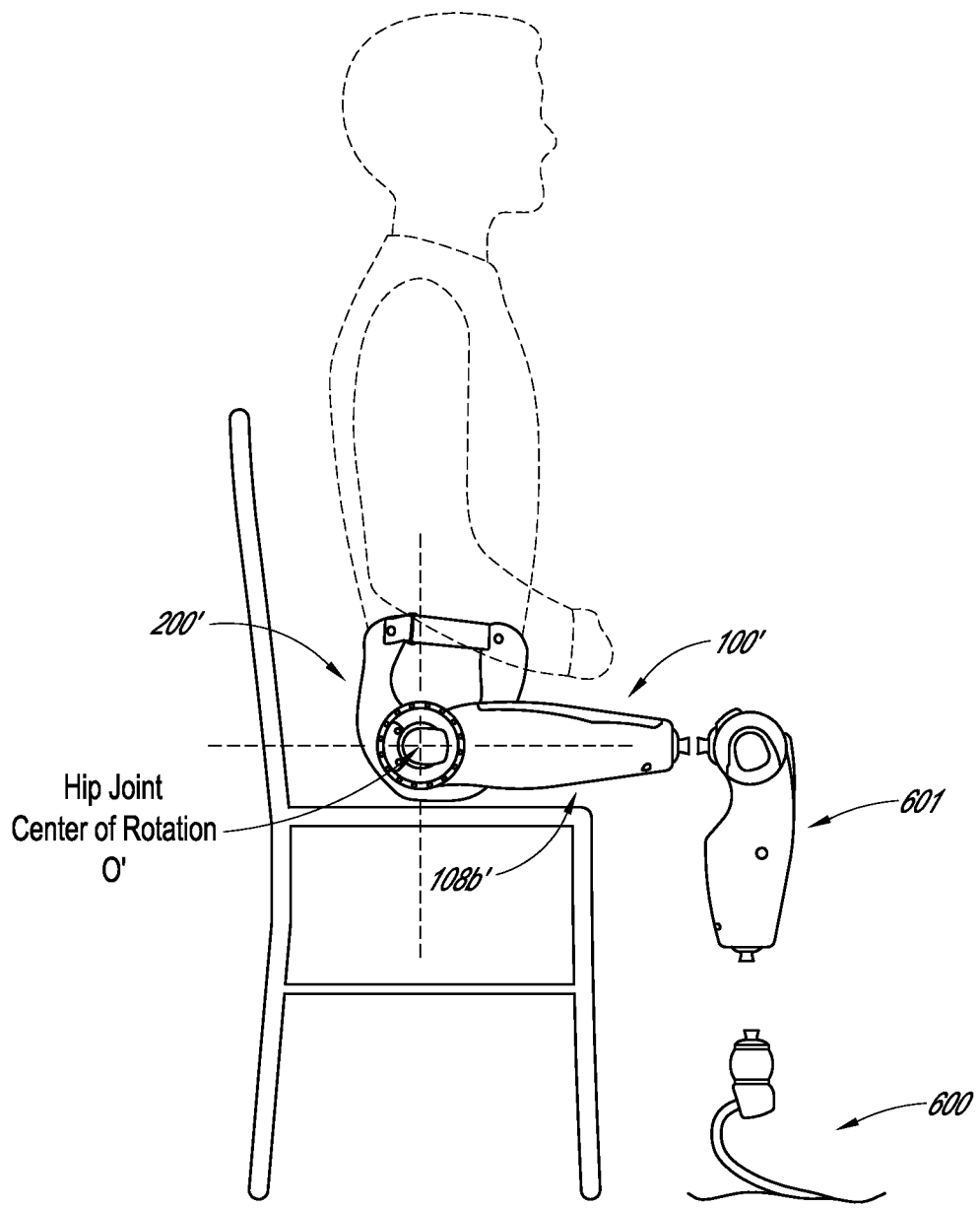
FIG. 6 is a schematic side view representation of a prosthetic hip joint embodiment when used by a user seated on a chair.

FIG. 6 illustrates the general configuration of the powered prosthetic hip joint embodiments 100' of FIG. 4a and FIG. 5 when connected to a typical powered knee prosthesis 601 and a typical energy returning foot 600. FIG. 6 illustrates a configuration while the user is seated on a chair. In several embodiments, the powered prosthetic hip 100' is coupled to the knee prosthesis 601, which is coupled to the foot 600.

As briefly introduced above, the connection of the hip prosthesis to the lateral wall of the socket 200' can allow for rotation of the thigh segment 108b' around the hip joint axis O' such that all components of the device clear the socket sitting area, while still allowing for providing support to the user while completing the sitting-down task and providing assistance when the user is completing the standing-up task. Some of the benefits of this embodiment arise from the user's capacity to achieve sit transfers in a non-pathological manner, as well as the user's ability to sit in a normal fashion without being constrained or burdened by the prosthetic device.

Figure 7:
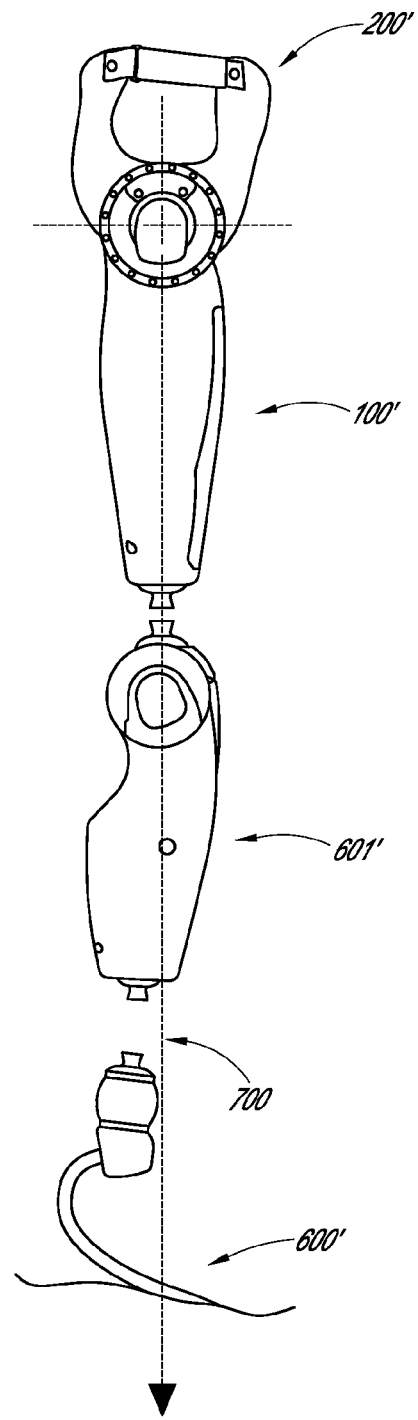
FIG. 7 is a schematic side view of a prosthetic hip joint embodiment when used by a user in a standing position.

FIG. 7 illustrates the general configuration of the powered prosthetic hip joint embodiments 100' of FIG. 4a and FIG. 5 when connected to a typical powered knee prosthesis 601' and a typical energy returning foot 600'. FIG. 7 illustrates a typical configuration, use, and/or alignment while the user is standing. The capacity of the hip joint to perform stance control allows positioning the weight line 700 in an anatomical fashion where the prosthetic knee is maintained slightly flexed to increase user postural stability and comfort. In a similar manner, the powered hip joint neutral position, while operating the device in standing mode, can be modified in order to provide a slight flexion, to provide a slight extension, and/or to remain fully neutral (as illustrated) in order to accommodate the socket design, the user mobility level, the postural balance, and/or the other components used in the lower-limb assembly (e.g., a prosthetic knee and foot). Hence, use of a slightly extended hip neutral position in standing can help maintain the knee in full or hyper extension, which is sometimes required for mechanical and passive knee prostheses. On the other hand, use of a powered hip prosthesis with a knee allowing for proper support and stance control while operated in standing mode can allow for alignment of the hip joint neutral position to be slightly flexed, such that the user can reduce energy expenditure and adopt a more comfortable position in the socket.

Figure 8:
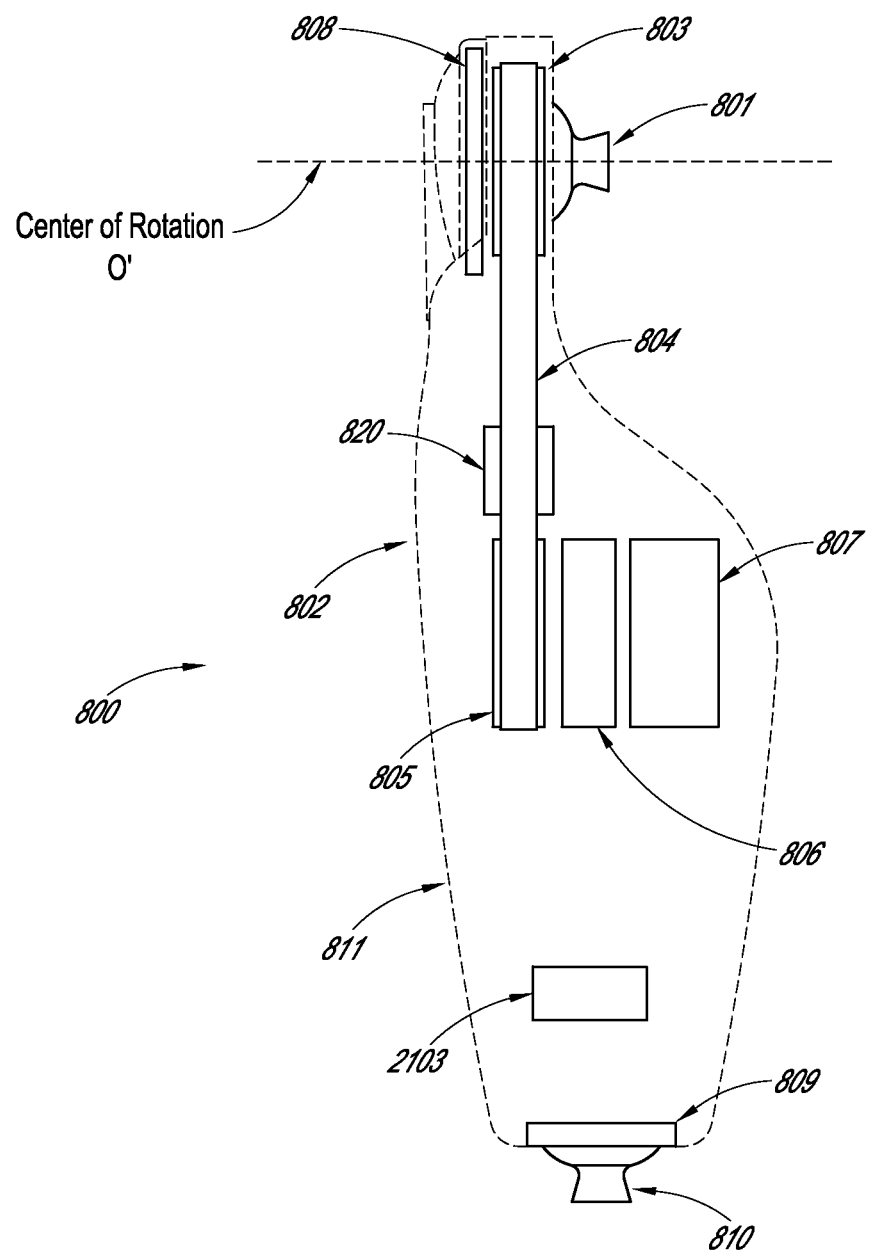
FIG. 8 is a schematic front view of a prosthetic hip joint embodiment illustrating a motor offset from the hip joint axis, according to one embodiment.

FIG. 8 provides a schematic representation of a hip joint with a powered actuator. In order to achieve powered motion of the lower-limb assembly with respect to the user socket, this embodiment illustrates a deported motor and transmission configuration. (A deported motor is a motor that is located remotely, such as offset, from the rotational axis of the joint that the motor powers. In some embodiments, deported motors are located distally from the hip's anatomical center of rotation.) This configuration allows for minimizing the device build height laterally to the socket lateral wall (i.e., the width of the hips when viewed in the frontal plane).

Minimizing build height can be important to prevent difficulties associated with the use of normal clothes. For example, a prosthetic device with a large build height could result in a hip width that does not enable the user to fit in typical clothing (e.g., pants) and could result in a non-anatomical and/or unnatural body profile when viewed in the frontal plane. Thus, many embodiments include features that avoid affecting and/or minimize the overall prosthetic width at the proximal connector area.

A powered prosthetic thigh 800 can include a proximal connector 801 based on a standard prosthetic pyramidal connector, which can be fixed, coupled, and/or rotationally coupled with the mating part located on the socket lateral wall through the use of four set-screws (not shown). As mentioned above, the use of the set-screws can allow for alignment of the device with respect to the socket. Similarly, a standard prosthetic pyramidal distal connector 810 can be fixed on the distal end of the elongated body 802 to allow connecting with other prosthetic components, such as knee joints, adapters, and/or pylons. Several embodiments use different types of connectors on the distal end of the elongated body 802.

Figure 9:
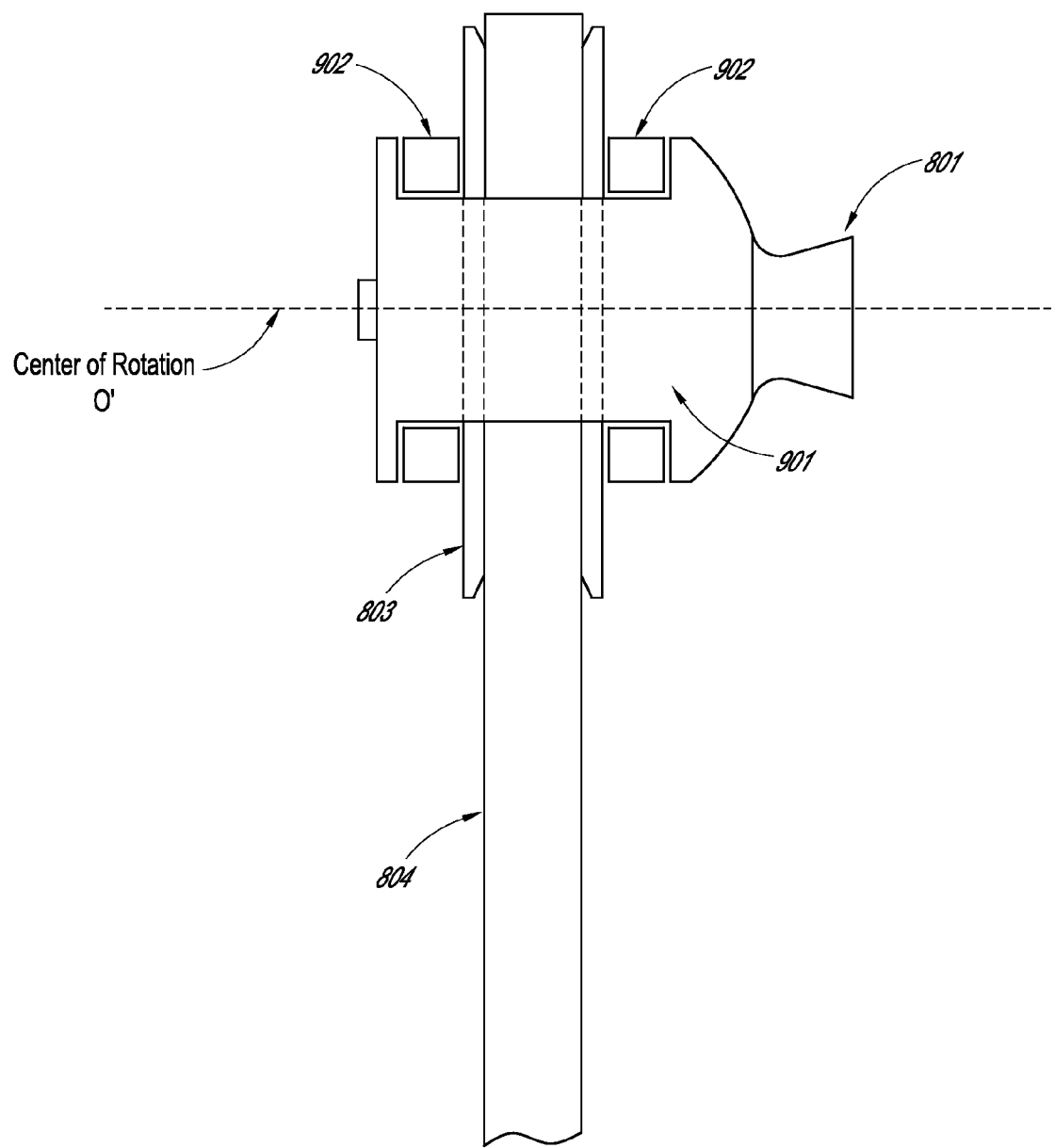
FIG. 9 is a detailed view of a proximal connector assembly embodiment that includes a power transmission system that can be used with the remotely located motor of FIG. 8, according to one embodiment.

Referring now to FIGS. 8 and 9, the proximal connector 801 can be fixed on a shaft 901 (see FIG. 9), which is allowed to rotate with respect to the elongated body 802 through the use of bearing(s) 902. Of note, the bearing configuration allowing relative rotation of the proximal connector 801 with respect to the elongated body 802 is not limited to the use of a pair of bearings spaced apart. A single bearing configuration can also be used through the use of components that are designed for supporting moment loads, such as Cross-Roller Rings (made by THK Co. Ltd.) or another similar product.

In the illustrated embodiment, a pulley or sprocket 803 is fixed to the proximal connector shaft 901. A belt, timing belt, or chain 804 operatively connects the proximal pulley or sprocket 803 to the distal pulley or sprocket 805. In one embodiment, the chain can be a metal roller chain.

Other power transmission systems, such as gears or planetary gears, are herein considered and will not be exhaustively listed. Furthermore, it is to be noted that the proximal 803 and distal 805 pulleys or sprockets can be of different dimensions such that a motion amplification or reduction is achieved directly in the power transmission chain. Similarly, the proximal 803 and distal 805 pulleys or sprockets can be of non-constant radius (i.e., cam-shaped), such that non-linear power transmission can be achieved based on the actual rotational position of the proximal connector 801 with respect to the elongated body 802.

The distal pulley or sprocket 805 can be functionally connected to a transmission unit 806, which in turn is functionally connected to an electrical motor 807. In other non-illustrated embodiments, the distal pulley or sprocket 805 is connected to the electrical motor 807 assuming that the combination of the specified properties of the power transmission system and electrical motor allow the system to fulfill the motion and power requirements at the proximal connector 801 level. Basic functional requirements for a powered prosthetic hip joint, such as motion and power performance requirements, can be taken directly from the data measured on normal individuals and/or reported in the literature. For example, see the basic data summarized in FIG. 20.

In some embodiments, functional connection of the transmission unit 806 and the electrical motor 807 to the elongated body 802 is achieved in a rigid manner, which does not allow any relative motion (or at least does not allow substantial relative motion) of the transmission unit 806 and the electrical motor 807 with the elongated body 802. In several non-illustrated embodiments, it is possible to use an alternative approach where flexible or semi-flexible connection of the transmission unit 806 and/or electrical motor 807 with respect to the elongated body 802 allows for measurement of the net torque applied by or to the electrical motor 807. Furthermore, flexible or semi-flexible connection of the transmission unit 806 and/or electrical motor 807 also allows enabling compliance of the powered prosthetic thigh 800 and/or the elongated body 802 with respect to the user socket. Such compliance allows for shock absorption and dynamic reconfiguration of the alignment between the hip prosthetic and the user socket without requiring the control system to directly intervene or move the system reference position. For example, the compliance can be particularly helpful during walking and/or standing to allow for shock absorption and dynamic reconfiguration.

In several embodiments, a further benefit of the use of a flexible or semi-flexible transmission unit 806 and/or electrical motor 807 casing is that it enables direct measurement of the net torque present at the powered prosthetic thigh 800 and socket interface, as introduced above. Use of a compliant element, such as a spring or a resilient material like a rubber bumper, of known stiffness coupled with a position sensor (e.g., optical encoder, magnetic encoder, potentiometer, resolver, etc.) enables determining the torque. Other embodiments, such as load cells or strain gauges, can be used for torque measurement in this actuator configuration. Several embodiments use a spring loaded tensioner 820 that interacts with the belt, timing belt, and/or chain 804. Measuring the deflection of the spring loaded tensioner 820 enables the controller to quantify, determine, sense, and/or detect a torque, such as the torque applied on the pulleys or sprockets 805', 803' and/or the torque at the proximal connector 801. A spring loaded tensioner 820 can also provide compliance in the system, such as between the proximal connector 801 and the mechanism, such as the electrical motor 807, that supplies the torque.

A hollow thigh structure 811 can be desirable to achieve a compact hip prosthetic device that has an anatomical form and a volume consistent with a normal human thigh. The hollow thigh structure 811 can be made in such a way as to hold all or a substantial portion of all electronic components required of the prosthetic hip device. Example electrical components include components to power the electrical motor 807 and interface the various embedded sensor modules, such as the hip joint sensor module 808 and/or the distal connector sensor module 809. Example electronic components can also include the processing platform, which allows the system to implement the memory, and processor devices to execute the software programs associated with controlling the powered hip prosthesis. The battery pack 300 can also be located, disposed, and/or placed in the thigh structure. The battery can be a removable battery pack 300, although some embodiments include a non-removable, rechargeable battery. A processor 2103 and all the other elements of the hardware system architecture embodiments described herein can also be disposed in the powered thigh prosthesis 800.

The hip joint sensor module 808 can be located directly on the hip joint axis (as illustrated) or on the motor 807 axis. Assuming that the power transmission mechanism used to connect the hip joint axis O' and the motor 807 axis is sufficiently rigid, no significant loss of information takes place by moving the hip sensor module 808 to the motor axis, while potential benefits arise from a device packaging standpoint. Some embodiments place the hip sensor module 808 in other locations. For example, some embodiments of hip sensor modules measure the movement of the belt, timing belt, or chain 804.

The thigh structure can be made using various materials and manufacturing processes. In some embodiments, lightweight materials presenting good structural strength are beneficial as they can allow fulfilling the desired structural strength requirements without uselessly increasing the device weight. Some embodiments do not use lightweight materials presenting good structural strength. Normal grades of aluminum, as well as aircraft grade aluminum, aluminum-magnesium alloys, and titanium alloys can be used to build the required structural components. For highly stressed components, steel and/or stainless steel alloys are used in some embodiments, even if the resulting components' weight is higher. Polymeric materials, such as carbon fiber, carbon-fiber reinforced plastics, glass fiber, and/or plastics, are used in some embodiments when the structural and fatigue strength requirements can be easily met by these materials. Structural parts required to build the prosthetic hip can be made using well known industrial manufacturing process such as milling; turning; die-casting; plastic or metal injection in closed molds; lamination under positive pressure (i.e., greater than atmospheric pressure); and/or lamination under vacuum (i.e., less than atmospheric pressure).

Returning to the transmission unit 806, it is to be understood that multiple types of transmission mechanisms can be used in order to convert the motion and power provided by the electrical motor 807 to the power and motion levels that are required by the desired hip prosthetic application. Furthermore, it is to be considered that the final gear ratio between the electrical motor 807 and the proximal connector 801 can be achieved in a single stage or in multiple stages of linear or non-linear mechanisms, which can be rigid or compliant. In several embodiments, these configurations provide optimal function in an anatomically compliant volume and/or in a volume that is anatomically consistent with the volume of a natural body, such as a hip and thigh. Several embodiments include transmission technologies that fit in the allowable volume and enable a gear ratio that is proper, ideal, and/or preferred for the application. Some transmission embodiments use a harmonic drive or planetary gear to enable high-gear ratios and high torques while still meeting the substantial weight and volume constraints associated with lower-limb prostheses.

Regarding the electrical motor 807, it is to be understood that various electrical motor technologies that meet prosthetic hip functional requirements can be used with the many embodiments described herein. As described above, electrical motors that provide a compact design and appropriate power density, energy density, torque, and/or velocity levels can be used with the prosthetic hip described herein. Examples of such motor technologies include brushless DC motors, DC stepper motors, ultrasonic motors, and DC brushed motors. Motors based on such technologies can be constructed in several ways in order to accommodate prosthetic hip design requirements as well as specific performance requirements. Hence, assemblies comprising a moving rotor located inside of a fixed stator part can be used, as well as outer rotor assemblies or moving stator assemblies.

Figure 20:
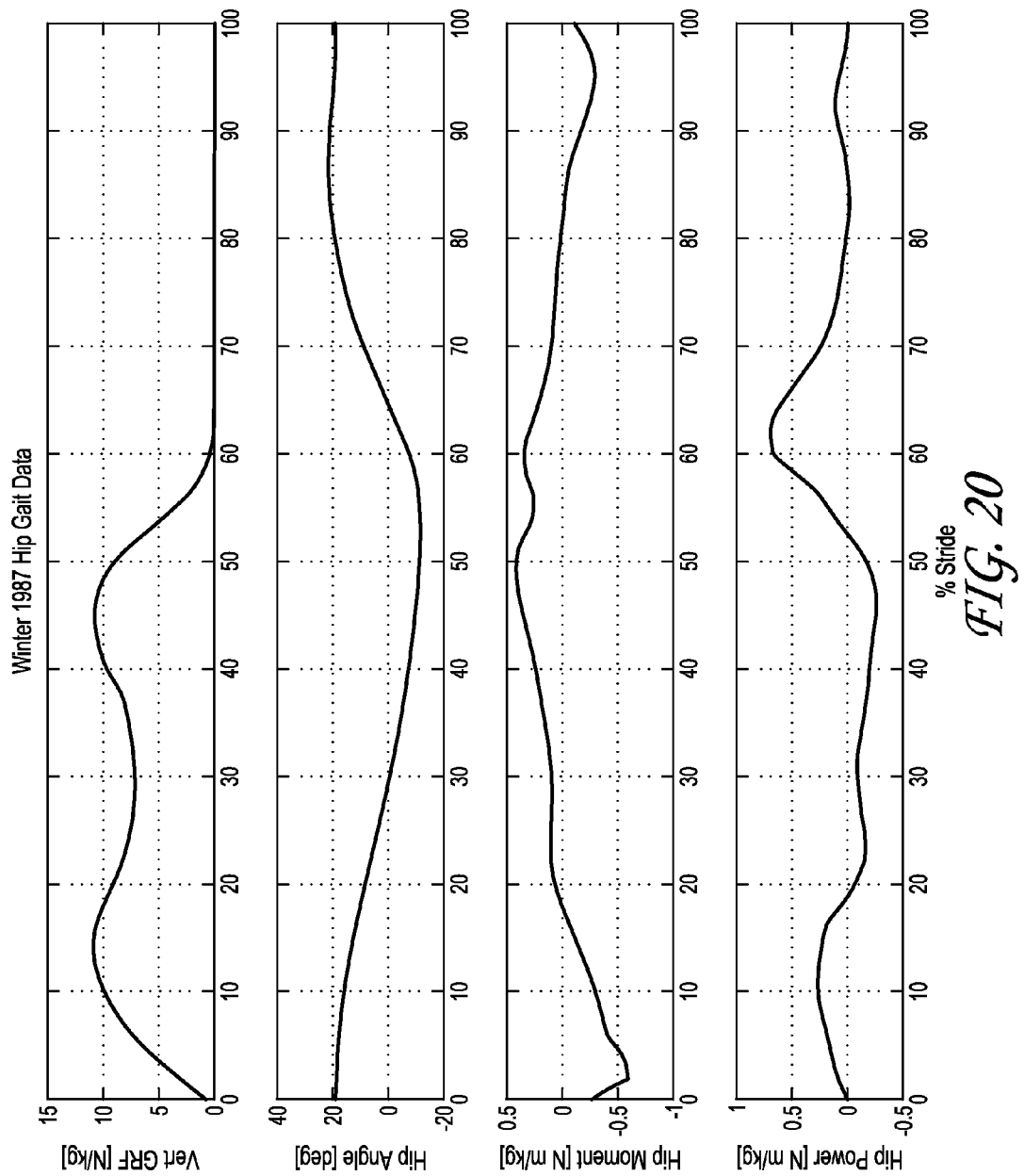
FIG. 20 illustrates hip level gait data, according to one embodiment.

Regarding the basic functional examples expressed by FIG. 20, it is to be understood that several strategies can be adopted in defining the specific functional requirements of prosthetic hip devices. More specifically, the definition of the prosthetic interface torque and motion requirements is often directly related to each device's intended use and the specific actuator embodiment. From the data presented in FIG. 20, it can be observed that the power and motion requirements often vary greatly between swing and stance phase of level walking gait. Hence, the creation of a device only intended to replace lost stance function often leads to a fairly different definition of functional and actuator requirements than if the device is also intended to replace swing phase functional dynamics.

Some embodiments include a device with an objective of restoring lost hip joint functions in stance and swing phases. Many of these embodiments are able to sustain the motion, torque, and power levels defined in FIG. 20. Several alternative embodiments include a device that generates motion, torque, and power during swing phase but does not actively provide moving power during stance phase. Such an alternative embodiment would allow the use of a hybrid actuator, where stance phase power dissipation could be performed by an auxiliary breaking unit coupled to the power-generation unit used to power swing flexion.

Figure 10:
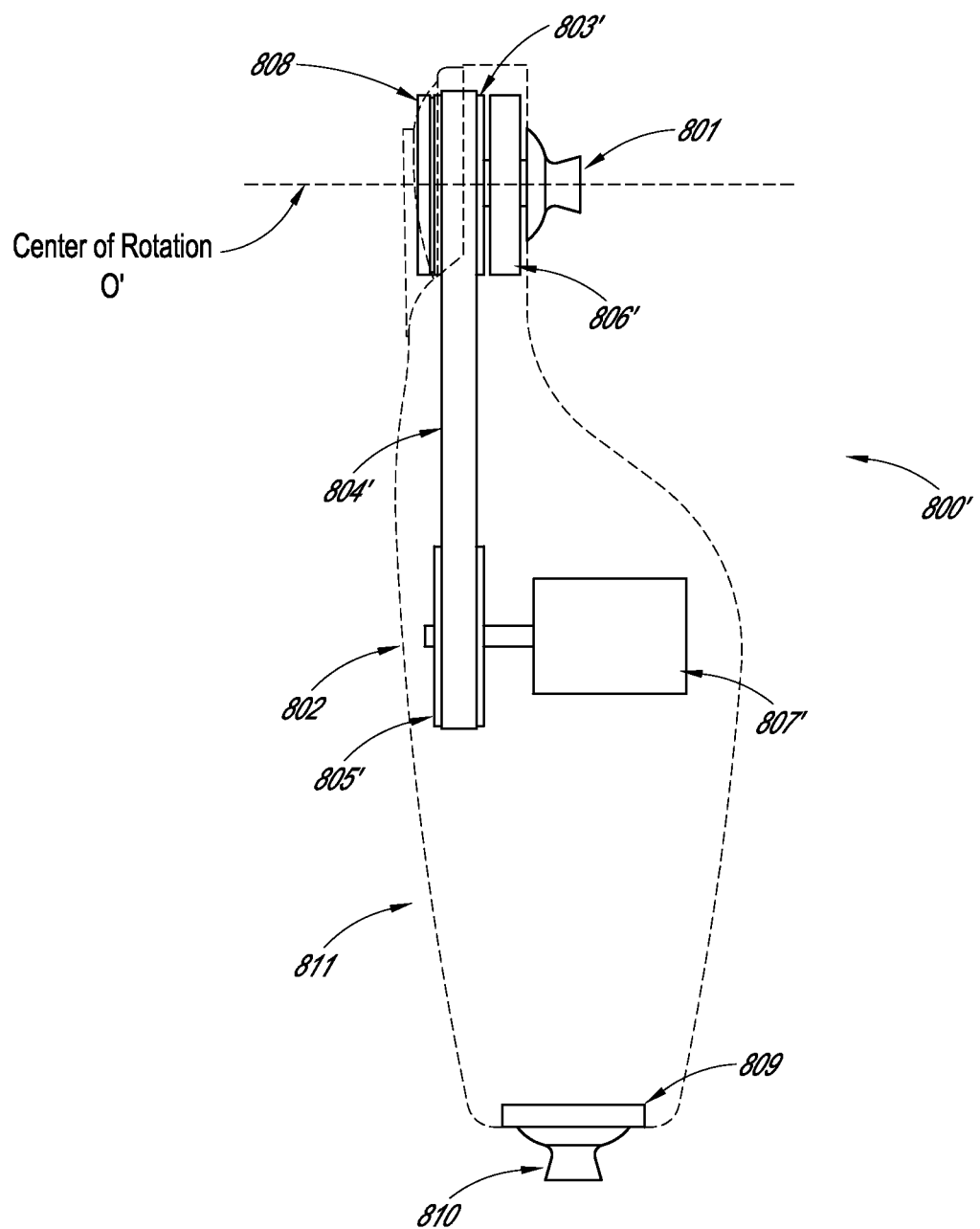
FIG. 10 is a schematic front view of the prosthetic hip joint embodiment of FIG. 5 illustrating an actuator with remotely located elements, according to one embodiment.

FIG. 10 presents another embodiment of a powered thigh prosthesis 800'. This embodiment differs from several previously introduced embodiments by the fact that the electrical motor 807' is deported or located remotely from the hip joint axis, while the transmission unit 806' is mounted co-linearly and coaxially with the hip joint axis. Such a configuration often enables the benefit of having the pulleys or sprockets 805', 803' and the belt or chain 804' carry a lower load since they are located on the low-torque/high-speed side of the transmission unit 806'. Depending on the specific functional requirements desired and the components' sizes, several embodiments with this configuration have a more compact assembly than the assembly illustrated in FIG. 8. Furthermore, operation of the belt, timing belt, or chain 804' under the low-torque/high-speed conditions may also result in increased functional life of the components and a more rigid overall actuator construction in several embodiments.

Figure 11:
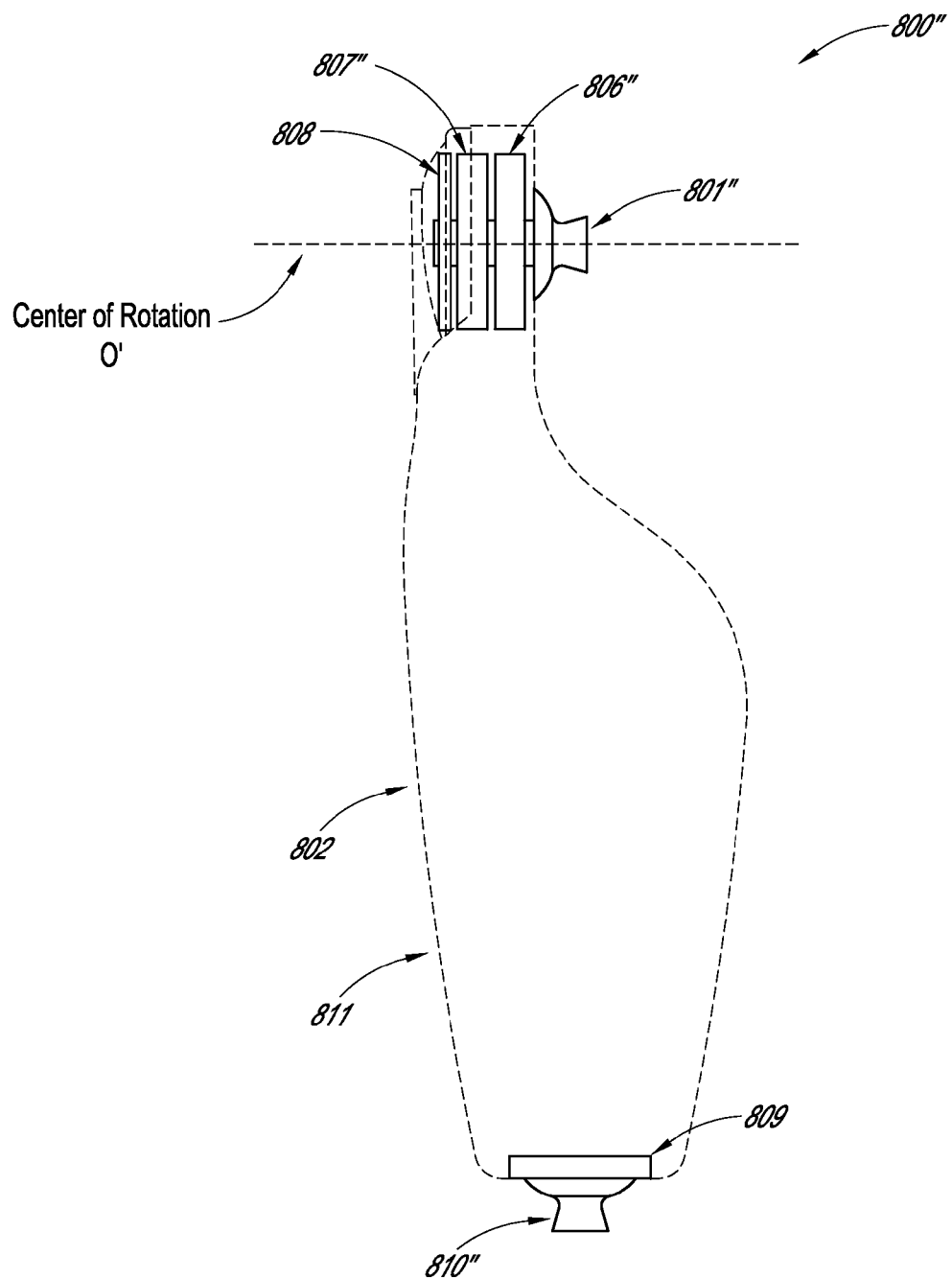
FIG. 11 is a schematic front view illustrating an actuator embodiment mounted on a hip joint axis.

FIG. 11 presents another embodiment of a powered prosthetic thigh 800'' This embodiment illustrates collinear and coaxial mounting of an electrical motor 807'', a transmission unit 806'', and a proximal connector 801'' with the joint axis of rotation O'. Several embodiments use coaxial mounting of an electrical motor, a transmission unit, and/or a proximal connector.

This construction can result in a compact device, where it is possible to minimize the overall built height and optimize the distance between the proximal connector 801'' and the distal connector 810'', which can lead to reduced socket loading through direct weight and inertial effects. While collinear mounting embodiments sometimes result in a slightly wider construction at the proximal connector level, this embodiment is particularly well suited for the combination of a large diameter electrical motor with a smaller diameter transmission unit, where the transmission unit can be partly or fully integrated into the rotor of the electrical motor. Use of a larger diameter electrical motor is easier to blend in the hip-level anatomical features, where it is easier to blend in a large diameter cylindrical volume with low height mounted laterally to the socket, than it is to blend in a small diameter cylindrical volume and high height mounted in the same fashion.

Figure 12:
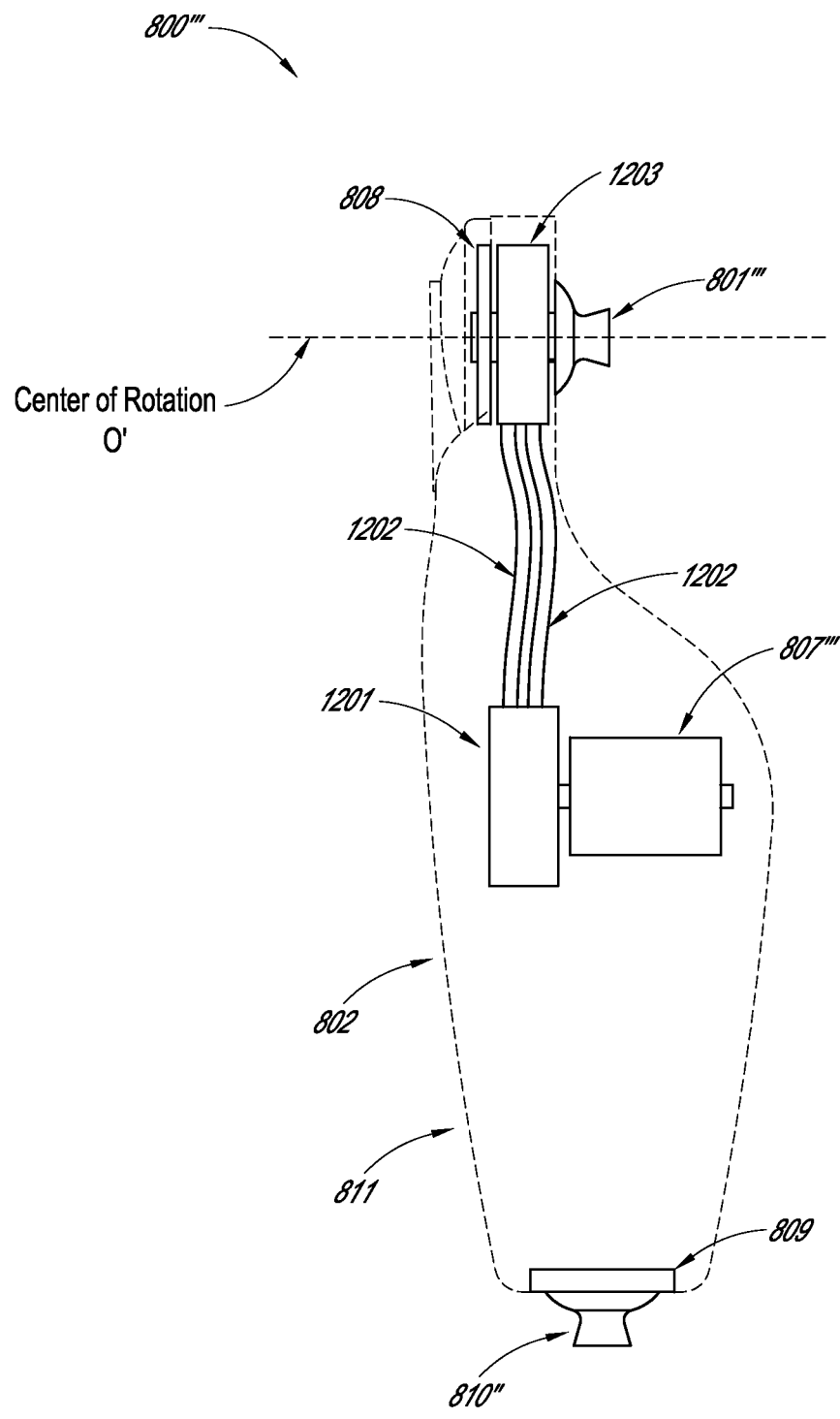
FIG. 12 is a schematic front view of a prosthetic hip joint embodiment with a hydraulic pump embodiment.

FIG. 12 illustrates another embodiment of a powered prosthetic thigh 800''' wherein an electrical motor 807''' is mounted distally from the hip joint rotation axis O' and proximal connector 801''' This embodiment further illustrates use of a hydraulic power transmission system instead of the systems previously illustrated. More specifically, the electrical motor 807''' is operatively coupled to a hydraulic pump 1201, which in turn is connected via hydraulic hoses and connectors 1202 to a hydraulic motor or hydraulic actuator 1203, which is operatively coupled to the proximal connector 801'''. Based on the exact configuration of the electrical motor 807''' and the hydraulic pump 1201 combination, hydraulic valves and accumulators (not shown) can also be used in order to properly direct the hydraulic fluid flow and pressure. Other embodiments of the electrical motor 807''' and hydraulic pump 1201 allow use of a reversible pump, which in turn allows the hydraulic motor 1203 to move in both directions without requiring one or more valves.

Different types of hydraulic motors and hydraulic actuators can be used in the embodiment illustrated in FIG. 12. While conventional hydraulic motors can be used to move the proximal connector 801''' in both directions and under specific torque profiles, it is also possible to use a dedicated hydraulic actuator, which could provide less-than-one-turn range of motion, but could also allow implementing motion stops as part of the actuator itself.

Figure 13:
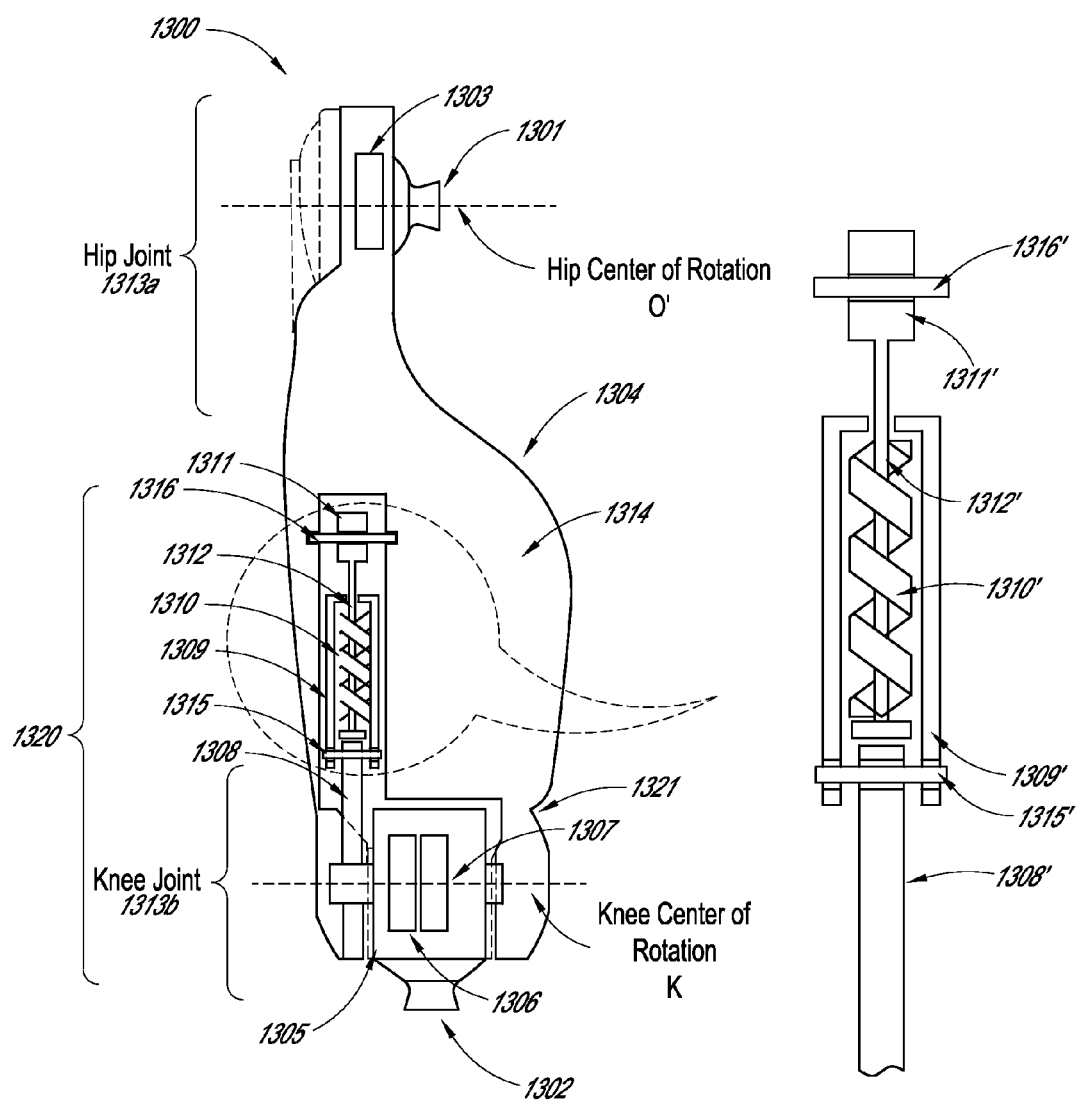
FIG. 13 is a schematic front view of a dual-joint prosthetic thigh embodiment with a hip actuator, a knee actuator, and a compliant link, according to one embodiment.

FIG. 13 illustrates a powered prosthetic thigh embodiment with dual joints. The powered prosthetic thigh 1300 includes a hip joint 1313a and a knee joint 1313b. One objective of this prosthetic device is to replace lost functionality associated with the hip and knee joints for amputees having undergone a hip-disarticulation or a hemi-pelvectomy amputation. While various previous embodiments have relied on the use of independent devices to restore the functions lost at each joint, the present embodiment uses a single device to restore the complete thigh segment functions. One benefit of this embodiment is allowing synchronized operation of the two joints, as well as allowing dynamic power generation management, which are both features consistent with normal human gait. Of note, several other embodiments, such as the embodiment illustrated in FIG. 6, can also allow synchronized operation of multiple joints (including the ankle joint in some embodiments) by enabling the various joints to communicate with each other and/or with a central control system. Further disclosure on synchronization of joints, or communication between joints, among other things, can be found in U.S. Patent Application Publication No. 2006/0184280 and U.S. Patent Application Publication No. 2006/0184252, the entirety of both of which are incorporated herein by reference and should be considered a part of this specification.

The powered prosthetic thigh 1300 of FIG. 13 includes a proximal connector 1301 enabling the connection of the powered prosthetic thigh 1300 to a user socket (not shown). A distal connector 1302 enables further connection of the powered prosthetic thigh 1300 to a shank segment pylon and/or a prosthetic ankle/foot device (not shown). Of note, the use of any type of prosthetic ankle/foot product is allowed by the powered prosthetic thigh 1300. Nevertheless, various benefits arise from the use of a lightweight solution as the hip-disarticulated or hemi-pelvectomy sockets are known for presenting very limited suspension capacity. Use of a heavy prosthetic limb generally leads to issues with socket pistoning and achieving proper foot clearance in swing phase.

A hip joint actuator 1303, such as any of the hip actuators described herein, is functionally connected to the proximal connector 1301 to allow hip motion. Thigh segment structural components 1304 housing the hip actuator 1303, supporting electronics, and a battery are further operatively connected to a knee joint actuator 1305. The powered prosthetic thigh 1300 also includes a hollow structure 1314, although many embodiments do not have a hollow structure.

As introduced above for single joint hip prosthetic device embodiments, any type of knee joint can be used in the dual joint thigh prosthesis of FIG. 13. However, significant benefits arise in several embodiments from the use of a knee joint relying on a fully controllable actuator instead of passive linkages or mechanical break embodiments. Furthermore, to fully benefit from the device's capacity to synchronize the operation of the hip and knee joints during operation in normal gait, several embodiments use a controllable powered actuator, a dynamically configurable damper, and/or a dynamically configurable breaking system.

FIG. 13 illustrates a powered prosthetic thigh 1300 embodiment where a powered knee actuator 1305 with a compliant transmission 1320 is coupled to a distal portion 1321 of the powered prosthetic thigh 1300. FIG. 13 includes an enlarged view of several components. A distal connector 1302 is rigidly connected to the knee joint actuator output port. The knee joint actuator 1305 itself can include an electrical motor 1307 coupled to a harmonic drive transmission 1306, both of which are mounted in a fashion that ensure their co-linearity with the knee anatomical sagittal plane rotational axis K. The harmonic drive 1306 output is further connected to an output lever 1308, 1308', which is pivotably connected to a spring housing 1309, 1309', using a pin 1315, 1315', which constrains one end of the spring stack 1310, 1310'. The other end of the spring stack 1310, 1310' is constrained by the stress tubes 1312, 1312', which are in turn operatively coupled to the frame connecting pivot 1311, 1311' using a pin 1316, 1316'. In such a configuration, the frame connecting pivot 1311, 1311' allows the assembly including the stress tube 1312, 1312' and the spring housing 1309, 1309' to rotate relative to the thigh structural components 1304 when sagittal plane loading is applied between the thigh structural components 1304 and the distal connector 1302.

Thus, in the illustrated embodiment, the compliant transmission 1320 couples the distal connector 1302 and the distal portion 1321 of the powered prosthetic thigh 1300. The compliant transmission 1320 is configured such that relative rotation between the distal connector 1302 and the distal portion 1321 stores or releases mechanical energy.

Relative motion of the knee actuator output lever 1308, 1308' with respect to the thigh structural components 1304 causes the spring housing 1309, 1309' to rotate, which creates an increase in the distance between the output lever connecting point and the frame connecting pivot 1311, 1311'. The system compensates for the increased distance via the compression of the spring stack 1310, 1310' and a translational relative motion between the spring housing 1309, 1309', and the stress tube 1312, 1312'

The presence of the spring stack 1310, 1310' in the knee joint assembly can generate observable compliance between the distal portion 1321 and the distal connector 1302. This compliance can provide multiple benefits in the operation of a powered knee joint prosthetic, including a capacity to store and release mechanical energy during knee stance flexion-extension cycles in early stance phase of walking gait, a capacity to provide a direct measure of net torque across the joint, a capacity to absorb shocks, and, finally a capacity to generate a passive knee compliance which increases user comfort.

For optimal performance of the knee behavior according to several embodiments, it can be desirable to match the knee passive compliance with a compliance typically associated with the normal human knee during the initial flexion-extension of level walking gait. Some embodiments include targeting the high-side of the normal knee stiffness to increase the likelihood that a single spring stack design fits all user preferences, gait patterns, and body masses. Of note, the spring's apparent stiffness can be dynamically reduced using the electrical motor and the control system. However, it cannot be increased in some embodiments. Furthermore, several embodiments rely on non-linear compliance, which allows further replicating the normal knee joint behavior when subjected to walking cadence changes.

Figure 14:
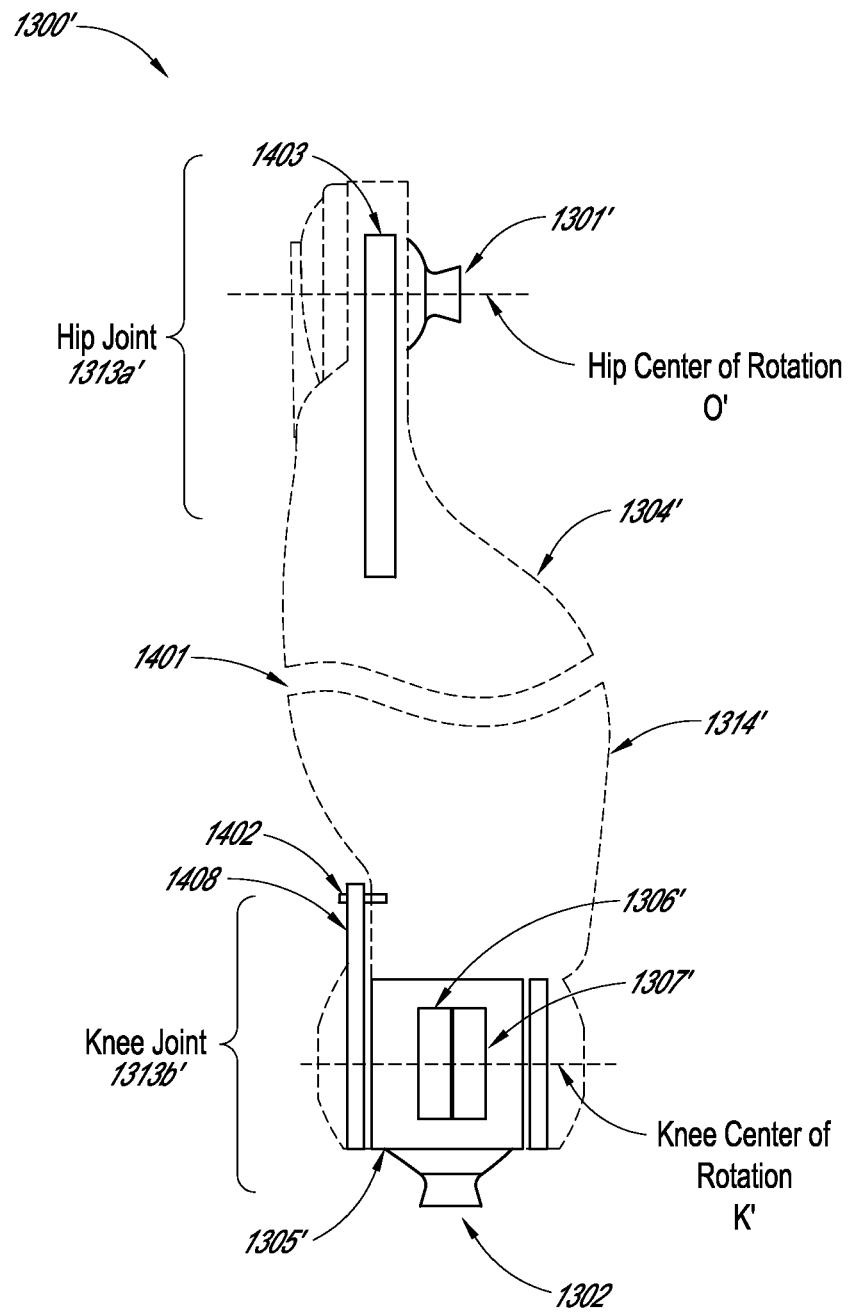
FIG. 14 is a schematic front view of a dual-joint prosthetic thigh embodiment with an adjustable thigh segment length embodiment.

FIG. 14 illustrates an embodiment of a powered prosthetic thigh 1300' with dual joints. This embodiment includes a hip joint 1313a' and a knee joint 1313b'. The embodiment in FIG. 14 uses a direct drive knee actuator 1305' instead of the compliant knee actuator 1305 previously described (shown in FIG. 13). The direct drive knee actuator 1305' can include an electrical motor 1307' coupled to a drive transmission 1306'. The powered prosthetic thigh 1300' can also include a hip joint actuator 1403. The embodiment illustrated in FIG. 14 can use any of the hip joint actuator embodiments described herein.

In the embodiment shown in FIG. 14, the knee actuator output lever 1408 can be directly connected to the thigh segment structural components 1304' through a pivot type connector and/or a pin 1402. Removal of the compliant stage of the power transmission system can reduce the features provided by the device, but also can result in the benefit of significantly shortening the device length used to connect the knee joint actuator 1305' to the thigh segment structural components 1304' and/or to the hip joint 1313a'. In turn, reduction of the constraint related to the knee joint connection can free up room to allow for a variable length thigh segment 1401 and provide additional space in the hollow structure 1314' for housing electrical components and a battery pack.

Due to the highly variable segment length combinations, amputation scenarios, and socket designs, being able to customize and/or finely adjust the distance between the hip joint center of rotation O' and the knee joint center of rotation K' can be helpful. Furthermore, being able to match the sound limb segment lengths on the prosthetic side enables fine tuning the system to increase gait symmetry and promotes uniform lower-limb loading during device use. Having similar segment lengths on both the sound side and the prosthetic side allows for uniform motion and weight distribution. Thus, significant improvements in device conviviality and performance arise when executing activities, such as sitting-down or standing-up from a seated position.

Figure 15:
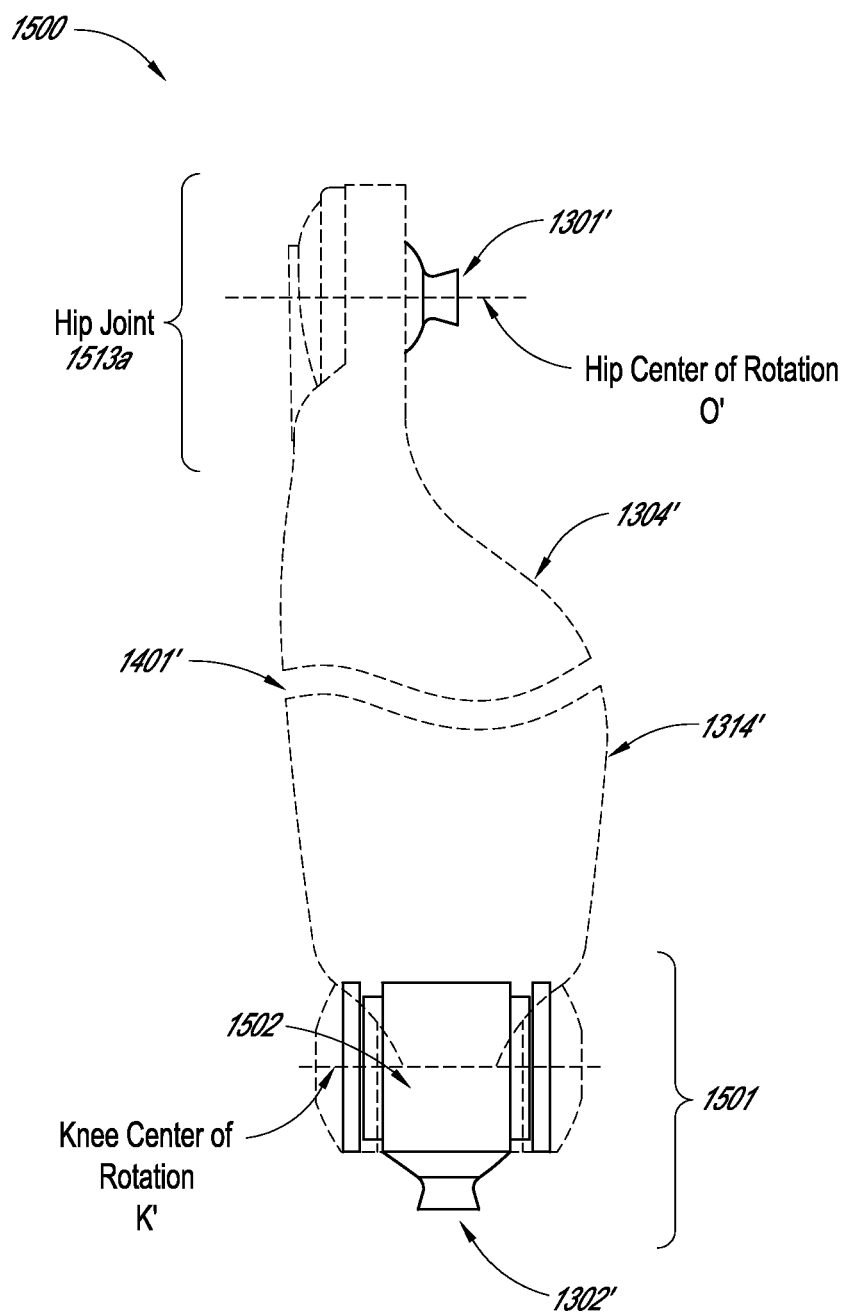
FIG. 15 is a schematic front view of a dual-joint prosthetic thigh embodiment with a magneto-rheological knee actuator embodiment.

FIG. 15 presents another embodiment of a powered prosthetic thigh 1500 with dual-joints (including a hip joint 1513a). A hip joint actuator (not shown), such as one of the many actuator embodiments described herein, is operatively coupled to the proximal connector 1301' and functionally connects to the thigh segment structural components 1304', which can be of variable length. A magneto-rheological (MR) knee joint actuator 1501 is fixed on the distal end of the thigh segment structural components 1304'. The MR actuator 1501 can include two sets of interlaced blades, one set being functionally connected to the thigh segment structural component 1304' (i.e., the stator), while the second set is functionally coupled to the knee housing 1502 (i.e., the rotor), which in turn is operatively coupled to the distal connector 1302'. The interstices between the rotor blades and the stator blades are filled with an MR compound composed of synthetic oil doped with fine iron particles. An electro-magnet is located in the actuator core and can be controlled in such a way that a variable magnetic field can be generated. Varying the magnetic field directly affects the MR compound's rheological properties, which in turn increases or decreases the friction between the stator and the rotor blades.

While the MR actuator does not provide the power generation capacities of the powered knee actuator of FIGS. 13 and 14, the MR actuator 1501 provides a highly controllable breaking system with good power density. Furthermore, such an actuator can provide good back-drivability properties, which can allow the use of the knee joint as a single axis knee when battery power is depleted. The coupling of a dissipative system such as the MR actuator 1501 to a powered hip joint also allows mitigating drawbacks sometimes associated with the hip's nature. Knee joint power is sometimes required in level walking in order to power swing phase flexion-extension cycles such that good synchronism and/or coordination between both joints can be achieved, and such that the system can optimize ground clearance and reduce the risk of falling or tripping. In situations where it is possible to provide the proper power and dynamics in the lower-limb system through the use of the hip joint, use of a MR damper may not cause significant performance limitations for the targeted user population, while enabling greatly reduced device weight, as well as moving the system's center of mass closer to the socket. Moving the center of mass as proximally as possible to the socket greatly reduces the load on the socket and the residual limb. Further information on MR dampers, among other things, can be found in U.S. Pat. No. 6,764,520 and U.S. Patent Application Publication No. 2006/0136072, the entirety of both of which is incorporated by reference and should be considered a part of this specification.

Figure 16:
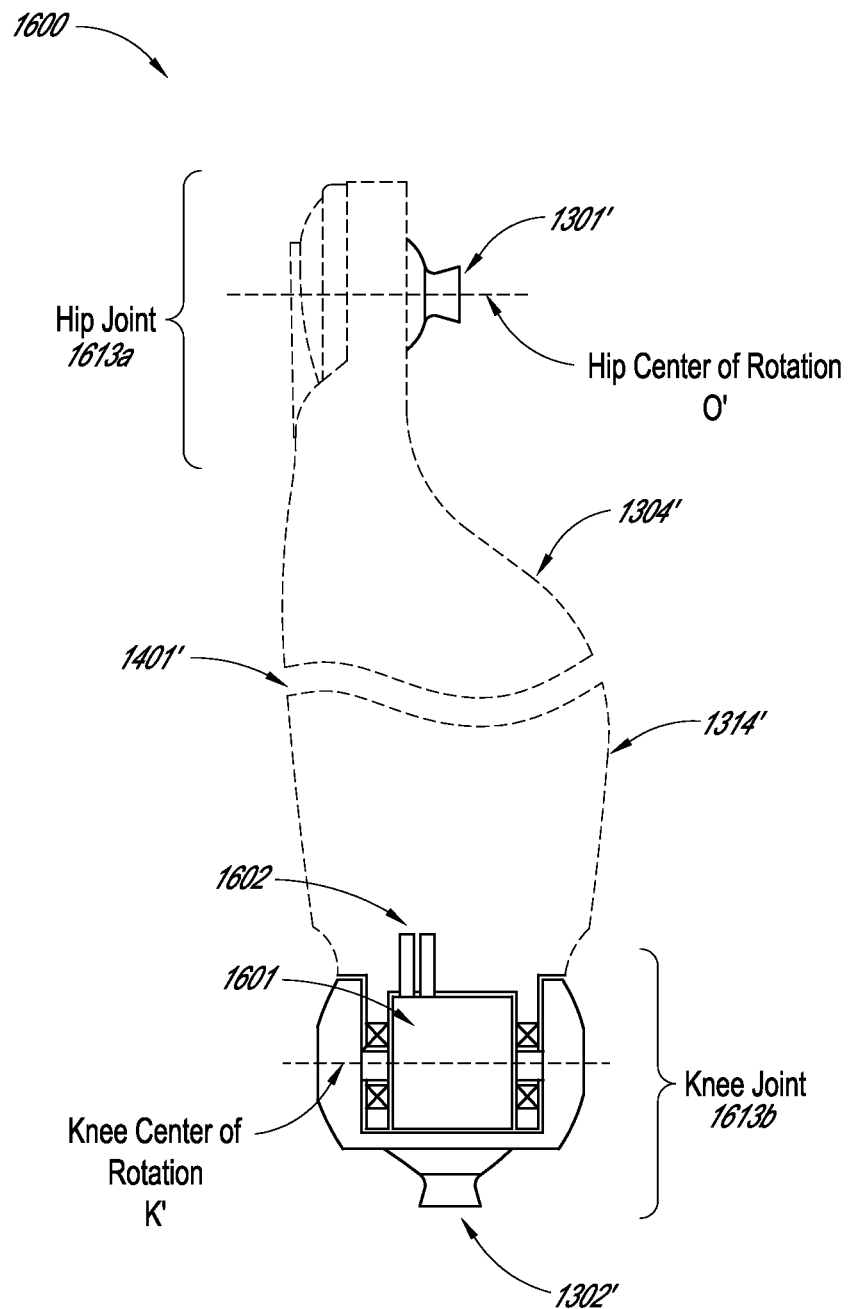
FIG. 16 is a schematic front view of a dual-joint prosthetic thigh embodiment with a hydraulic knee actuator embodiment.

FIG. 16 presents another embodiment of a powered prosthetic thigh 1600 with dual-joints (including a hip joint 1613a and a knee joint 1613b). This embodiment includes a proximal connector 1301' and a hip joint actuator (not shown) as described in other embodiments. The hip joint actuator is operatively coupled to the thigh segment structural components 1304', which can be of variable length. The length can be changed through adjustment of the variable length thigh segment 1401', which can include telescoping pylons. A distal part of the thigh segment structural components 1304' is fitted with a hydraulic knee joint actuator 1601. The moving portion of the hydraulic knee joint actuator 1601 is operatively coupled to a distal connector 1302'. The hydraulic knee joint actuator 1601 is placed in fluid communication with hydraulic power ports 1602, which in turn are connected to a power supply (such as the electrical motor 807''' and the hydraulic pump 1201 illustrated in FIG. 12) and/or to a closed circuit energy storing and dissipating unit composed of hydraulic pressure accumulators and controllable needle valves.

In several embodiments, the hydraulic knee actuator 1601 uses a hydraulic power unit to generate hip power as described herein. In such cases, further synergy between the hydraulic fluid flow and pressure generated through user motion during stance phases of walking can be used in order to prepare for the knee swing phase flexion-extension motion. Control strategy embodiments for dual-joint thigh segment prostheses with a hydraulic power supply can enable system efficiency optimization by recycling the dissipated power from one joint with the other joint, which can minimize the losses. In other words, power dissipated by one joint can be used by another joint.

Various embodiments that utilize a non-hydraulic hip actuator use a closed circuit energy storing and dissipating hydraulic unit instead of the power supply based unit. This approach allows minimizing the system complexity of managing two separate power sources. In some embodiments, this approach also avoids the increased weight and bulkiness associated with populating both systems in a single device.

Referring now to FIGS. 14-16, variable length thigh segments 1401, 1401' can be constructed in a number a ways. In some embodiments, care has to be directed to making sure the selected construction solution does not compromise the ability of the structural component to hold the device electronics, hold the battery pack, and/or limit the thigh's minimum length to a level that renders the thigh unpractical for use with a majority of the amputee population. Several embodiments include continuously selectable thigh lengths or discretely selectable thigh lengths. Some embodiments include 3 to 5 selectable thigh lengths, 3 to 10 selectable thigh lengths, and/or 2 to 20 selectable thigh lengths.

In some embodiments, a high number of configurations of the thigh segment prosthetic device may be desirable and/or advantageous. More specifically, several embodiments enable configuring not only the hip-knee length, but also enable configuring the relative orientation and position in all planes of the proximal and distal connectors such that inner or outer rotation and/or offsets in coronal or sagittal planes can be achieved directly in the thigh segment.

Figure 17:
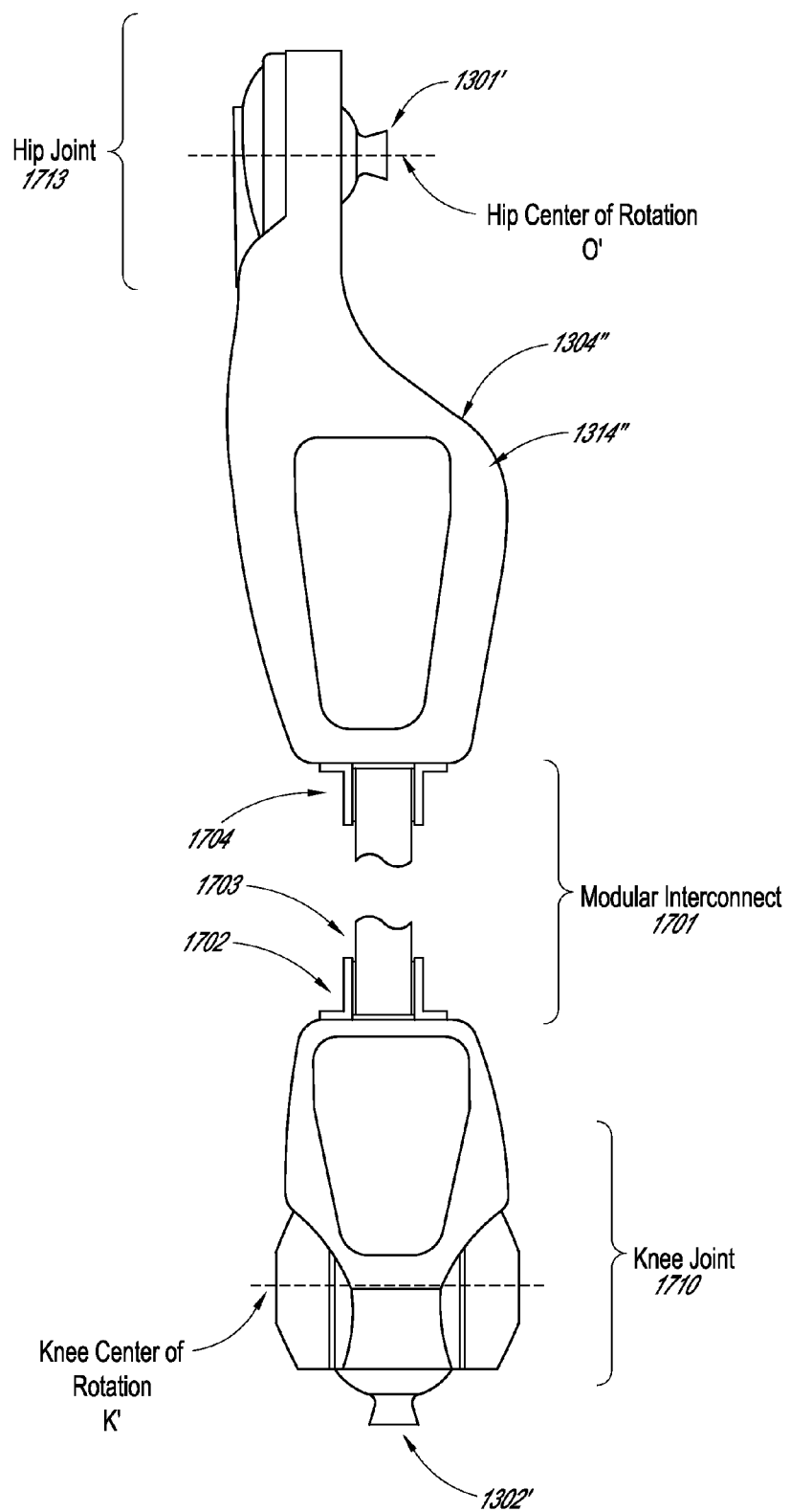
FIG. 17 is a schematic front view of a dual-joint prosthetic thigh embodiment with a thigh segment length that can be adjusted, according to one embodiment.

FIG. 17 illustrates an embodiment of a variable length thigh segment 1701 prosthetic system with dual joints (including a hip joint 1713). The embodiment includes a hip joint actuator (not shown) such as any of the hip joint actuators described herein. The hip joint actuator is operatively coupled to a proximal connector 1301' The hip joint actuator is further connected to the thigh segment structural components 1304" enabling the optional integration of all support electronics and battery power. For example, the support electronics and at least one battery can be placed in the hollow structure 1314".

The distal part of the thigh segment structural components 1304" is configured in such a way as to allow the integration of a prosthetic connector 1704. Any type of prosthetic connector that meets reasonable system requirements can be used. In several embodiments, the connector 1704 is a tube clamp. The tube clamp can be coupled to a pylon 1703, which can be cut to length by the prosthetist during the device fitting, wherein the device is configured based on the user's needs. This example interface combines both length adjustability and rotational adjustability in a single component selection. The pylon 1703 is further connected to a second prosthetic connector 1702. In the illustrated example, the second prosthetic connector 1702 is a tube clamp. Of note, the illustration of the tube clamps 1702, 1704 and the pylon 1703 should not be considered a limitation and is only provided as an example of a typical configuration. Other configurations using pyramidal connectors, offset connectors, and/or connectors allowing for rotation are also possible.

The second prosthetic connector 1702 is connected to the knee joint assembly 1710, which is illustrated here as a magneto-rheological knee joint. All knee joints described herein, including the knee joint illustrated in FIG. 13, can be used with the modular interconnection system for the thigh segment prosthetic system with dual joints.

FIG. 18a illustrates an embodiment of a prosthetic hip 1800 where a compliant member is integrated in the socket connector and/or integrated in the hip prosthetic device proximal connector. A powered prosthetic thigh 1804 provides a distal connector 1803 and a proximal connector 1805. Both connectors are represented by a pyramidal type connector, which is only one of many connector embodiments. Many embodiments use different types of connectors.

Proximal connector 1805 can be coupled with its counterpart 1806, which is typically mounted to the socket 1801, either directly, using screws or using a lamination adapter that is inserted between lamination layers of the socket itself during fabrication. The counterpart 1806 can be mounted to the lateral wall 1802 of the socket 1801. The illustrated embodiment uses an intermediate compliant component 1807 positioned between the socket lateral wall 1802 and the counterpart 1806 of the device proximal connector 1805. The position of the intermediate compliant component 1807 is not limited to be positioned between the socket lateral wall 1802 and the proximal connector 1805. The intermediate compliant component 1807 is positioned in other locations in other embodiments. In some embodiments, the intermediate compliant component 1807 is positioned and/or located between the device proximal connector 1805 and the rest of the powered prosthetic thigh 1804. In several embodiments, the intermediate compliant component 1807 is located between the powered prosthetic thigh 1804 and the proximal connector 1805. In some embodiments, the intermediate compliant component 1807 is approximately coaxial with the proximal connector 1805. In some embodiments, the intermediate compliant component 1807 is located between the proximal connector 1805 and its mating counterpart 1806. The intermediate compliant component 1807 in FIG. 18a can be made from a rubber material.

FIG. 18b illustrates another, more detailed, embodiment of an intermediate compliant component 1807'. In several embodiments, the intermediate compliant component 1807' allows for relative motion of small amplitude between a prosthetic connector 1806' and the socket lateral wall 1802' through the deformation of one or more compliant elements 1812', which are represented herein as a parallel arrangement of springs that are connected to the prosthetic connector 1806' on one side and to the socket lateral wall 1802' on the other side. Such an arrangement allows for rotation of the prosthetic connector 1806' with respect to the socket lateral wall 1802' when submitted to a frontal plane moment. Frontal plane moments are observed to occur when the user is operating the device in stance phase while standing and the user's weight is shifting from side to side, either to maintain balance or to make standing more comfortable. In many embodiments, allowing for relative rotation and/or motion of the prosthetic connector 1806' with respect to the socket lateral wall 1802' naturally helps with weight line positioning and provides some level of self-alignment in stance phase, both for static activities (such as standing) and for dynamic activities (such as walking).

The compliant linkages and/or compliant connectors can be made from a suitable compliant material such as rubber. In some embodiments, the compliant linkage is a medical-grade silicone rubber with a hardness of 85 Shore A, though other levels of hardness are possible. The compliant linkage and/or compliant connector can be a metal spring. The compliant connector is a type of compliant support and compliant member. In the illustrated embodiments, connector embodiments include a proximal connector 1805, 1805' coupled to the powered prosthetic thigh 1804 (or to a portion 1804' of the powered prosthetic thigh 1804), a counterpart 1806 (or a prosthetic connector 1806') coupled to the socket 1801, 1801', and a compliant component 1807, 1807'.

In some embodiments, the compliant component 1807, 1807' is designed in such a way as to limit the linear motion between the prosthetic connector 1806' and the socket lateral wall 1802', while allowing a few degrees of relative rotation to take place. In several embodiments, coronal and frontal planes rotation is preferred, while sagittal plane rotation is limited such as to optimize and/or facilitate the powered hip prosthetic design. (In several embodiments, coronal and frontal planes rotation is not preferred and sagittal plane rotation is not limited.) Sagittal plane relative rotation between the prosthetic connector 1806' and the socket 1801' contributes to the powered hip joint actuator compliance. Thus, in some embodiments, this sagittal plane relative rotation is accounted for in the motion and/or force control scheme to ensure proper system performance. In this context, limiting the connector compliance along this degree-of-freedom can be advantageous in some embodiments, but may not be necessary or advantageous in several embodiments.

Several configurations of the compliant connector may provide functionally equivalent devices to those previously described. Several embodiments use a rubber material, a resilient material, a polymeric material, and/or a combination of various materials (instead of the illustrated compliant component 1807') to connect the prosthetic connector 1806' to the socket 1801'. Some embodiments use selectively compliant mechanical structures for the compliant connector. In some embodiments, the compliant connector can include the proximal connector 1805, its counterpart 1806, and the intermediate compliant component 1807, 1807'. The intermediate compliant component 1807, 1807' can be located on either side of the proximal connector 1805 and its counterpart 1806. The intermediate compliant component 1807, 1807' can be coupled between the proximal connector 1805 and its counterpart 1806. Several embodiments include more than one intermediate compliant component 1807, 1807', For example, in some embodiments a powered prosthetic thigh 1804 includes a first intermediate compliant component and a socket includes a second intermediate compliant component.

Figure 19A:
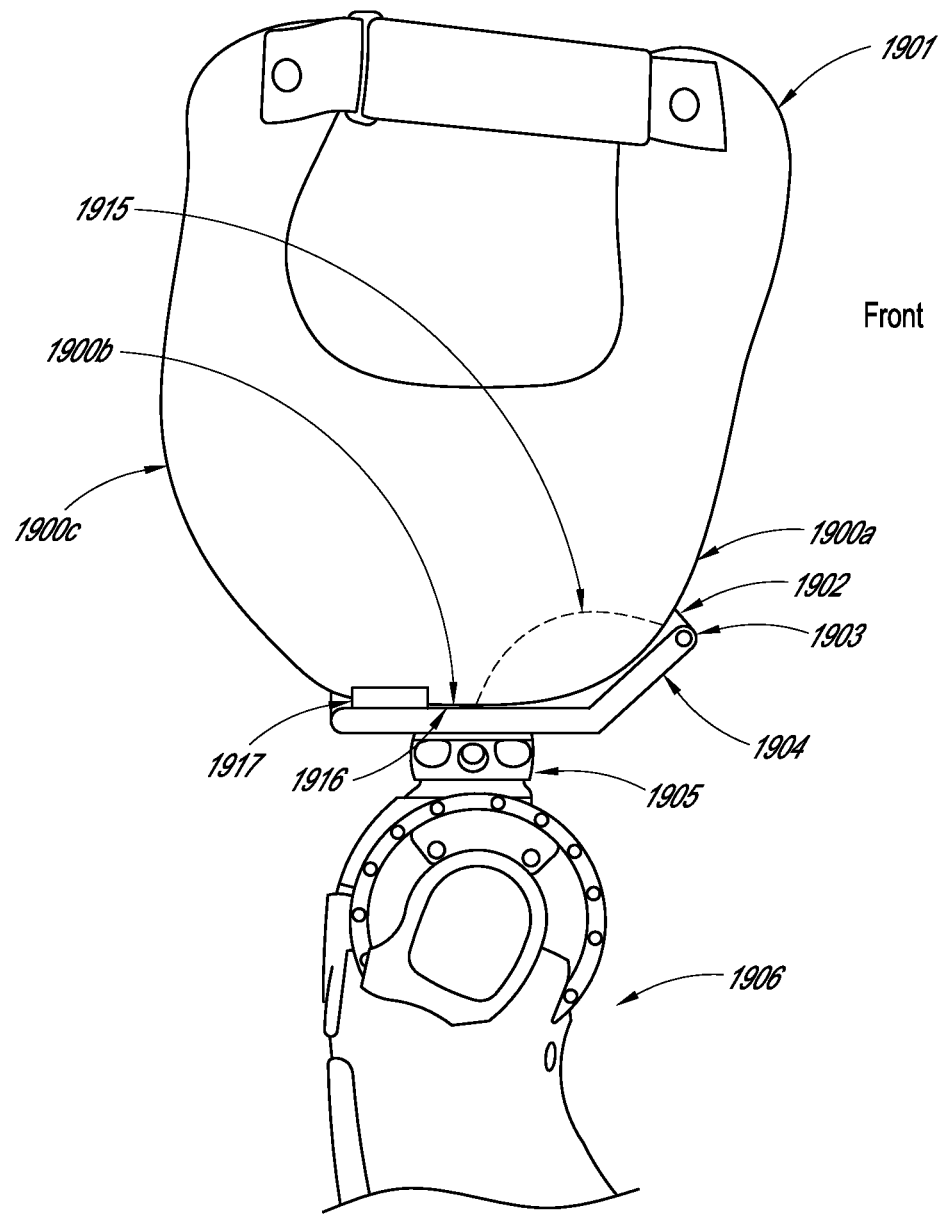
FIG. 19*a* is a schematic side view of a prosthetic hip joint embodiment attached to the front side of one embodiment of a socket.

FIG. 19a illustrates an embodiment of a mechanism for connecting a powered prosthetic thigh 1906 (such as the type illustrated in FIG. 5) to the front wall 1900a of a socket 1901. The illustrated embodiment is for amputees presenting a hip-disarticulation or hemipelvectomy amputation, although related embodiments are for other types of amputees. The illustrated socket 1901 includes front walls 1900a, a distal wall 1900b, and a back wall 1900c, although other embodiments are configured for sockets that have different wall configurations.

The illustrated mechanism allows moving the powered prosthetic thigh 1906 from underneath the socket 1901 when the user needs to sit, which can allow natural and comfortable sitting. In such a mechanism, the powered prosthetic thigh 1906 can be coupled to the socket 1901 through a pair of standard prosthetic connectors 1905 to an attachment arm 1904. The attachment arm 1904 can be formed in such a way as to follow the general contour of the socket's distal wall 1900b and front walls 1900a, when viewed in the sagittal plane. The attachment arm 1904 can be curved, straight, and/or angled. In some embodiments, the attachment arm 1904 forms an angle 1915 greater than 100 degrees and less than 160 degrees; greater than 90 degrees and less than 180 degrees; or greater than 120 degrees and less than 150 degrees.

The attachment arm 1904 can include an abutment section 1916, which can be located near the rear part of the distal section, such that the attachment arm 1904 can come in contact with the socket distal wall 1900b and/or with the socket 1901 when the user is standing. Furthermore, the attachment arm 1904 can include a pivot pin 1903, which can be located near one end of the attachment arm 1904. The pivot pin 1903 can be pivotably fixed using the mounting brackets 1902, which can be rigidly connected to the socket front wall 1900a. The mounting brackets 1902 and the pivot pin 1903 allow the attachment arm 1904 to rotate relative to the socket 1901, although some embodiments include a locking mechanism to prevent this rotation during certain times, such as when the user is standing or walking without attempting to sit down. In many embodiments, rotation of the attachment arm 1904 allows moving the powered prosthetic thigh 1906 away from the distal wall 1900b. This rotation can also enable the powered prosthetic thigh 1906 to move in front of the socket 1901. In several embodiments, the rotation enabled by the system allows the powered prosthetic thigh 1906 to completely clear the area beneath the distal wall 1900b such that the distal wall 1900b and/or the area beneath the distal wall 1900b can be used for sitting.

This type of embodiment can be advantageous when used with a powered hip prosthesis that does not provide a specific sitting-down and/or standing up function (e.g., power dissipation and/or hip flexion control in sitting-down; power generation and/or powered hip extension in standing-up). In this context, use of a simpler embodiment of the powered hip prosthesis is feasible and can be implemented using a frontal wall socket connection. This type of connection can be interchangeable with other types of hip prosthetic connection systems, and thus, allows use of this type of device for gait rehabilitation and training without requiring construction of a new socket. The preceding examples should not be interpreted in a limiting sense. For example, this type of embodiment can also be advantageous with other types of hip prostheses. Simpler embodiments of powered hip prostheses are feasible in other contexts. Some embodiments require construction of new sockets.

Although some embodiments do not have a mechanism for ensuring the attachment arm 1904 will remain in place during prosthetic device operation (such as walking and standing), other embodiments include a mechanism for ensuring the attachment arm 1904 will remain in place during prosthetic device operation The abutment section 1916 provided on the attachment arm's 1904 rear distal section can allow for positive contact between the attachment arm 1904 and the socket 1901. However, some embodiments benefit from additional containment of the attachment arm 1904 due to the relatively large acceleration levels found at hip level during, for example, swing phase of level walking gait. Such containment can be achieved in a number of ways.

Several embodiments allowing such containment are created by the addition of a manually actuated friction break at the pivot pin 1903 such that when activated, a friction force is created between the mounting brackets 1902 and the attachment arm 1904, and/or between the pivot pin 1903 and the mounting brackets 1902. An alternative embodiment of a locking mechanism to prevent and/or limit rotation of the attachment arm 1904 relative to the socket 1901 is created by using cam actuated pressure. The cam actuated pressure can act on each end of the pivot pin 1903, coupled to male-female mating features located on the internal face of the mounting brackets 1902 and on the external edges of the attachment arm 1904. FIG. 19a illustrates a lock 1917, which couples the socket 1901 to the attachment arm 1904 such that when locked, the lock 1917 prevents the socket 1901 from moving away from the attachment arm 1904. In some embodiments, the lock 1917 is a mechanical latch, which can be an electronically actuated mechanical latch. In some embodiments, the lock 1917 is a magnetic latch and/or a magnetic holding assembly.

Increased retention force on the attachment arm 1904 can also be generated by slightly changing the shape of the attachment arm 1904 in the location of the pivot pin 1903. This change can lead to an increase in contact area between the mounting brackets 1902 and the pivot pin 1903 and/or an increase in contact area between the mounting brackets 1902 and the attachment arm 1904.

Figure 19B:
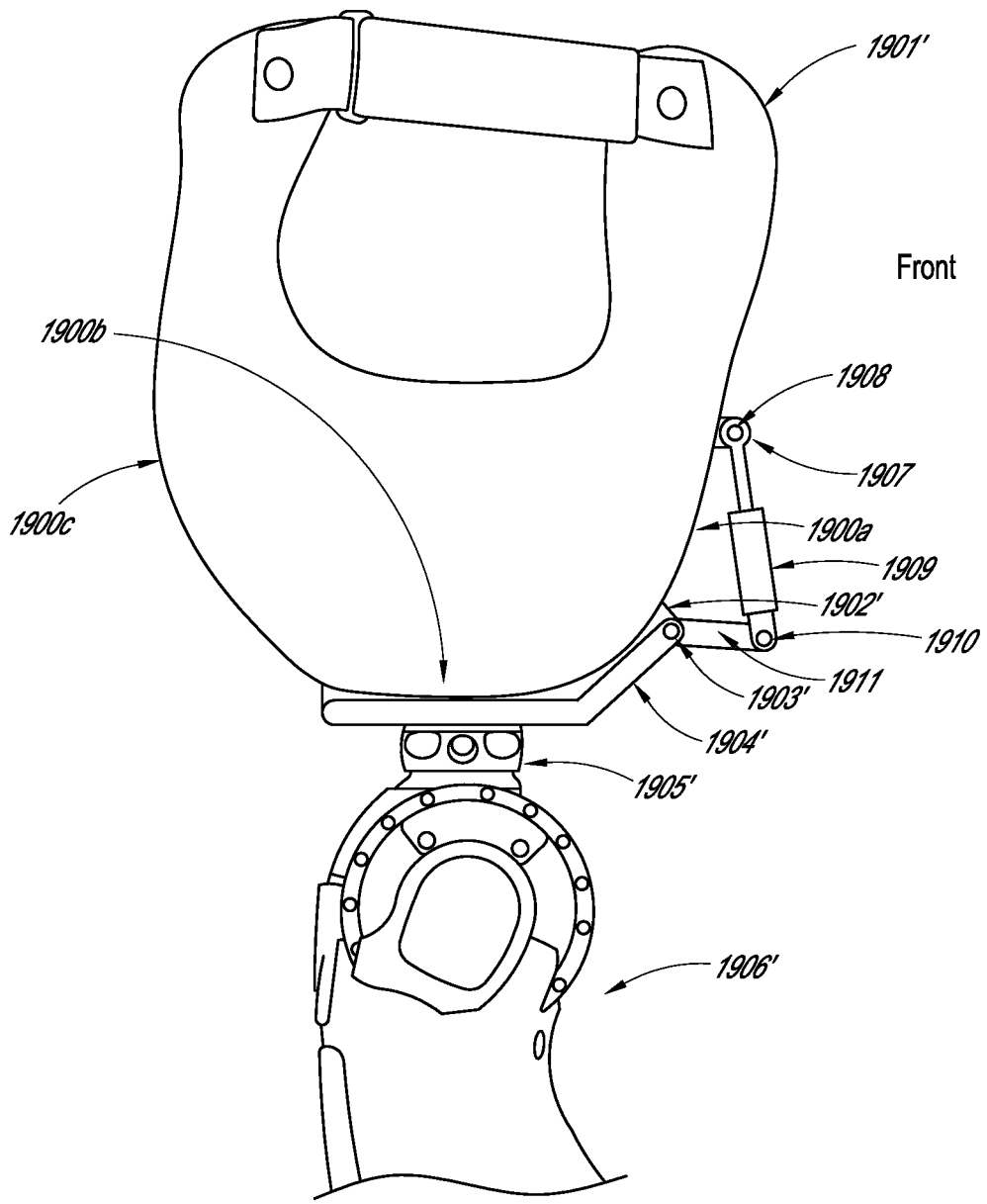
FIG. 19*b* is a schematic side view of a prosthetic hip joint embodiment attached to the front side of a socket with a hydraulic or pneumatic locking mechanism, according to one embodiment.

FIG. 19b illustrates an alternative embodiment of a containment mechanism to ensure that the attachment arm 1904' remains in position while the prosthetic hip device is operated. The powered prosthetic thigh 1906' is connected to an elongated attachment arm 1904' comprising a distal part and a frontal part that are operatively connected together in such a way as to follow the contour of the socket 1901' when viewed in the sagittal plane. Connection of the powered prosthetic thigh 1906' to the attachment arm 1904' is achieved using a pair of mating prosthetic connectors 1905' The attachment arm 1904' is coupled to the front wall 1900a of the socket 1901' through a pivotable joint implemented by a pivot pin 1903' and mounting brackets 1902'

An offset lever 1911 is fixed to the attachment arm 1904', In some embodiments, the offset lever 1911 is part of the attachment arm 1904'. In several embodiments, the offset lever 1911 extends away from the socket 1901' The offset lever 1911 can be fixed to one end and/or to the frontal part of the attachment arm 1904'. The offset lever 1911 can include a pivotable joint, which can be located on an end portion of the offset lever 1911. An actuator 1909 is coupled through a mounting pin 1910 to the pivotable joint of the offset lever 1911. The actuator 1909 can be a manually actuated hydraulic or pneumatic actuator. The actuator 1909 can be automatically controlled by a control system.

The actuator 1909 can include a piston that can move inside of a cylinder, which can create two separate chambers. The cylinder can be rigidly, yet pivotably, connected to the offset lever 1911 through the mounting pin 1910. The piston can be rigidly connected to a rod that in turn connects to a mounting bracket 1907 through a second mounting pin 1908. Mounting bracket 1907 can be coupled to the front wall 1900a of the socket 1901' in a location generally positioned more proximally than the lower mounting bracket 1902'.

Other embodiments include different types of actuators, different types of levers, different mounting devices, and different mounting positions. In several embodiments, the offset lever 1911 cannot move relative to the attachment arm 1904' In other words, the offset lever 1911 can be rigidly fixed relative to the attachment arm 1904'.

As discussed above, the actuator 1909 can be a hydraulic or pneumatic actuator and/or can be equipped with a manual actuator. In some embodiments, the manual actuator, depending on its position, can either allow fluid to flow freely between the two chambers of the actuator or can fully prevent the fluid from flowing between the chambers. For example, the actuator can prevent fluid flow between the chambers when the piston is moved under the influence of an external force (e.g., such as a force from the user's hand). In several embodiments, the user can move the actuator to the open position to allow fluid flow between the chambers of the actuator, and thus, can unlock the attachment arm 1904' from its position. Unlocking the attachment arm 1904' can be desirable in order to move the powered prosthetic thigh 1906' from underneath the socket 1901' and/or to move the powered prosthetic thigh 1906' from a sitting position to a position where the powered prosthetic thigh 1906' is underneath the socket 1901'. The user can move the manual actuator to the locked position to lock and/or secure the attachment arm 1904' and/or powered prosthetic thigh 1906' underneath the distal wall 1900b and/or underneath the socket 1901' (e.g., for operation in walking or standing). The user can also move the manual actuator to the locked position to lock and/or secure the powered prosthetic thigh 1906' in the sitting position and/or such that the powered prosthetic thigh 1906' is in front of the socket 1901'. Several embodiments include a progressive manual actuator that allows the user to open actuator part way and/or adjust the damping behavior of the progress manual actuator such that the user can select the resistance of the actuator to movement between the socket 1901' and the attachment arm 1904'. This embodiment can be advantageous to help the user gradually sit down rather than having the system either be completely locked or completely loose.

FIG. 20 presents typical hip joint data associated with level walking by non-amputated subjects. This data is from Winter, D. A., *The Biomechanics and Motor Control of Human Gait*, University of Waterloo, Ontario 1987 (herein "Winter 1987"). Joint data varies based on many factors including subject differences and activity differences. The following description is provided because some embodiments mimic the approximate behavior described herein. For example, some of the prosthetic embodiments mimic the behavior represented in FIG. 20. Several embodiments mimic the behavior illustrated in FIG. 20 within +/−15%, +/−25%, +/−40%, and/or +/−55% of the y-axis in one or more of the plots as measured based on the stride percentage. For example, an embodiment that mimics a behavior within +/−40% will typically have a y-axis value within +/−40% at each stride percentage. Several embodiments mimic the behavior illustrated in FIG. 20 by having a mean deviation from the y-axis values that is within +/−15%, +/−20%, +/−30%, and/or −/−40%.

All variables are plotted as a function of the normalized stride duration, expressed in percentage of the complete stride duration. Heel strike occurs at 0% stride duration. The first plot (at the top of FIG. 20) represents the vertical component of the ground reaction force normalized with respect to test subject body mass (in N/kg) plotted for a complete stride. Vertical ground reaction force component reached a null value at 64% of the stride duration, which indicates completion of the transition to swing phase.

The second plot represents the hip joint angle, which is defined as the relative angle between the user's trunk and thigh segments. Zero degrees indicates that the thigh segment is aligned with the trunk segment. Hip flexion is defined as a positive angle, while extension is defined as a negative angle.

The third plot represents the hip moment normalized with respect to body mass and expressed in N m/kg. According to usual conventions, a positive hip moment causes a positive hip joint velocity and/or an increase in hip joint velocity, while a negative hip moment causes a negative hip joint velocity and/or a decrease in hip joint velocity.

The fourth plot (at the bottom of FIG. 20) represents the hip joint power normalized with respect to user's body mass and expressed in W/kg. A positive hip joint power indicates that power is generated by the joint, while a negative power indicates that power is dissipated by the joint.

Hip joint behavior throughout a complete stride in level walking can be analyzed as follows. At foot strike, the hip joint is flexed to a level close to its maximum while the moment is negative. The moment then quickly rises to maximum amplitude following foot strike occurrence. A combination of negative velocity (i.e., flexion level is decreasing) and negative torque leads to a positive power, which is representative of power being generated by the joint. For a short period of time following foot strike, joint torque becomes more negative as the load increases during weight acceptance, which drives the positive power up. In that context, it is to be understood that the hip joint is actually extending under power and the torque is reducing towards a null value while the joint speed increases to a fairly constant level.

Hip joint power becomes negative (i.e., power absorption) at about 20% of the stride due to joint velocity still being negative and torque transitioning to positive values. This situation indicates the end of the weight acceptance part of the stride cycle for the hip joint, which will now adopt a new behavior in order to carry the body center of mass over the prosthetic limb. Hip behavior is now concerned with regulating flexion torque under dissipative power to achieve full hip extension in a smooth and uniform manner. This sequence can be performed under fairly constant dissipative power levels and can last until approximately 52% of the stride cycle, which matches the point at which maximum hip extension is achieved and hip flexion starts taking place, while the prosthetic foot is still loaded and generative power is observed.

Maximum generative power is observed to take place at approximately 62% of the stride cycle, which typically occurs more or less simultaneously with swing phase. Generative power burst is required in order to accelerate the lower-limb to proper flexion speed and position. Hip joint swing flexion is more or less completed at approximately 80% of the stride, where hip angle and velocity are observed to stabilize to a constant level. However, it is to be noted that significant negative torque typically occurs from that point until the next foot strike, which is associated with non-negligible generative power. Hip joint extension torque and generative power are often required to slightly extend the hip right before the upcoming foot strike and also to manage the inertial loading caused by the knee extension motion deceleration. Of note, several embodiments do not mimic the behavior described in relation to FIG. 20.

Figure 21:
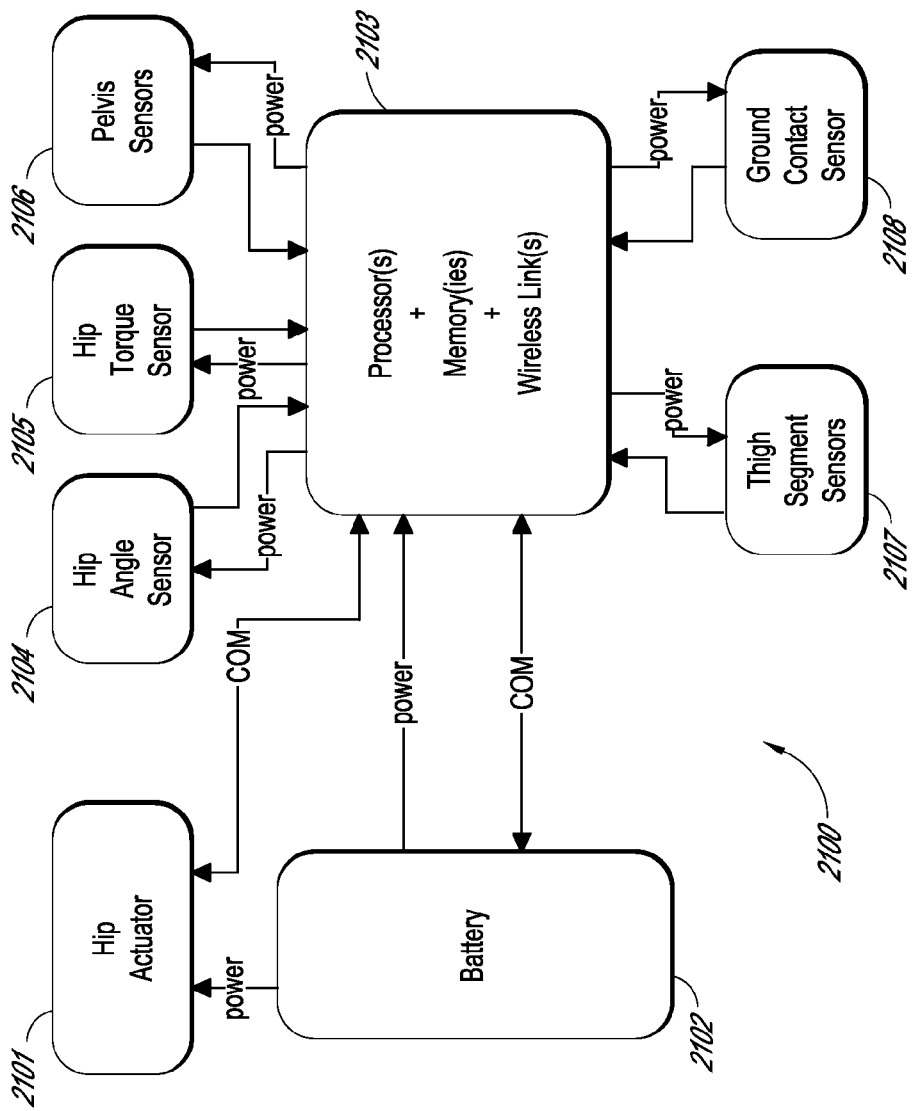
FIG. 21 is a schematic representation of hardware system architecture for a powered hip prosthetic device with a single-joint, according to one embodiment.

FIG. 21 is a schematic representation of a hardware system architecture embodiment 2100 of a single-joint, powered or passive, hip prosthetic device. The system herein illustrated includes many of the basic modules previously highlighted in the mechanical embodiments. The powered or passive, hip prosthesis includes a hip actuator 2101, a battery 2102, a processor 2103, and sensor modules 2104, 2105, 2106, 2107, and 2108. The processor 2103 can include processors, computer memory, and/or wireless components.

The actuator 2101 can be designed using various technologies and be of a passive nature (i.e., the actuator can dissipate energy, but cannot generate mechanical power or motion) or of an active nature (i.e., the actuator can generate mechanical power and/or motion). The actuator 2101 can have a combination of a passive nature and an active nature (e.g., a breaking system with spring return function and/or a four-quadrant electrical motor based system). The actuator 2101 can be coupled to the rest of the system architecture 2100 through two or more functional links. Power can be directly provided to the actuator 2101 by the battery module 2102 in order to minimize the current path and avoid contaminating other electronic functions with electrical noise. Furthermore, the hip actuator module 2101 can be functionally coupled to the processor 2103 through a bi-directional communication interface (represented by lines connecting the modules of the system architecture 2100). Of note, while this type of interface can be implemented as a high-level digital interface, it is also possible to implement this last COM interface through a low-level analog interface, where actuator commands are directly sent as analog signals, voltage, or current coupled. In the case where a digital interface is utilized, a local processor or transmitter can be used to convert the high-level message sent by the processor 2103 into low-level commands. Similarly, low-level feedback generated by components (e.g., of the actuator module 2101) can be processed locally and translated into high-level messages before being sent to the processor 2103.

The battery module 2102 can provide power to all other modules in the system and can be a removable battery pack, such as the battery pack 300 shown in FIG. 2. The battery module 2102 can be configured as a smart battery. The smart battery configuration can allow the battery to implement all the basic safety and management features required by advanced battery chemistries, while minimizing the interface requirements between the battery and the processor executing the powered hip process application. To that effect, a bidirectional communication link can be implemented between the battery 2102 and the processor 2103 to allow exchange of information between the modules. Typical information exchanged between the battery 2102 and the processor 2103 in the context of the operation of the hip prosthesis includes, but is not limited to, the battery state-of-charge, the battery general health state, the battery voltage, temperature, and/or discharge current. Furthermore, the processor 2103 can provide commands and/or information to the battery module 2102 through the same interface. Commands generated for the battery module 2102 by the processor can include, but are not limited to, power-off commands, minimum acceptable state-of-charge level for discharge, and/or power-on commands. Information provided to the battery module 2102 by the processor 2103 can include, but is not limited to, expected maximum discharge current, ambient temperature, and/or maximal charge voltage.

The processor module 2103 can serve as a module used to regroup all common services required to implement the complete system functions related to long-term field operation, including processors, memory devices, wireless communication links, real-time clocks, field-programmable gate arrays, oscillators and clock circuits, audio feedback devices, visual feedback devices, vibrator feedback devices, low-voltage power supplies, standby batteries, communication interfaces for sensors/actuator modules, and/or power/interfaces switches. From an architectural standpoint, the processor module 2103 can be the common connection point for all the sensor modules, which can be directly interfaced. The onboard processor can be responsible, as part of the prosthetic hip software and/or firmware routine, for collecting the information generated by the sensors and processing it in such a way as to generate an appropriate output signal to be used to command the actuator 2101, or another module, in a timely and repeatable manner.

Multiple sensor modules can be used to generate the information required by the system in order to sustain prosthetic hip operation. Based on the device functional and performance requirements, the system architecture can be built around one or many sensor modules. Sensor modules can be used to directly monitor kinematic variables that are either internal to the prosthetic system (e.g., hip angle sensor 2104 or hip torque sensor 2105) or external to the prosthetic system (e.g., gait related variables such as pelvis velocity and acceleration). Similarly, non-gait related variables can also be monitored as part of the prosthetic system operation. Such variables include, but are not limited to, battery current, actuator power, impact amplitude and/or maximum stress in structural components. Furthermore, kinematics sensors can be positioned directly on the thigh segment in order measure segment angular speed, angular acceleration, and/or linear acceleration at specific points of the thigh segment structure. Ground contact sensing is also possible in order to determine in real-time whether the prosthetic foot is in contact with the ground or is in swing phase.

The System architecture 2100 illustrates a centralized processor architecture, where the processor 2103 is central in the architecture and interfaces with all modules contained in the specific system definition. This particular hardware architecture embodiment provides the benefits of presenting a very low foot print and minimizing the overhead associated with interfacing and synchronizing multiple devices and/or processors. Sufficient scalability can also be achieved through the use of adequate components to allow for the addition or removal of peripheral modules without directly affecting the processor operation and/or configuration. In some embodiments, use of a memory-mapped, field-programmable gate array as an interface front-end provides the necessary scalability and isolates the processor from directly interfacing the peripheral modules. Furthermore, it is to be noted that based on the mechanical embodiment of the system architecture 2100 illustrated in FIG. 21, it is possible to mount a certain number of sensor modules directly on the processor 2103 printed-circuit board. Colocation of the processor 2103 and one or many sensor modules on the same printed-circuit board can greatly reduce the device cost, as well as the complexity of the interconnections to manage during device manufacturing and assembly.

Figure 22:
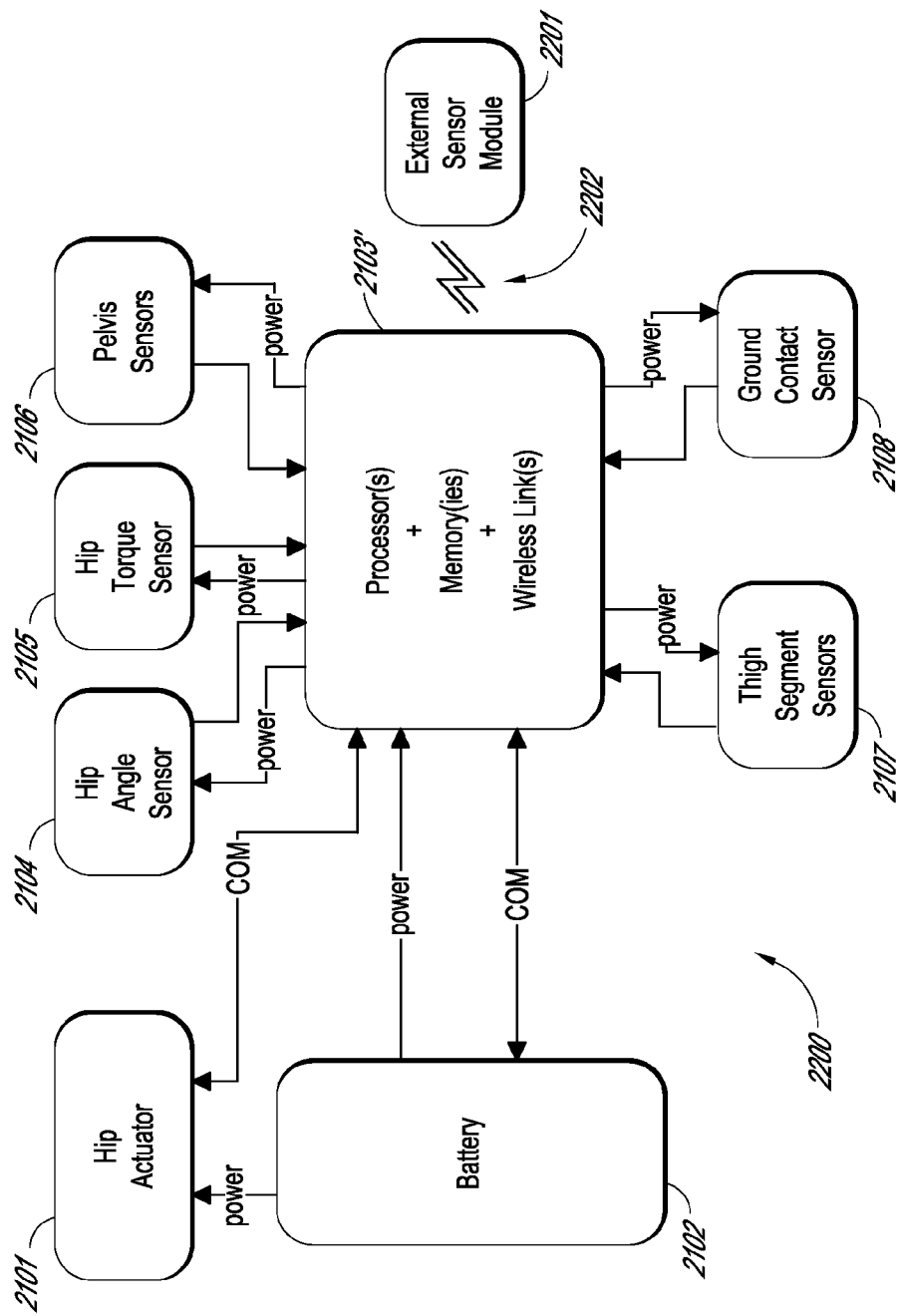
FIG. 22 is a schematic representation of hardware system architecture for a powered hip prosthetic device with a single-joint and an external sensor, according to one embodiment.

FIG. 22 presents an alternative embodiment of the previous hardware system architecture. This schematic representation of a powered hip prosthetic hardware system architecture 2200 generally includes building blocks that are similar to the building blocks introduced in FIG. 21. This embodiment includes an additional external sensor module 2201, connected to the processor module 2103' through a bidirectional wireless communication link 2202. It is to be noted that the connection of the external sensor module 2201 to the processor module 2103' and/or embedded processor is not a strict requirement. Each element of the various hardware system architecture embodiments described herein is optional.

Several embodiments achieve the same functionalities using other types of bi-directional communication links, such as an optical link, or a wired link. Several embodiments for the use of an external sensor module 2201 make use of a bi-directional wireless communication link 2202. From a convenience standpoint, it is sometimes simpler and more efficient to locate the processor module 2103' in the thigh segment of the prosthetic hip device itself (although not all embodiments are configured this way). On the other hand, there is a benefit in not constraining the external sensor module 2201 to be located in, or on, the prosthetic hip device itself. Hence, greater flexibility and convenience are achieved in several embodiments through the use of one or more wireless links.

The external sensor module 2201 can be used in the architecture in order to provide additional data to the prosthetic system. This data can be data that would typically not be possible to monitor from the device itself due to its physical location or due to the nature of the data. Furthermore, it is possible to use the external sensor module 2201 to collect and transfer sensor data to the processor module 2103' that is typically not required for device operation, but provides insights on the device's operation from functional, clinical and/or performance standpoints. The data transfer can be to processors and/or memories of the processor module 2103'.

The following paragraphs describe additional non-limiting embodiments regarding example external sensor module 2201 data and usages.

In one embodiment, the external sensor module 2201 is an upper body kinematics and dynamics sensing module communicating to the prosthetic hip device using a Bluetooth Low-Energy communication link Due to the high functional loss associated with hip-disarticulation and/or hemipelvectomy amputations, many users are observed to experience difficulties in initiating walking, as walking initiation often requires the user to commit his whole upper body and center of mass to move over the prosthetic limb. In that context, functional outcome improvements can be obtained by directly monitoring the user's upper body kinematics, dynamics, and/or orientation changes as the user initiates forward progression. For example, advantageous use of contra-lateral arm motion at gait initiation can be made in order to modify the prosthetic hip device behavior to properly sustain the transition from standing to walking. This last detection scheme relies on the natural gait pattern where arms swing back and forth during walking as a way to maintain dynamic balance.

Similar detection of the transition from standing to walking can also be performed by monitoring upper body posture and its changes as the user initiates walking. Forward leaning of the upper body can indicate a need to flex the hip while in swing phase, either to allow stepping forward to initiate walking or stepping forward to regain balance while standing. This information and the use of the external sensing module 2201 can either be associated with normal operation of the prosthetic hip device for control purposes or can be associated with a special training mode where the additional information provided by the external sensor module 2201 is used in order to facilitate training with the device until sufficient control is achieved by the user. Furthermore, use of such an external sensing module can also be used during normal device operation for specific functions, such as detecting and preventing falls or loss of balance, or monitoring occurrences of such events for data logging purposes.

In a further embodiment, the external sensor module 2201 is sound limb kinematics and dynamics sensing module communicating to the prosthetic hip device using a Bluetooth communication link. Use of sound limb kinematics and/or dynamics data can improve the overall consistency and performance of the control system when operating in cyclical gait. Collection of sound-limb kinematics, dynamics, and/or ground contact data can help perform real-time monitoring of the complete gait quality and overall device impact on user gait. The external sensor module can then be used to that effect, either as a temporary integration for gait quality measurement purposes or as a long-term integration for monitoring of gait quality progression and device usage compliance. Such use of the external sensor module typically provides generally complete gait quality assessment under normal device operating conditions. In this operational context, the external sensor module records and transmits the data to the prosthetic processor 2103' whether or not it is merged to the prosthetic device's embedded data streams and saves to non-volatile memory for later retrieval and analysis.

In several embodiments, the external sensor module 2201 is an advanced pedometer that measures gait activity and transfers information to the prosthetic hip device for long term monitoring of device usage. Under such an operational paradigm, it is possible to minimize throughput of the communication link by only transferring the high-level data from the pedometer, instead of the raw sensor information as illustrated in the previous embodiment. Hence, the pedometer can connect to the prosthetic device through the wireless communication link and transfer collected information either in a synchronous or in an asynchronous manner to the processor module for storage in non-volatile memory and later retrieval. Typical data collected and transferred by the pedometer could include, but is not limited to, number of steps performed, average linear speed, maximum linear speed, walking steps speed distribution, active use time, passive use time, and/or shock levels at foot strike. An example of a pedometer device that could be integrated in an external sensor module is a Patient Activity Monitor (PAM) made by Ossur.

In some embodiments, the external sensor module 2201 can be a heartbeat monitor module communicating to the prosthetic hip device using an ANT communication link. This type of embodiment makes advantageous usage of the features associated with the ANT communication protocol, where devices will automatically link up to the host when they are discovered to be in close enough proximity. Under such a paradigm, external sensor modules dynamically link to the prosthetic device system architecture, based on their proximity. Furthermore, such types of ad-hoc architecture construction can be optimal for temporary use of sensor modules aimed at providing gait quality assessment data or additional sensor input for user training purposes in a temporary manner. While this embodiment is exemplified through the use of the heartbeat monitor, this is not considered a strict limitation on the nature of the sensor modules that can be dynamically linked into the prosthetic device architecture using the paradigm described herein. Other sensor modules providing kinematic, dynamic, and/or physiological data, like electromyography, body temperature, blood oxygen levels, and/or nerve conduction velocity, can also be used in order to implement similar functions.

In a further embodiment, the external sensor module 2201 is a GPS enabled location finding module that can transmit information about location and movement of the user in a global positioning system to the prosthetic hip device using an RF communication link or a GSM communication link. Under such embodiments, the data collected by the system can be used by healthcare personnel to monitor compliance of the patient during gait rehabilitation, either in real-time using the GSM link or at periodical intervals by retrieving the data previously saved to the prosthetic device's non-volatile memory, which can be integrated in the processor. Data transferred via such external sensor modules could then include the physical location of the device, the distance covered using the device for a given period of time, the average speed of progression measured during ambulation, the maximum speed of progression measured during the ambulation, and/or the nature of the terrain encountered during ambulation.

While various types of sensors and/or sensor technologies can be used for the embodiments described above, key considerations can include the sensors' power consumption and bulk. Since the external sensor module needs to be relatively small and be able to operate in a stand-alone manner for a period of time ranging from a few hours to many days, power consumption and capacity to enter standby mode when periods of inactivity are detected are beneficial in some embodiments. Kinematics parameters can be measured using various sensors type, such as rate gyros, inclinometers, goniometers, magnetometers, and/or velocity sensors. Dynamics parameters can be measured using a wide variety of sensors, such as accelerometers, load cells, strain gauges, shock sensors, and/or pressure sensors. Other types of sensor data can also be collected for purposes of measuring gait quality and/or changes in gait quality, Namely, blood-oxygen sensors, various types of electromyography sensors, temperature sensors, and/or heartbeat monitoring sensors can all be used to monitor various aspects of the gait quality. Information from the sensors can be transferred to the prosthetic device to be merged with the prosthetic device data and saved to a memory for later retrieval.

Figure 23:
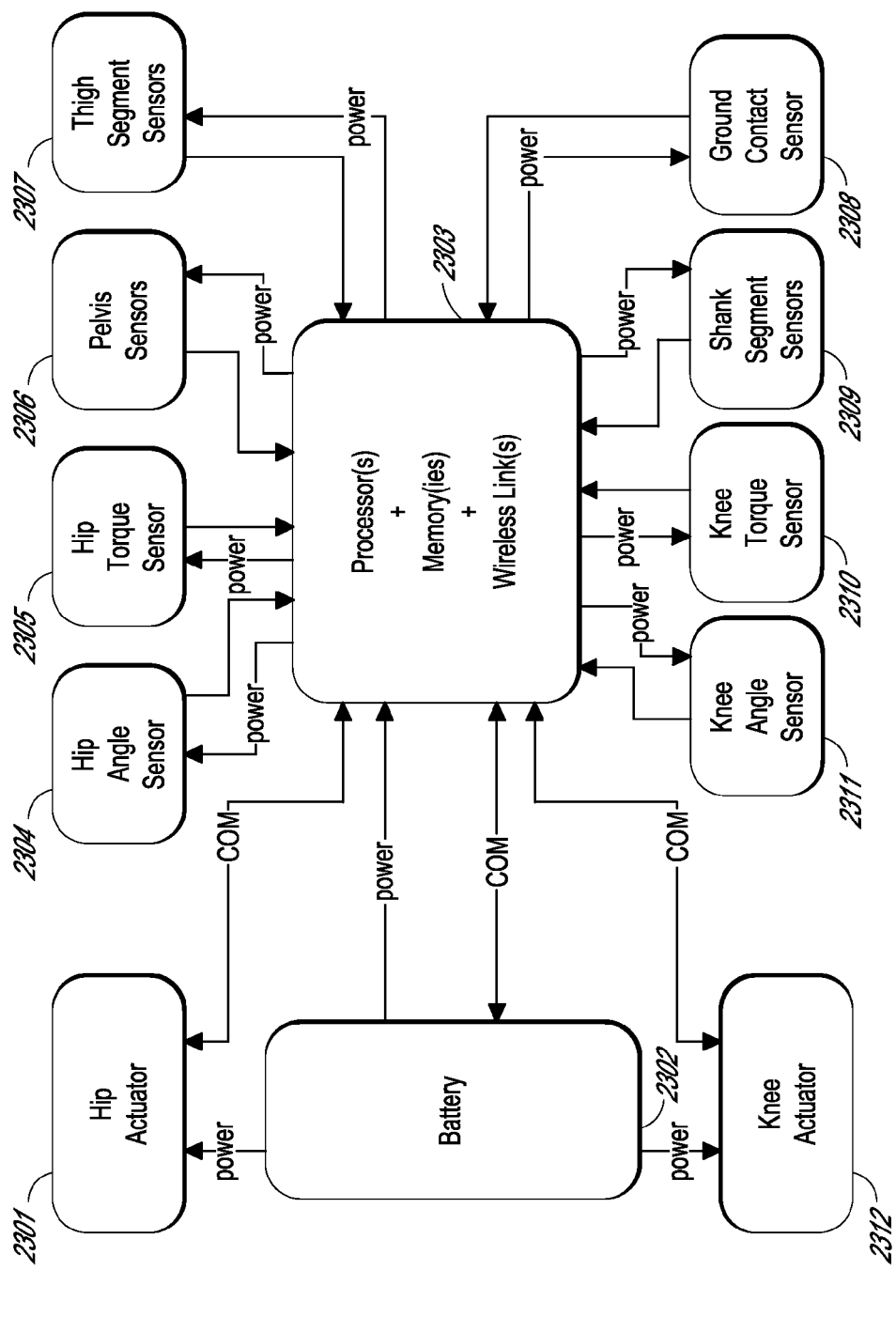
FIG. 23 is a schematic representation of hardware system architecture for a powered hip prosthetic device with dual-joints, according to one embodiment.

FIG. 23 illustrates a hardware system architecture embodiment for a dual-joint, battery-operated, thigh-segment prosthetic device. This embodiment is similar in nature and implementation to the embodiments previously introduced for a single joint powered hip prosthetic device. Hardware system architecture 2300 makes use of a centralized processor platform, located on the processor module 2303, in order to control all degrees-of-freedom associated with the device. The processor module 2303 can be an electronic platform module in each embodiment described herein. All sensor modules (e.g., a hip angle sensor 2304, a hip torque sensor 2305, pelvis sensors 2306, thigh segment sensors 2307, a knee angle sensor 2311, a knee torque sensor 2310, shank segment sensors 2309, a ground contact sensor 2308) can also be directly linked to the centralized processor(s). Under such an architectural paradigm, it is possible to implement synchronized control of the device's two degrees of freedom and ensure that optimal synergy and coordination between the two joints is achieved during ambulatory or non-ambulatory tasks. Hardware system architecture 2300 also includes a hip actuator 2301, a battery 2302, and a knee actuator 2312.

Figure 24:
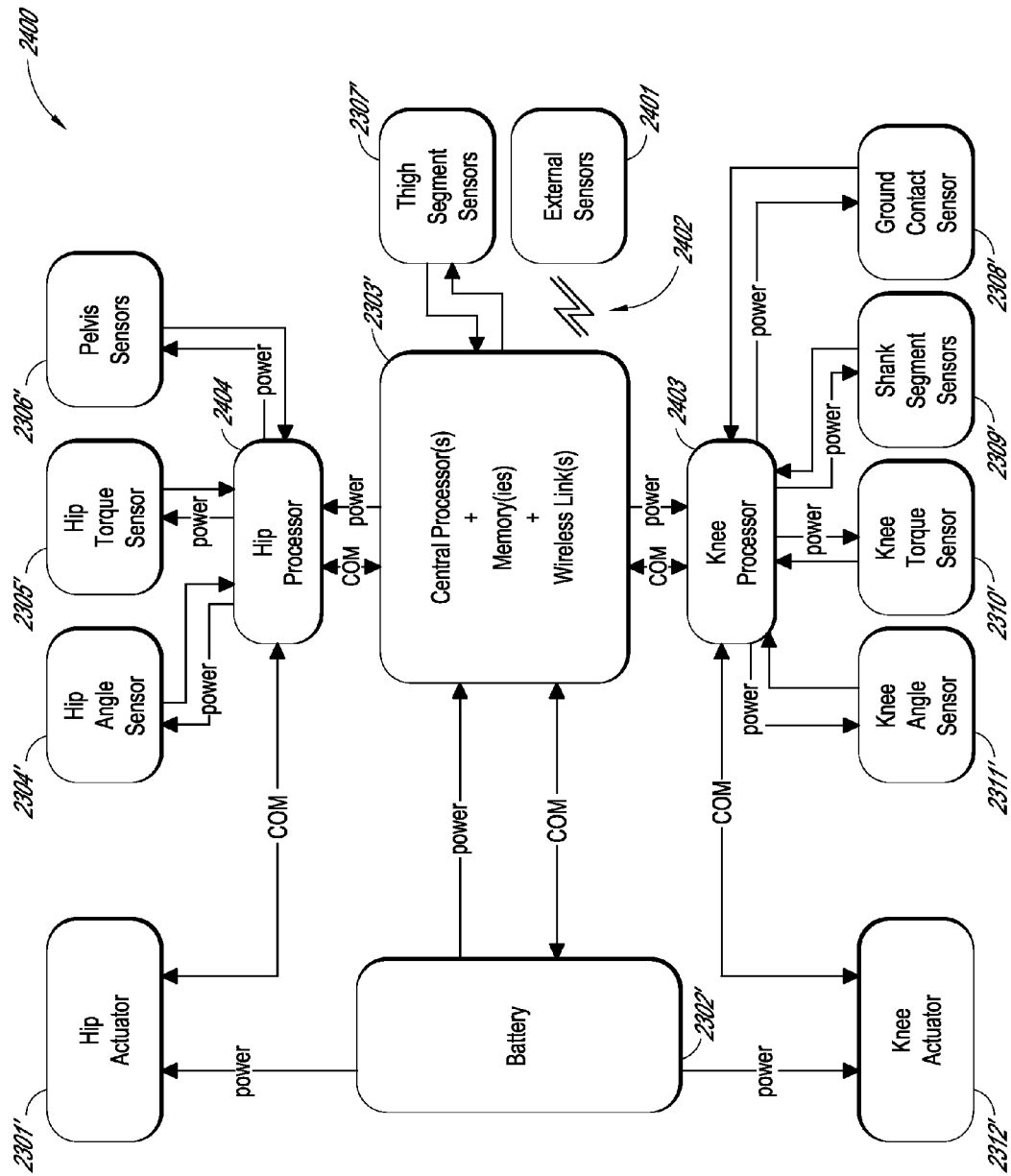
FIG. 24 is a schematic representation of hardware system architecture for a powered hip prosthetic device with dual-joints and distributed processing, according to one embodiment.

FIG. 24 illustrates a hardware system architecture embodiment 2400 for a dual-joint, battery-operated, thigh-segment prosthetic device where a central processor 2303' is coupled to independent processors 2403, 2404 for each degree-of-freedom. Under such an architecture, the central processor 2303' can manage and coordinate all the devices' services that are not typically related to the operation and motion control of the joint themselves, while the joint dedicated processors 2403, 2404 handle the joint motion control and local sensor modules with which they interface. This way, it is also possible to implement both joint as independent devices, as synchronized devices, and/or as coordinated devices depending on the level of interaction that is desired between the two joints.

The hip processor 2404 can interface directly with the hip actuator 2301', a hip angle sensor 2304', a hip torque sensor 2305', and/or pelvis sensors 2306' The knee processor 2403 can interface directly with the knee actuator 2312', a knee angle sensor 2311', a knee torque sensor 2310', shank segment sensors 2309', and/or a ground contact sensor 2308'. All modules can interface through a bi-directional wireless communication link 2402 and/or through multiple wireless communication links 2402.

Such architecture can also be implemented across multiple physical printed-circuit boards, for example, in the case where the mechanical embodiment constraints would yield a more efficient package with the printed-circuit board and control system being sub-divided to match the physical constraints. For example, such a hardware system architecture can be used in a mechanical embodiment such as the one illustrated in FIG. 17. It is also possible using this type of architecture to have sensor modules, such as the external sensor module 2401 and/or the thigh segment sensor module 2307', connected directly to the central processor 2303' for device control purposes and/or for data logging purposes. This approach also enables the implementation of different control schemes where both local and central schemes can be implemented in parallel using different information sources and where automatic switching between local and central control is performed based on the identified device use scenario.

Figure 25:
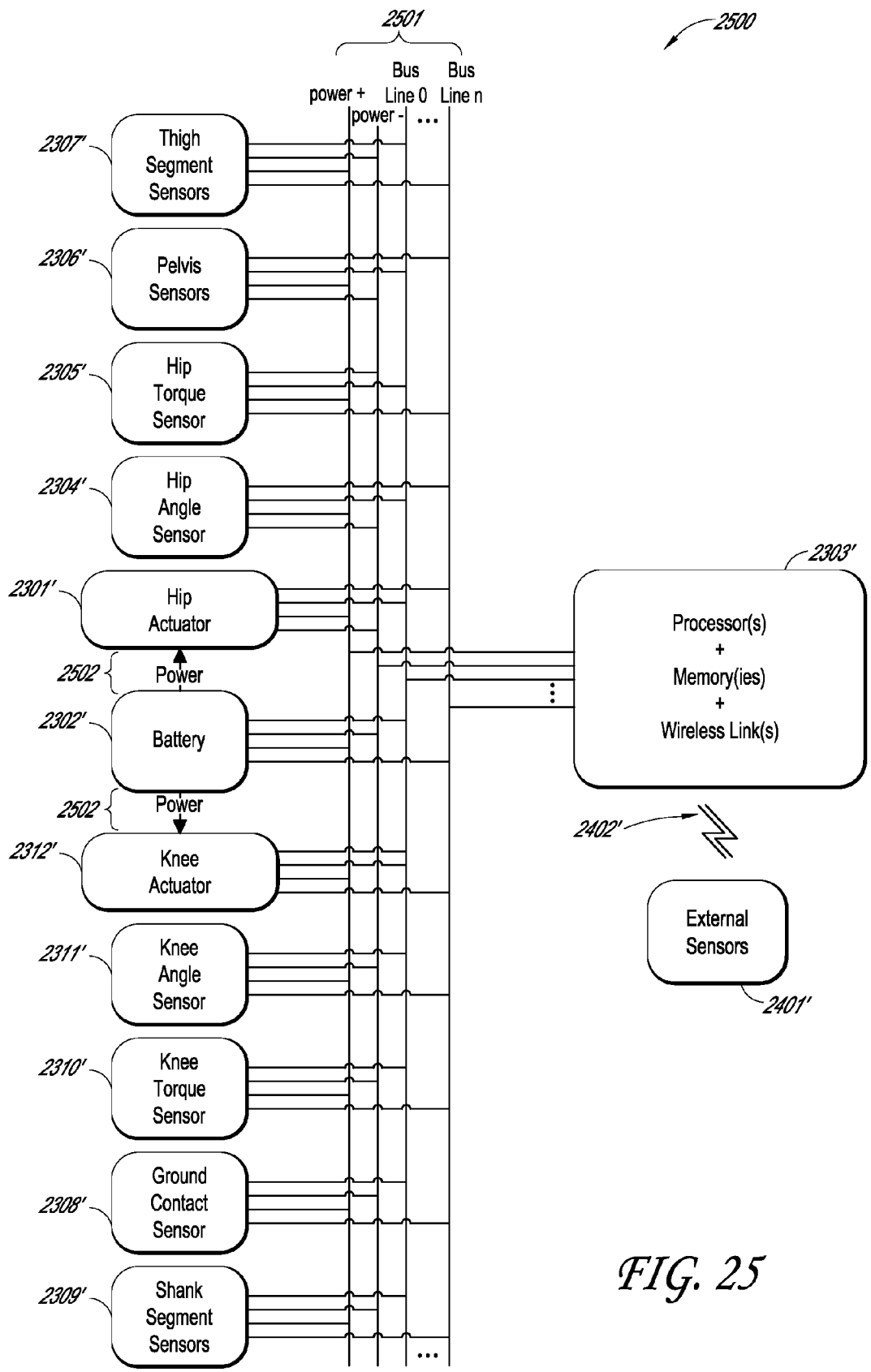
FIG. 25 is a schematic representation of hardware system architecture for a powered hip prosthetic device with dual-joints, a common bus, and a central controller, according to one embodiment.

FIG. 25 illustrates a hardware system architecture embodiment 2500 for a dual-joint, battery operated, thigh-segment prosthetic device similar to the embodiment previously introduced in FIG. 23. In this embodiment, centralized processor architecture is implemented, but a power and data bus 2501 is used to interface the sensor modules and actuator modules to the processing platform and/or the electronic platform module 2303'. Of note, in some embodiments, the power bus is typically configured for the low-power supplies required by the sensor and actuator control circuit, and is not typically configured for the high power requirements of the actuators themselves (illustrated as separate functional connections 2502). Based on the exact definition of the system and the communication protocol implemented on the bus data lines, the data bus width can be adjusted to accommodate for the most efficient scheme. Examples are numerous of communication protocols that can be used on data buses of this type via system hardware architecture embodiments (e.g., SPI, I²C). In some communication protocols that can be used with various data bus embodiments, specific data bus lines are reserved for directly addressing devices. In some other communication protocols, the bus devices are addressed by digital addresses incorporated in the message being transmitted over the bus itself, allowing for each device to listen and decide whether the message is applicable or not.

As previously introduced with other embodiments of the system hardware architecture, the electronic platform module 2303' and its processor(s) can be used to interface external sensor modules 2401' through one or more bi-directional wireless communication links 2402'. This type of architecture can be well suited for implementing centralized control of the degrees-of-freedom comprised in the system definition.

Figure 26:
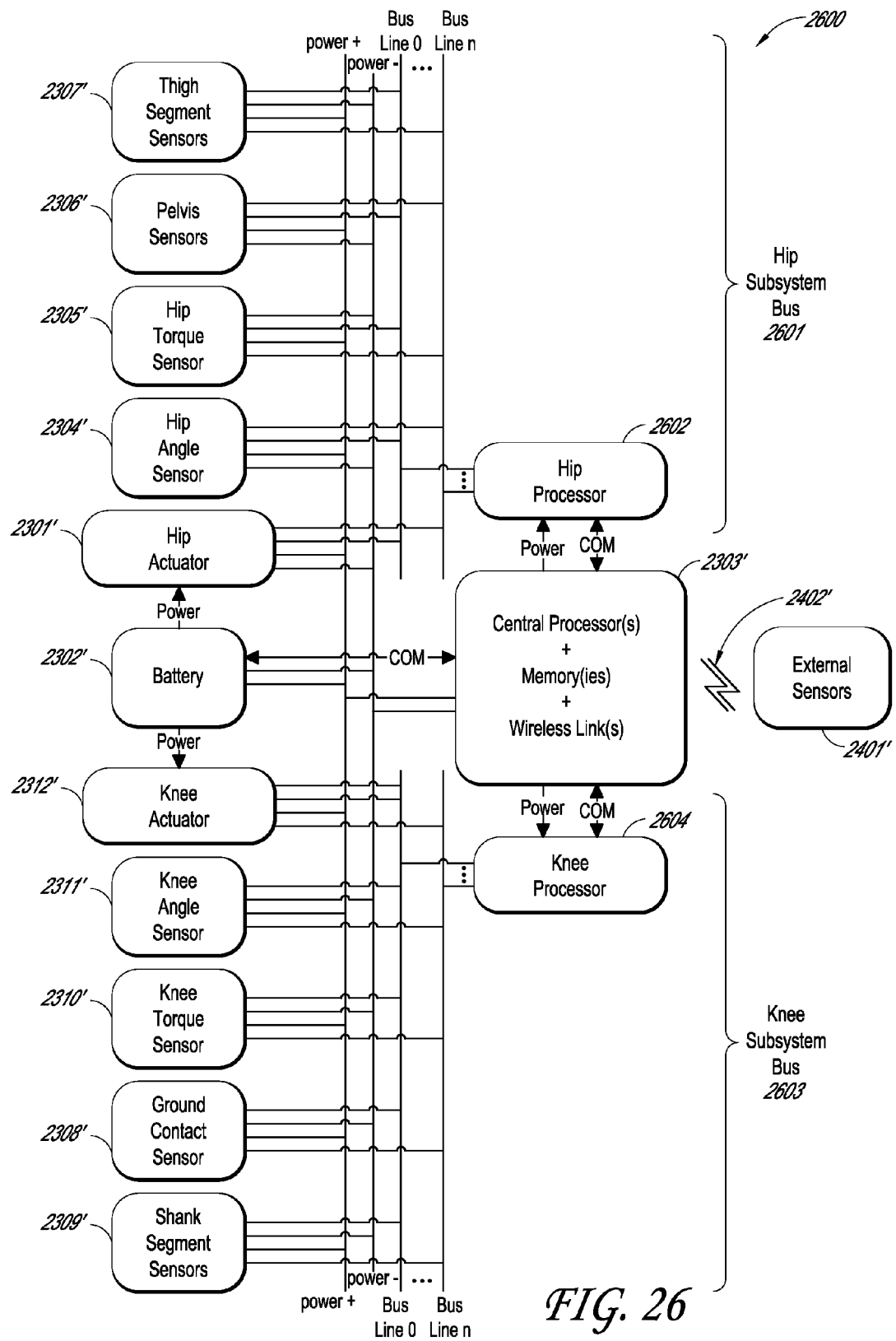
FIG. 26 is a schematic representation of hardware system architecture for a powered hip prosthetic device with dual-joints, a common power bus, and independent communication buses, according to one embodiment.

FIG. 26 presents an alternative system hardware architecture embodiment 2600. The dual-joint, battery-operated, thigh-segment prosthetic device system architecture includes a central control processor and/or electronic platform module 2303', which interfaces with two joint local processors 2602, 2604, which are also playing the role of bus controller on two subsystem buses 2601 and 2603. The overall system architecture shares a common power bus for powering sensors and actuator control interfaces, while two separate data buses are used to link together and allow communication between modules associated with each joint. While the data buses are similar in implementation to the ones illustrated in FIG. 25, use of separate data buses for each joint enables reducing the number of modules interfaced on each data bus, and allows for the use of a dedicated controller on each one. In some embodiments, these measures coupled together can allow for a higher throughput on the bus and/or data buses showing a reduced number of data lines with respect to the embodiment previously introduced in FIG. 25. This last observation is particularly true in the case where a data bus with separate control lines to address the devices independently is used as such architecture can require as many control lines as there are modules connected to the bus.

In this type of architecture where both a central processor 2303' and local joint processors 2602, 2604 are used, it is possible to assign general services to the central processor 2303', while dedicating the local joint processors 2602, 2604 to the tasks associated with sensor modules interfaces and joint motion control. General services like battery 2302' management, management of wireless link(s), and/or external sensor module 2401' interfacing can be handled by the central processor while not affecting the local joint processors' capacity to perform tasks associated with joint motion control. Furthermore, it is possible to implement centralized control in many embodiments including where the local joint processors are slaved to the central processor and/or where different types of information circulates from the central processor to the local processors. This information circulation can be based on different sensing modules being interfaced by the central processor; information stored in memory and retrieved by the central processor; and/or acquisition of external inputs by the central processor through the wireless link(s) provided by the electronic platform module 2303'. Of note, while the embodiment illustrated by FIG. 26 suggests the use of separate processors, it is also possible to implement such architecture as separate logical modules inside of a single processor platform.

As previously introduced, the use of separate local joint processors and a central processor to synchronize (and/or coordinate) the various joints of the device and/or manage the information transfer across the various modules and joints is particularly well suited for prosthetic device mechanical embodiments where the knee and hip joints are not collocated. (Separate processors, however, can be used where the joints are collocated.) An example of such an embodiment was previously introduced in FIG. 17. Under such circumstances, it can be simpler to locate the knee processor 2604 and the knee subsystem bus 2603 directly in the knee housing (e.g., knee joint assembly 1710 of FIG. 17), while the other components can be located in the thigh segment hollow cavity (e.g., 1314' of FIG. 17).

Furthermore, this type of architecture can be extended or shared across independent devices (e.g., an ankle and a knee; a hip and a knee) that offer the possibility to be connected together in an ad-hoc manner. Under such a paradigm, individual devices can be designed around the local joint processor and the subsystem bus. Each system can have its own battery to power the subsystem bus and actuator, but may or may not rely on a central processor for every device. When the two devices are connected together in an ad-hoc manner, the power bus can be merged together and communication between the local joint processors, or between one central processor and the other local joint processor can be established, depending on the exact system definition. Proper software design can allow the processors involved to recognize that they have now been connected together such that each joint can update its behavior in order to operate in the new configuration in a coordinated manner. Hence, the knee and hip device coupled together can mutually recognize the new configuration and start operating as a dual-joint thigh segment prosthetic device. Similar embodiments can also be used when coupling an ankle device to a knee device, and in some embodiments to a hip device. Once the coupling has been established by the individual devices, the devices can update their overall behavior and operational principles in order to operate as a multi joint prosthetic device.

Overview of Device Operation

As discussed above, the powered prosthetic thigh embodiments and the prosthetic hip embodiments (e.g., 100, 100', 102', 800, 800', 800", 800"', 1300, 1300', 1500, 1600, 1800, 1906, 1906') can include electronics, including a computer processor and/or controller that executes one or more algorithms to control the actuation of the actuator (e.g., electric motor) during one or more activities (such as standing, walking, and/or sitting) and transitions there between. The following operational description should not be interpreted in a limiting sense, but rather is intended to describe many diverse embodiments with optional features, steps, and elements.

Operation in Standing

In many embodiments, standing activity is defined as the basic system behavior of the prosthetic devices (e.g., 100, 100', 102', 800, 800', 800", 800"', 1300, 1300', 1500, 1600, 1800, 1906, 1906') and will be enforced by the controller whether the specific standing conditions are met or when no other activity condition can be met with sufficient certainty. Various high-level control schemes can be used to sustain this type of decision. For example, the inference layer control system described in U.S. Patent Application Publication No. 2012/0083901 and the state-machine based portion recognition module as described in U.S. Pat. No. 7,147,667 can be used.

U.S. Patent Application Publication No. 2012/0083901; U.S. Pat. No. 7,147,667; U.S. Patent Application Publication No. 2011/0125290; U.S. Pat. No. 5,383,939; U.S. Patent Application Publication No. 2006/0136072; U.S. Patent Application Publication No. 2012/0283844; and U.S. Pat. No. 7,314,490 are incorporated herein by reference in their entirety and should be considered a part of this specification.

Under the general framework of the low-level control system defined in U.S. Patent Application Publication No. 2011/0125290, two basic phases are defined. The first phase, herein referred to as the Stance phase, is where the prosthetic foot is in contact with the ground and the prosthetic lower limb is used for support. The second phase, herein referred to as the Swing phase, is where the prosthetic foot is not in contact with the ground (and the lower limb is actually suspended from the amputee's socket). In several embodiments, the detection of the Stance and/or Swing phases is provided by a ground contact sensor, as discussed above.

In various embodiments, information used to detect the stance and swing phases is provided by an instrumented foot, which can have ground sensors, contact sensors, proximity sensors, strain gauges, torque sensors, angle sensors, position sensors, and/or accelerometers. The data analysis can be performed by a prosthetic foot equipped with a stand-alone processing unit that is configured to communicate with the powered hip joint system via wired or wireless communication channel. Accelerometers can be used to measure and/or detect acceleration of the foot, knee, leg, thigh, and/or hip joint. This acceleration data can be used to identify stance and/or swing phases.

In some embodiments, following detection of the Stance phase (i.e., contact of the prosthetic foot with the ground), the reactive layer control scheme, as discussed in U.S. Patent Application Publication No. 2011/0125290, enters the FORCE REJECTION mode and the force feedback loop of the controller is configured such that all (or at least a substantial portion of) the perturbation torque measured through the serial spring deflection is rejected through equivalent actuator torque, thereby making the actuator stiff. In this configuration, the user then sits on a powered hip joint 100, 100' that is stiff, where the serial spring provides minimal compliance and allows minimal hip/pelvis motion without having to unload the lower limb. Stiffness is adjusted such that sufficient stability in standing is obtained, while still allowing the user to be able to generate minimal hip extension or flexion by moving the pelvis forward or aft.

In some embodiments, following detection of Swing phase (i.e., interruption of the contact between the prosthetic foot and the ground or a sufficient reduction of the load going through the prosthetic lower limb), the reactive layer control scheme transitions to the FORCE FOLLOWING mode using the feedback from the torque sensor as a set-point for the actuator in order to cancel the actuator drag torque and reduce the actuator stiffness, while maintaining a position bias such that the hip joint 100, 100' will move back slightly towards the neutral position N (i.e., 0°) when unloaded from a slightly flexed position during Stance phase.

Slight biasing of the hip joint position between Stance and Swing phase in static standing allows for optimizing the postural alignment of the prosthetic lower limb. Natural posture in standing for non-amputated subjects generally entails slight flexion at the hip and knee level, while the ankle remains slightly dorsi-flexed. As the hip joint is not naturally perfectly stiff and the powered hip joint 100, 100' described herein can include at least the compliance of the mechanical spring (or other compliant member) positioned between the actuator output and the thigh segment 108b, loading the prosthetic lower limb with the user's body weight can cause deflection of the joint 100, 100', which can increase the flexion angle under load. In that context, the powered hip joint 100, 100' can be biased toward a slightly flexed angle in swing phase (e.g., about 4° to about 6°; about 3° to about 15°) according to some embodiments.

It is to be noted that the standing activity described above can also be performed without the torque sensor being present in the prosthetic hip system. In another embodiment, an impedance simulating controller can be used, such as the impedance simulating motion controller described in U.S. patent application Ser. No. 13/099,961 (U.S. Patent Application Publication No. 2012/0283844). U.S. Patent Application Publication No. 2012/0283844 is incorporated herein by reference in its entirety and should be considered a part of this specification.

Other embodiments of the standing activity control scheme can also be obtained through the use of a velocity controller, which does not require a torque sensor and can be implemented using a single hip joint or motor angle sensor (although some embodiments include multiple sensors). In such an embodiment, the velocity controller can be formulated in order to achieve the general properties of an adjustable mechanical damper, where the damping rate is directly associated with the phase being detected by the system and/or determined by the phase. Hence, under conditions where the system detects Stance phase, the system can be configured to generate a behavior showing high resistance to motion (i.e., high damping rate). Under this control scheme, the hip joint would allow some motion when loaded by the user, but would not necessarily spring back to a neutral position. Furthermore, when swing phase is detected by the system, the controller gains are automatically adjusted such that a lower damping rate is achieved, which reduces the loading on the user residual limb and allows for easier manipulation of the device under certain circumstances (e.g., getting in/out of the car, donning the device).

Several control system embodiments for the operation of the powered hip prosthesis in standing activity rely on position control of the hip joint actuator. Under such control schemes, it is often possible to control the hip joint position such that a fixed position is enforced by the actuator at all times during swing and stance phase. While this simpler configuration may not always provide the same level of functional benefits as the other configurations previously outlined, such a configuration can provide robust and stable behavior, which is often preferred in the early stages of user gait rehabilitation.

Several embodiments include a balance controller to help the user stand. The balance controller detects if the user is off balance and then sends signals to actuators to correct and/or reduce the imbalance. The actuators can be any of the actuators described herein. Any of the sensors described herein can be used to detect imbalance. For example, ground contact sensors and/or accelerometers can be used to detect imbalance. Some embodiments are self-balancing like the Segway PT made by Segway Inc. The balance controller can be coupled with gyroscopic sensors and/or fluid-based leveling sensors to detect imbalance.

In some embodiments of the control system, a controller for a dual-joint thigh segment prosthetic device is designed such that the user's balance is maintained through dynamically controlling the hip and knee joints' behavior, motion, impedance, and/or torque. Such control schemes can target the stabilization of the user's center-of-mass under certain operating conditions and can dynamically modify the weight line alignment in order to maintain the user's center-of-mass inside of a certain distance from the weight line and/or prosthetic foot position.

In several embodiments of the control system, a controller for a dual-joint, thigh-segment prosthetic device is designed such that the hip and knee joints' behavior, motion, impedance, and/or torque are synchronized and/or coordinated by the controller. Under such control schemes, time-based trajectories for both joint actuators are generated by the controller, or by a motion generator, as part of the centralized control scheme. This way, optimal synergy between the two joints can be obtained.

Transition to Walking

In some embodiments, in order to transition from static standing to walking, the user initiates a walking motion by leading with the sound limb first. As the user's center-of-mass moves forward, the prosthetic thigh segment 108b moves toward hip extension with significant velocity, while a significant increase of flexion torque is measured. Fulfillment of a minimum hip extension angle (e.g., 10 degrees, 20 degrees), a minimum hip extension velocity (e.g., 20 degrees per second, 30 degrees per second), and/or a minimum flexion torque (e.g., 10 N m, 20 N m) causes the prosthetic hip system to transition to a walking activity.

In several alternative embodiments, a transition from standing activity to walking activity is detected when the hip joint is observed to reach a stance phase with sufficient flexion angle. These embodiments provide the benefit of allowing the user to initiate walking gait starting with the prosthetic limb (rather than taking the first step with the natural limb). While operating in standing activity, the user can transfer his weight on the sound side and swing the prosthetic limb forward through pelvis rotation. Landing the prosthetic foot while the hip joint is still flexed and loading the prosthetic limb makes the system transition to walking behavior.

In some embodiments, the transition from standing activity to walking activity can be detected by measuring the forward velocity of the user's pelvis, acceleration of the user's pelvis, changes in position of the user's pelvis in a global reference system, and/or other types of acceleration. Upon detection of sufficient pelvis forward velocity, acceleration and/or change of position, the system transitions to the walking behavior. Information associated with such a change of user behavior can be obtained through sensors positioned directly on the socket or on the socket interface.

In several embodiments, the transition from standing activity to walking activity is directly associated with detection of the stance to swing transition, but is coupled to a gradual powered hip joint behavior transition. Upon detection of a stance to swing transition when operating in standing activity, the system embodiment will behave as if a walking transition has been detected and will move the hip joint to a slightly flexed position. The slightly flexed position can be a position that would typically be associated with a small step in walking activity, which allows the user to either start walking or continue in standing activity. A decision regarding whether to keep supporting the gradual transition to walking activity or to maintain the standing activity would then be associated with the observation of the hip behavior in late stance, as introduced above. One benefit that can arise from the use of such a gradual transition strategy is that it can be useful in many contexts and situations, such as antero-posterior balancing and balance recovery strategy. Many embodiments enable the transition to full dynamic walking distributed over multiple steps, which allows for consistent and flexible transitions.

Operation in Walking

Operation in walking differs in many ways from the operation in standing, even if the basic foundation of operation remains the same. More specifically, the prosthetic hip system will generate and dissipate mechanical energy in a much more significant manner instead of being generally confined to a static support role.

Following detection of the walking activity by the high-level control scheme (e.g., control scheme or algorithm executed by the computer controller), such as the ones introduced above, the low-level reactive control scheme is reconfigured in order to implement additional behaviors throughout stance and swing phases to the two basic behaviors of FORCE REJECTION and FORCE FOLLOWING discussed above.

Assuming that the user initiates walking with the sound-limb first, as previously introduced, the powered hip joint 100, 100' behavior is updated at swing phase detection in some embodiments. Swing phase behavior in walking preferably enforces the basic function found at the hip joint during normal gait. Specifically, the extension motion from the stance phase is stopped, powered flexion takes place, and finally flexion motion is stopped, and the hip joint 100, 100' is prepared for the upcoming transition to stance phase. Some embodiments do not include all of these swing phase behaviors, but instead, include zero, one, or several of these swing phase behaviors. More specifically, in several embodiments, the swing phase includes stopping an extension motion from the stance phase, powering flexion, stopping flexion motion, and/or preparing the hip for an upcoming transition to stance phase.

In the general terms of the reactive level controller found in U.S. Patent Application Publication No. 2011/0125290, these specific behaviors can be implemented using a break, force following, and bumper avoidance sub-phases. In the specific context of restoring hip joint level walking gait functions, these sub-phases can be configured as per the detailed behavior descriptions provided below. Some embodiments do not use each aspect and/or element of each sub-phase.

Break

In some embodiments, following detection of swing phase transition, the prosthetic hip system enters the BREAK sub-phase. Motorized hip joint actuator behavior is configured in order to power the hip joint flexion motion. With hip power as high as 0.7 W/kg measured during a normal gait hip flexion phase for walking gait, the motorized hip joint then generates sufficient power in order to accelerate the prosthetic lower-limb as required by the user's walking cadence, typically without requiring the user to contribute through parasitic pelvis motions. BREAK sub-phase is maintained until sufficient dynamics (e.g., velocity) and hip flexion level are obtained, at which point the system transitions to the FORCE FOLLOWING sub-phase.

Force Following

In some embodiments, following the completion of the BREAK sub-phase, the prosthetic lower-limb carries enough momentum to complete the hip flexion motion without further positive contribution from the hip joint actuator. In order to maintain the hip joint momentum, the actuator operates in force following mode, in which the torque found between the actuator output 108a, operatively connected to the user pelvis, and the user thigh segment 108b is measured and fed back as a set-point to the actuator, such that null net torque is found between the two segments during this sub-phase. While this approach allows optimal use of the prosthetic lower-limb natural dynamics in some embodiments, it also reduces the prosthetic joint stiffness, which is sometimes required for user comfort and to avoid over-stressing the stump-socket interface.

In several embodiments, once the user-customized maximum hip flexion angle is attained, the prosthetic hip system transitions to the BUMPER AVOIDANCE sub-phase. In the case where the defined hip flexion angle would not be reached in a pre-defined time-frame, based on the user walking cadence, a special gait activity, herein referred to as STUMBLE RECOVERY, is entered in some embodiments.

Bumper Avoidance

In some embodiments, upon entering the BUMPER AVOIDANCE sub-phase, the actuator is reconfigured to a position and velocity tracking mode in order to dissipate the swing flexion momentum. A velocity target is defined to null velocity, which allows the system to smoothly decelerate the hip motion, while the position target allows enforcing a constant terminal swing position and sufficient hip joint stiffness prior to lower-limb transition to stance phase.

In some embodiments, an increase of the hip joint stiffness prior to occurrence of the foot strike is necessary to avoid any latency in the actuator response, which would cause delay in response and negatively affect the user's confidence level in the device's capacity to properly sustain the task at hand. Furthermore, it is sometimes necessary for the hip joint to show sufficient stiffness such that the terminal swing position is maintained while the hip joint is subject to perturbations related to knee joint extension deceleration. Failure to properly do so could lead to a drift of the hip joint towards more flexed positions, which can negatively affect the overall gait quality as the user could experience significant difficulty maintaining proper forward progression when landing on a hip showing too much flexion. In some embodiments, the BUMPER AVOIDANCE sub-phase is maintained until ground contact is detected.

In several embodiments, behavior during stance phase is segmented based on the principles discussed in U.S. Patent Application Publication No. 2011/0125290. Again, segmentation and definition of the behavior are made such that optimal interaction between the motorized prosthetic hip joint 100, 100' and the user is obtained, as well as obtaining optimal restoration of the user level walking gait. In some embodiments, stance phase is then divided into two sub-phases, namely the FORCE REJECTION and the TOE-OFF ASSIST sub-phases. These two sub-phases are configured to sustain the two basic behaviors of the normal hip during level walking gait: controlled hip extension and hip flexion preparation. The following sections provide more details on the nature and boundaries for the stance phase hip joint behavior.

Force Rejection

In some embodiments, following detection of the prosthetic limb's contact with the ground, the prosthetic hip system transitions automatically to the FORCE REJECTION sub-phase. The FORCE REJECTION sub-phase enforces the controlled extension of the hip under the influence of the external load imposed by the upper body mass and momentum. The actuator then operates in velocity regulation mode, which allows the body's center-of-mass to move over the prosthetic limb in a uniform and smooth manner. FORCE REJECTION behavior can be customized to user preferences, body mass, and gait preferences at least partially through varying the amplitude of the regulation strength and target velocity. Furthermore, automatic adjustment of the velocity regulation strength and target velocity based on the measured walking cadence and/or forward linear velocity can also be performed in order to achieve natural gait. Once the maximum extension angle has been reached, the prosthetic hip system automatically transitions to the TOE-OFF ASSIST sub-phase in some embodiments.

Toe-Off Assist

In some embodiments, once the hip extension angle reaches the value configured based on user preferences and gait style, the system transitions to TOE-OFF ASSIST sub-phase. As per indicated by its name, this sub-phase handles the requirements associated with making sure that the unloading of the prosthetic foot takes place in a controlled and physiologically coherent manner. In order to do so, actuator behavior is modified from the controlled velocity mode of the previous sub-phase. Hence, the stiffness of the powered hip-joint 100, 100' is increased to stop the extension motion, and a slight position bias towards flexion is created in order to reduce extension torque on the knee and ease this transition to a flexion motion.

In several embodiments, for highly dynamic gaits to be achieved, it is necessary and/or beneficial to initiate the TOE-OFF ASSIST sub-phase while the prosthetic device is still loaded (approximately at 55% of the stride cycle). In some embodiments, the TOE-OFF ASSIST sub-phase is initiated at about 45% to about 65% of the stride cycle, at about 50% to about 70% of the stride cycle, or at about 40% to about 80% of the stride cycle.

For less dynamic walking gaits, such as observed under low cadence, linear speed, or in the early stage of gait rehabilitation, it is desirable to move the occurrence of the TOE-OFF ASSIST sub-phase later in the stride cycle, such that increased stability is achieved. In some embodiments, the TOE-OFF ASSIST sub-phase is initiated at about 80% to 95% of the stride cycle or after more than 75% of the stride cycle. TOE-OFF ASSIST sub-phase is exited once the lower-limb prosthetic transitions to swing phase.

In several alternative embodiments of the walking activity control system, a simpler form of control system is designed such that it can be operated using a single hip joint angle sensor, coupled to the ground contact detection sensor previously introduced. (Several similar embodiments use additional sensors.) Under such a control scheme, joint motion trajectories are stored in memory and dynamically scaled in real-time as the basic gait events associated with the hip joint in level walking are detected. Hence, following detection of foot strike in walking activity, the stance phase joint trajectory will be scaled with respect to swing phase measured cadence and the position targets for the hip actuator motion controller will be provided. Position targets can be provided at a real-time control frequency. The hip actuator motion controller can govern the system at a real-time control frequency. The trajectory can cover the complete actuator behavior until swing phase is detected. At this point in time, a similar process takes place in order to adjust the swing phase trajectory based on the measured cadence during stance phase. It is to be noted that the definition of the real-time joint trajectories can be based on more parameters than walking cadence only. Other parameters, such as user weight, user segment length ratios, rehabilitation level, and/or gait style, can be used to further define the joint trajectory.

In some embodiments, use of time-based joint trajectory to derive the actuator behavior and motion characteristics during level walking swing and stance phase sometimes generates a less flexible system for the user. However, this type of system can bring significant benefits in certain operational contexts. One benefit with this type of control system arises from its very high consistency in operation and the relatively low requirements for the user to reproduce the normal gait triggers associated with level walking. Hence, this type of system can be particularly well suited for users in early rehabilitation stages.

Some embodiments use different TOE-OFF ASSIST sub-phase approaches, which can be used alone or in combination with other TOE-OFF ASSIST sub-phase approaches to power up walking. The FORCE REJECTION sub-phase is maintained until the user's center of mass is found to be aligned with the prosthetic foot in the sagittal plane. From that point on, TOE-OFF ASSIST is triggered based on the measurement of the swept thigh angle since foot strike and/or based on the hip torque sign transition (from flexion to extension). Once TOE-OFF ASSIST is triggered, TOE-OFF ASSIST is used and configured in order to power hip extension and push the user forward. For limited walking, the first behavior can be implemented in order to sustain non-cyclical motion and provide a stable set-up. Following attainment of a cadence threshold, the system can switch to the second behavior in order to provide a higher gait powering contribution to the user's forward progression.

Transition to Standing

In order to transition back to a standing mode, one use strategy includes stopping on the prosthetic limb (rather than stopping on the sound limb). In these specific use-cases, the user initiates stance phase in a normal manner, but instead of completing the full hip extension motion, as performed during level walking gait, the user stops his motion using the controlled velocity actuator behavior. Following detection by the system that the actual hip extension velocity has reduced below a configurable threshold (e.g., 20 degrees per second, 30 degrees per second), the system will revert to operation in standing activity using the actual hip joint sagittal plane position as the default position, from which the standing activity FORCE REJECTION behavior will be enforced.

In several embodiments, transition to standing activity is directly detected through the use of pelvis forward velocity, acceleration, and/or a change of position sensing system, as introduced above. Use of an accelerometer functionally coupled to the user socket provides the type of information used by several transition detection scheme embodiments. Following detection of the user deceleration and/or reduction of forward velocity, the system then immediately reverts to standing activity.

In some embodiments, detection of a level walking cadence decrease below a predefined threshold, stance duration over a predetermined level and/or a swing duration increase over a predetermined level are used in order to determine whether transition back to standing activity has occurred. In these contexts, increased responsiveness can be obtained from the use of the stance and/or swing duration in order to perform this specific detection. Apart from the cadence assessment that can remain constant between its evaluation at discrete points in time (i.e., foot strike and/or foot off), verification of the stance or swing duration exceeding a predetermined threshold can be done in a continuous manner, hence yielding a more responsive detection mechanism.

Transition to Sitting

In some embodiments, transition to sitting activity is made through the triggering of the sit-down activity. The sitting-down activity reconfigures the FORCE REJECTION mode of the standing activity such that controlled flexion of the hip joint is obtained, allowing the user to control transition to a seated position, while still transferring weight through the prosthetic limb. Multiple parameters can be monitored in order to detect the user's intent to transition from the standing activity to sitting down. One parameter that can be used is the hip joint flexion torque. Measurement of the absolute segment angles using accelerometers and/or gyroscopic sensors can also be used to detect a transition to sitting. Once the system is unloaded, the system transitions to the sit activity.

Sitting-down activity joint behavior can be implemented using a velocity controller, which allows the system to regulate the hip joint flexion velocity during the activity. The controller parameters (i.e., velocity gain and velocity set-point) can be adjusted based on user preferences and/or functional limitations such that adequate behavior is obtained. Several embodiments use a constant null velocity set-point and allow for the velocity gain to be adjusted in order to achieve a joint resistance level adequate with the user preferences and capacities. Other embodiments use controller formulation allowing for power dissipation. For example, some embodiments use a formulated a torque controller to achieve similar behavior and performance.

In another embodiment of the powered hip joint controller described herein, the sitting-down activity detection is performed by again measuring the presence of a minimum level of flexion torque when the hip position is measured to be more flexed than a pre-determined level.

In a further embodiment of the powered hip joint controller described herein, the sitting-down activity detection is manually triggered by the user using a button located on the device.

In a further embodiment of the powered hip joint controller described herein, the sitting-down activity detection is performed by measuring the tilt angle of the pelvis. Measurement of the sagittal plane tilt angle of the pelvis can be performed using a two or three axis accelerometer used in inclinometer mode and operatively coupled to the user socket. Under static or quasi-static conditions, two or three axis accelerometers like the ADXL330 accelerometer made by Analog Devices can be used as an inclinometer, as the ratio of the measurement of the gravity along the two axes positioned in sagittal plane will provide a direct indication of their alignment with respect to gravity. Detection of static or quasi-static conditions can be made by monitoring the magnitude of the net acceleration vector as reported by the sensors. When the magnitude of the acceleration vector is found to be close to 1 g (e.g., less than about 1.1 g, less than about 1.3 g), a reasonable assumption can be made that the sensor is either static or quasi-static. When the user's pelvis is detected to be tilted forward by more than a predefined threshold (i.e., the user is leaning forward), the sitting-down transition is performed, as this position is characteristic of a user initiating a stand-to-sit transition. This threshold can be 15 degrees, 25 degrees, 35 degrees, and/or 45 degrees as measured from a vertical axis.

Operation in Sit Activity

In some embodiments, powered hip joint operation while the user is seated is designed in such a way as to limit the interference between the prosthetic hip joint 100, 100' and the user's motion while seated. In that context, the actuator can be as compliant as possible in several embodiments. This actuator behavior is implemented through the use of the FORCE FOLLOWING sub-phase and inherent motion control behavior, as discussed above. In some embodiments, the prosthetic hip joint 100, 100' can be operated to enter a standby mode upon detection of the user's lack of motion for a certain time period, in order to optimize the use of battery power while seated. In such an embodiment, all non-required hip joint sub-systems can be disabled, thereby saving energy and optimizing the device autonomy. When operating in standby activity, the actuator can be left in its passive state and brought back on-line only when sufficient user motion would be detected (e.g., when user motion exceeds a predetermined threshold amount).

Transition to Standing

In some embodiments, a transition from the sit activity and seated position to the standing activity and standing position is supported by the prosthetic hip joint 100, 100' by implementing the standing-up activity. Standing-up activity is detected when the position and/or velocity of the user's thigh segment 108b starts changing from a mostly horizontal orientation towards a vertical one. Upon detection of these last conditions, the hip joint behavior will be modified in order to implement a single sided force-rejection behavior. This specific actuator behavior allows the user to incrementally perform hip extension while standing-up by having the actuator allow mostly free motion in the hip extension direction, while still providing full support when the motion is in the hip flexion direction. Once a hip flexion angle indicates that the thigh segment is mostly vertical, and load is applied through the prosthetic lower-limb, the system transitions to the standing activity, as discussed above.

In an alternative embodiment, the transition from sitting to standing is performed by monitoring a transition to stance phase, while seated, combined with a change of the hip joint angle. As the device operates in FORCE FOLLOWING mode under sitting conditions, a natural way for a user to initiate a transition to standing is through tilting the upper body forward, which causes a change of the hip joint angle. As the user tilts his/her upper body forward, the hip joint typically undergoes a flexion motion as the user's center-of-mass moves over the prosthetic foot. Such a change of the hip joint angle is typically indicative of an upcoming transition from sitting to standing and can be used in order to modify the hip joint behavior (e.g., to help the user transition to standing).

In some embodiments, sensors detect if the user is no longer placing sitting forces on the user's socket and if the user exhibits at least one other indication of transitioning to standing (as described above). If these factors are met, the system transitions to the standing activity, as discussed above.

In order to accommodate various user profiles, gait style and mobility level requirements, the motorized prosthetic hip joint 100, 100' can be configured from a default configuration state using a software application, which can be run on a desktop computer, portable computer or mobile communication platform. Included among the parameters that can be configured using said software to better suit user personal preferences, gait style and mobility level, are: level walking maximum hip flexion angle, level walking maximum hip extension angle, level walking stance phase hip extension resistance level, level walking swing phase hip flexion velocity, sitting-down resistance level, sit activity standby mode enabling/disabling, and standing activity joint stiffness level. However, other parameters can be adjusted to better suit user personal preferences, gait style and mobility level.

The powered hip joint 100, 100' discussed above provides many advantages over conventional mechanical hip joints, including but not limited to enforcing stable neutral hip joint positioning in static standing, controlling stance phase maximum hip extension angle, providing mechanical energy in swing extension, controlling swing terminal hip flexion angle, and automatically adjusting to the user's walking cadence.

In some embodiments, the powered hip joint 100, 100' can be combined with a knee joint, such as a powered knee joint described in U.S patent application publications incorporated by reference in this specification, in a single hardware platform. In such an embodiment, two actuators are located at each end of the prosthetic thigh segment 108b, while common electronics and power source are located along the prosthetic thigh segment 108b. Advantageously, such an embodiment can allow for a highly beneficial combination of a power-generating hip and knee. For example, power-generating hip and knee combinations can provide many benefits through the use of common parallel control schemes where knee and hip behavior can be synchronized and/or coordinated for tasks such as sitting down, standing up, walking, and/or maintaining balance while standing. This synchronized and/or coordinated behavior can be used where coordinated knee and hip behavior greatly improves the functional outcomes of the prosthetic device and reduces strain on the user.

Although these inventions have been disclosed in the context of a certain preferred embodiments and examples, it will be understood by those skilled in the art that the present inventions extend beyond the specifically disclosed embodiments to other alternative embodiments and/or uses of the inventions and obvious modifications and equivalents thereof. In addition, while a number of variations of the inventions have been shown and described in detail, other modifications, which are within the scope of the inventions, will be readily apparent to those of skill in the art based upon this disclosure. It is also contemplated that various combinations or subcombinations of the specific features and aspects of the embodiments may be made and still fall within one or more of the inventions. For example, steps of the method(s) disclosed herein can be performed in an order other than that disclosed in the illustrated embodiments, and additional, fewer, or different steps may be performed and still fall within the scope of the inventions. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above.

What is claimed is:

1. A powered prosthetic thigh, comprising:
   a proximal connector having a first end and a second end along a longitudinal axis;
   a proximal portion coupled to the first end of the proximal connector, wherein the second end of the proximal connector is configured to couple the prosthetic thigh to a prosthetic socket, wherein the prosthetic socket is configured to attach to an amputee and comprises a compliant member configured to deform, wherein deformation of the compliant member provides for relative lateral motion between the prosthetic socket and the powered prosthetic thigh;
   a distal portion attached to the proximal portion, the distal portion comprising a distal connector configured to couple to a prosthetic knee; and
   a computer controlled actuator mounted collinearly to the proximal connector along the longitudinal axis and configured to rotate the prosthetic thigh along a sagittal plane relative to the prosthetic socket attached to the amputee, wherein at least a portion of the computer controlled actuator is located proximally to the first end of the proximal connector.

2. The powered prosthetic thigh of claim 1, wherein the actuator comprises a motor and a transmission.

3. The powered prosthetic thigh of claim 2, wherein the motor is operatively coupled to the proximal connector by at least one of a gear, a belt, or a chain.

4. The powered prosthetic thigh of claim 2, wherein the transmission is mounted collinearly with the proximal connector.

5. The powered prosthetic thigh of claim 2, wherein the motor is mounted collinearly with the transmission.

6. The powered prosthetic thigh of claim 2, wherein the actuator comprises a hydraulic pump and the transmission comprises a hydraulic transmission system.

7. The powered prosthetic thigh of claim 1, wherein the compliant member comprises at least one spring coupled to the prosthetic socket and a receiver for the proximal connection.

8. The powered prosthetic thigh of claim 1, wherein the actuator is further mounted coaxially to the proximal connector.

9. A powered prosthetic hip, comprising:
prosthetic socket configured to couple to an amputee, the prosthetic socket having a longitudinal axis;
a proximal connector having a first end and a second end along the longitudinal axis, the second end coupled to the prosthetic socket; and
a powered prosthetic thigh pivotably coupled to the prosthetic socket by the proximal connector, the powered prosthetic thigh comprising:
a proximal portion coupled to the first end of the proximal connector, wherein the prosthetic socket comprises a compliant member configured to deform, wherein deformation of the compliant member provides for relative lateral motion between the prosthetic socket and the powered prosthetic thigh,
a distal portion attached to the proximal portion, the distal portion comprising a distal connector configured to couple the powered prosthetic thigh to a prosthetic knee, and
a computer controlled actuator mounted collinearly to the proximal connector along the longitudinal axis and configured to rotate the powered prosthetic thigh along a sagittal plane relative to the prosthetic socket, wherein at least a portion of the computer controlled actuator is located proximally to the first end of the proximal connector.

10. The prosthetic hip of claim 9, wherein the prosthetic socket comprises a compliant member configured to deform, wherein deformation of the compliant member allows relative lateral motion between the prosthetic socket and the powered prosthetic thigh.

11. The prosthetic hip of claim 10, wherein the compliant member comprises at least one spring located between a portion of the prosthetic socket and a portion of the powered prosthetic thigh.

12. The prosthetic hip of claim 9, wherein the proximal connector comprises an attachment arm that pivotably couples the prosthetic socket and the powered prosthetic thigh, wherein the prosthetic socket comprises a front wall, and the attachment arm is pivotably coupled to the front wall.

13. The prosthetic hip of claim 9, wherein the prosthetic socket comprises a front wall and the proximal connector comprises an attachment arm with a first portion and a second portion, wherein the first portion is coupled to the powered prosthetic thigh and the second portion is pivotably coupled to the front wall.

14. The prosthetic hip of claim 13, wherein the prosthetic hip is configured to allow the powered prosthetic thigh to move from underneath the prosthetic socket to enable a sitting mode.

15. The prosthetic hip of claim 14, further comprising a lock configurable to prevent the attachment arm from pivoting relative to the prosthetic socket.

\* \* \* \* \*

UNITED STATES PATENT AND TRADEMARK OFFICE
CERTIFICATE OF CORRECTION

PATENT NO. : 9,044,346 B2
APPLICATION NO. : 13/837124
DATED : June 2, 2015
INVENTOR(S) : Langlois et al.

It is certified that error appears in the above-identified patent and that said Letters Patent is hereby corrected as shown below:

In the Specification

In column 16 at line 41, Change "800"" to --800".--.

In column 18 at line 49, Change "1312"' to --1312'.--.

In column 23 at line 25, Change "1807'," to --1807'.--.

In column 25 at line 14, Change "1904'," to --1904'.--.

In column 26 at line 24, Change "-/-40%." to --+/-40%.--.

In column 28 at line 62, Change "System" to --system--.

In column 31 at line 53, Change "quality," to --quality.--.

In the Claims

In column 45 at line 8 (approx.), In Claim 9, before "prosthetic" delete "powered".

Signed and Sealed this
Twenty-sixth Day of April, 2016

Michelle K. Lee
*Director of the United States Patent and Trademark Office*